(12) United States Patent  
Bodner

(10) Patent No.: US 12,383,120 B2  
(45) Date of Patent: Aug. 12, 2025

(54) ENDOSCOPE

(71) Applicant: Daryl Bodner, Millersville, PA (US)

(72) Inventor: Daryl Bodner, Millersville, PA (US)

(*) Notice: Subject to any disclaimer, the term of this patent is extended or adjusted under 35 U.S.C. 154(b) by 968 days.

(21) Appl. No.: 15/774,281

(22) PCT Filed: Nov. 11, 2016

(86) PCT No.: PCT/US2016/061530  
§ 371 (c)(1),  
(2) Date: May 8, 2018

(87) PCT Pub. No.: WO2017/083648  
PCT Pub. Date: May 18, 2017

(65) Prior Publication Data  
US 2019/0246878 A1 Aug. 15, 2019

Related U.S. Application Data

(60) Provisional application No. 62/255,025, filed on Nov. 13, 2015.

(51) Int. Cl.
| | | |
|---|---|---|
| A61B 1/00 | (2006.01) |
| A61B 1/005 | (2006.01) |
| A61B 1/015 | (2006.01) |
| A61B 1/05 | (2006.01) |
| A61B 1/06 | (2006.01) |

(Continued)

(52) U.S. Cl.  
CPC ...... *A61B 1/00091* (2013.01); *A61B 1/00009* (2013.01); *A61B 1/00042* (2022.02); *A61B 1/00045* (2013.01); *A61B 1/0057* (2013.01); *A61B 1/015* (2013.01); *A61B 1/05* (2013.01); *A61B 1/0676* (2013.01); *A61B 1/126* (2013.01); *G02B 23/2476* (2013.01)

(58) Field of Classification Search  
CPC ............ A61B 1/00091; A61B 1/00096; A61B 1/0008; A61B 1/00119; A61B 1/0051; A61B 1/0055; A61B 1/126; A61B 1/12; A61B 1/233  
See application file for complete search history.

(56) References Cited

U.S. PATENT DOCUMENTS

| | | |
|---|---|---|
| 4,403,985 A | 9/1983 | Boretos |
| 4,802,461 A | 2/1989 | Cho |

(Continued)

*Primary Examiner* — Michael J Carey  
*Assistant Examiner* — Stephen Floyd London  
(74) *Attorney, Agent, or Firm* — Blank Rome LLP

(57) ABSTRACT

A semi-rigid endoscope may include a shaft that is elongate along a longitudinal direction. The shaft including a shaft body that defines: proximal rigid portion and a flexible tip that is distal to the proximal rigid portion. The flexible tip moves along a lateral direction that is perpendicular to the longitudinal direction. The flexible tip moves along a transverse direction that is perpendicular to both the longitudinal and lateral directions. The endoscope may also include at least one conduit that extends longitudinally along an internal portion of the shaft body. The internal portion may be substantially enclosed, such that the at least one conduit transfers irrigant fluid to and from the flexible tip. The endoscope may also include a baffle that directs irrigant fluid at the flexible tip and an image sensor coupled to the flexible tip.

27 Claims, 64 Drawing Sheets

(51) Int. Cl.
*A61B 1/12* (2006.01)
*G02B 23/24* (2006.01)

(56) References Cited

U.S. PATENT DOCUMENTS

| | | | | |
|---|---|---|---|---|
| 5,307,804 | A * | 5/1994 | Bonnet | A61B 1/042 396/17 |
| 5,373,317 | A | 12/1994 | Salvati et al. | |
| 5,575,756 | A * | 11/1996 | Karasawa | A61B 1/00068 600/121 |
| 5,857,998 | A * | 1/1999 | Barry | A61F 2/82 604/103.02 |
| 5,899,851 | A * | 5/1999 | Koninckx | H04N 5/2259 600/117 |
| 5,989,183 | A * | 11/1999 | Reisdorf | A61B 1/00142 600/156 |
| 6,097,423 | A * | 8/2000 | Mattsson-Boze | A61B 1/00045 348/66 |
| 6,346,076 | B1 * | 2/2002 | Rovegno | A61B 1/00177 600/137 |
| 6,471,637 | B1 * | 10/2002 | Green | A61B 1/00045 600/137 |
| 6,500,115 | B2 * | 12/2002 | Krattiger | A61B 1/0052 600/137 |
| 7,381,183 | B2 * | 6/2008 | Hale | A61B 1/0005 600/117 |
| 8,888,683 | B2 * | 11/2014 | Mejia | A61B 1/00052 600/109 |
| 8,915,842 | B2 * | 12/2014 | Weisenburgh, II | A61B 1/00091 600/156 |
| 9,146,576 | B2 * | 9/2015 | Schmieding | A61B 1/00066 |
| 10,542,868 | B2 * | 1/2020 | Gordon | A61B 1/126 |
| 2002/0099263 | A1 * | 7/2002 | Hale | A61B 1/00147 600/117 |
| 2004/0249246 | A1 * | 12/2004 | Campos | A61B 1/00165 600/160 |
| 2005/0119527 | A1 * | 6/2005 | Banik | A61B 1/0051 600/117 |
| 2006/0020165 | A1 * | 1/2006 | Adams | A61B 1/00094 600/121 |
| 2006/0084840 | A1 * | 4/2006 | Hoeg | A61B 1/042 600/117 |
| 2007/0249899 | A1 | 10/2007 | Seifert | |
| 2008/0103361 | A1 * | 5/2008 | Makower | A61M 29/02 600/115 |
| 2009/0253965 | A1 * | 10/2009 | Miyamoto | A61B 1/042 600/157 |
| 2011/0230716 | A1 * | 9/2011 | Fujimoto | G02B 23/2476 600/121 |
| 2012/0078055 | A1 * | 3/2012 | Berci | A61B 1/04 600/188 |
| 2013/0006055 | A1 * | 1/2013 | Goldfarb | A61B 1/00039 600/137 |

\* cited by examiner

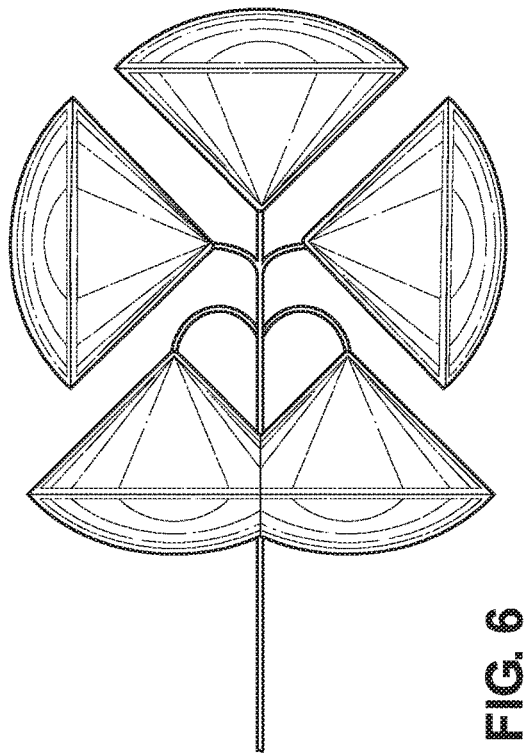
FIG. 5
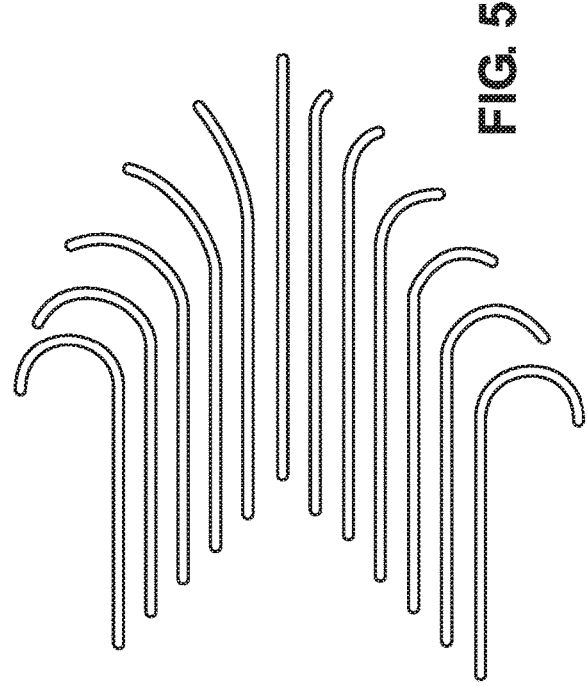
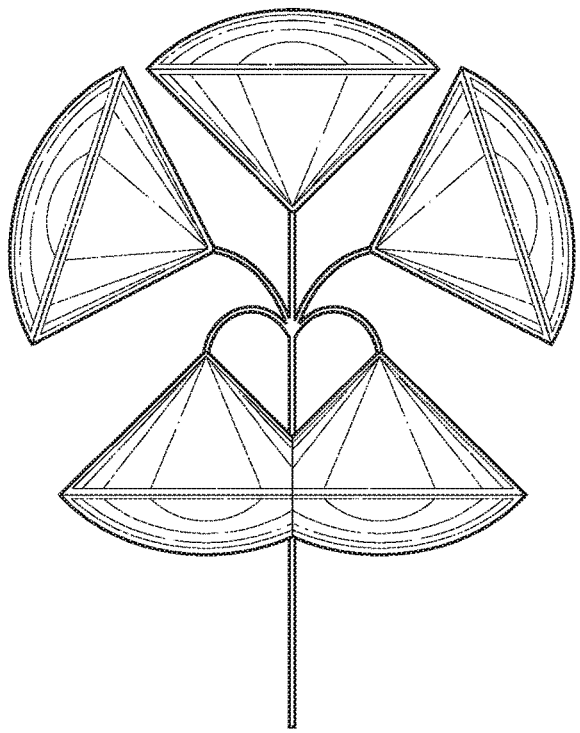
FIG. 6

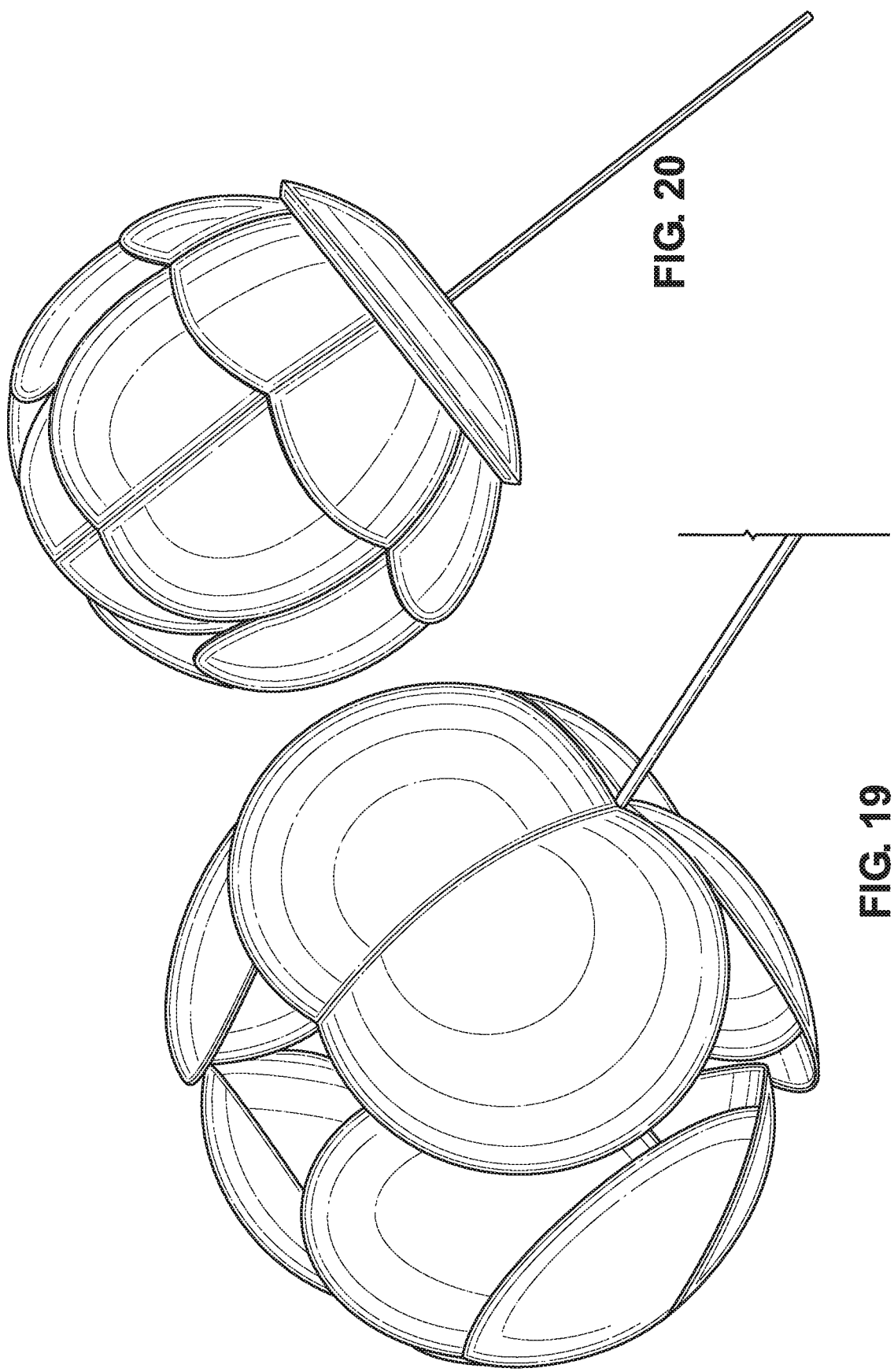

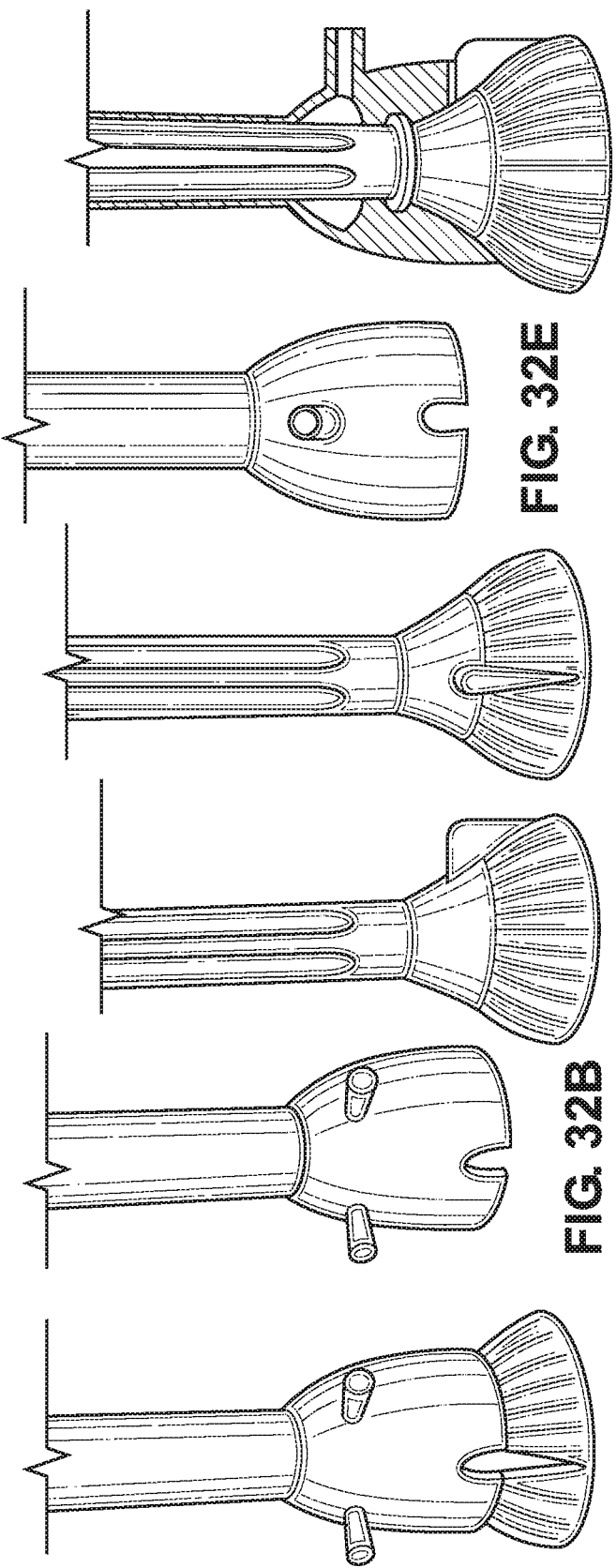

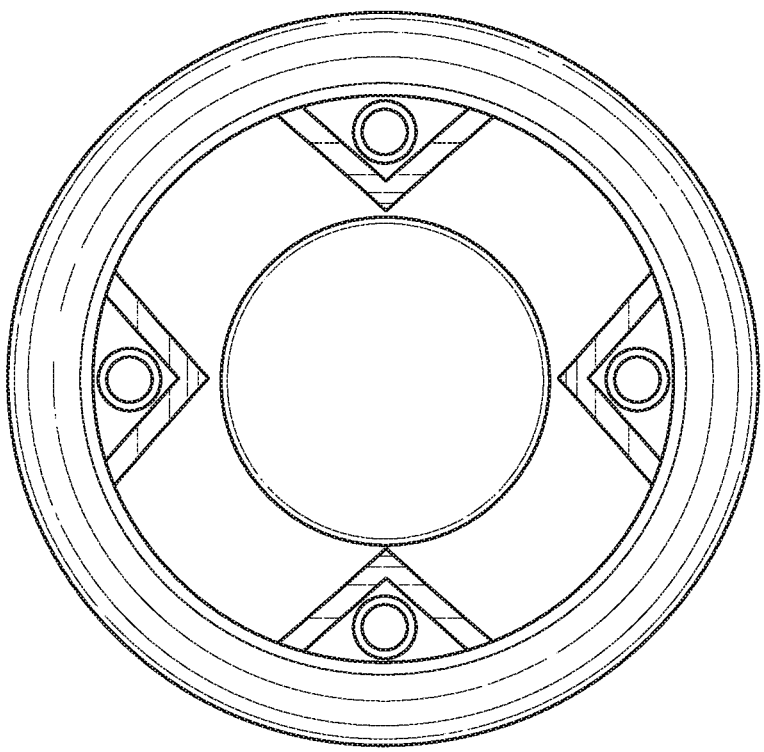
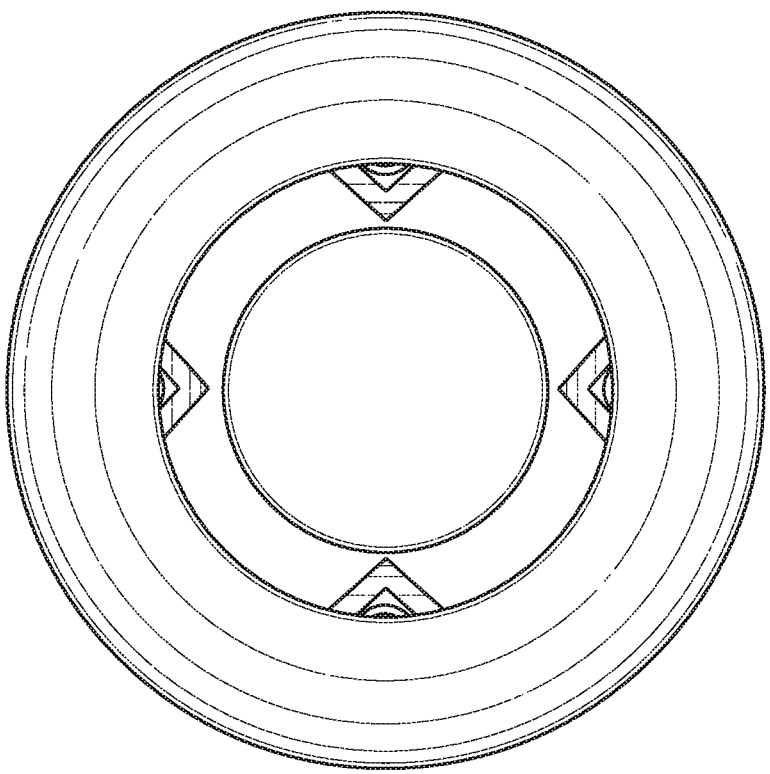
FIG. 35A

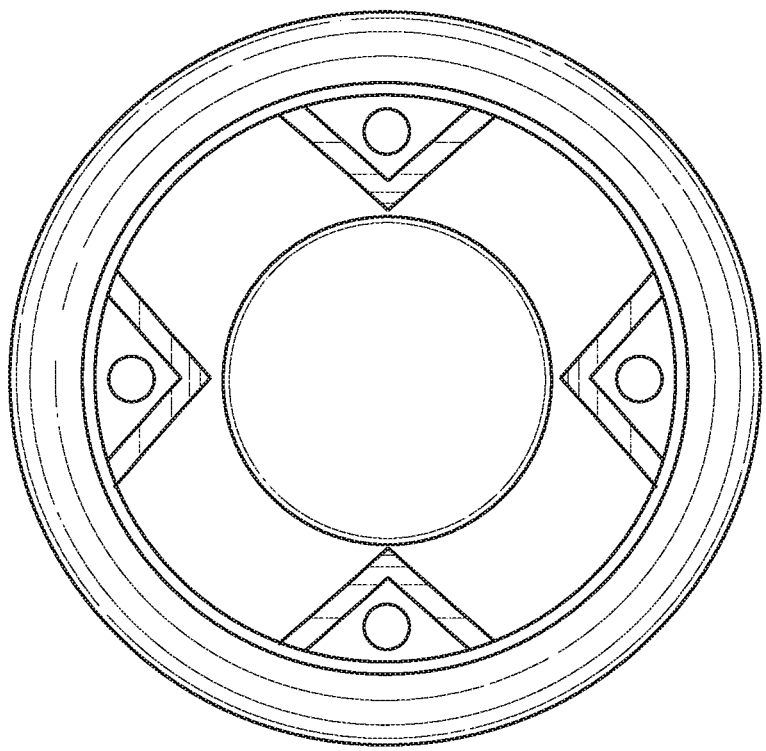
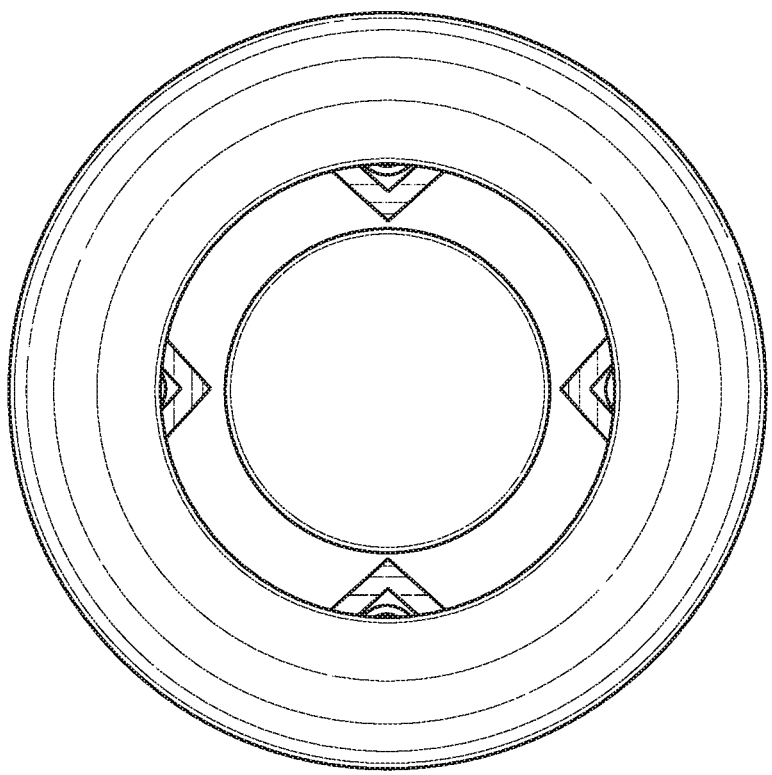
FIG. 35B

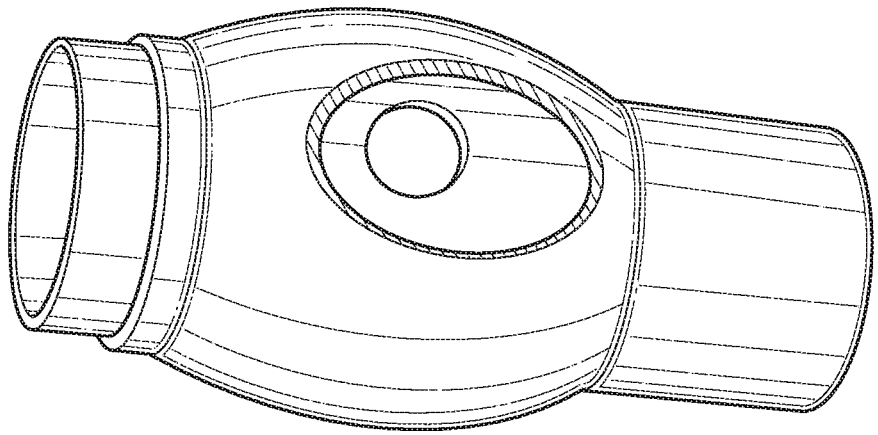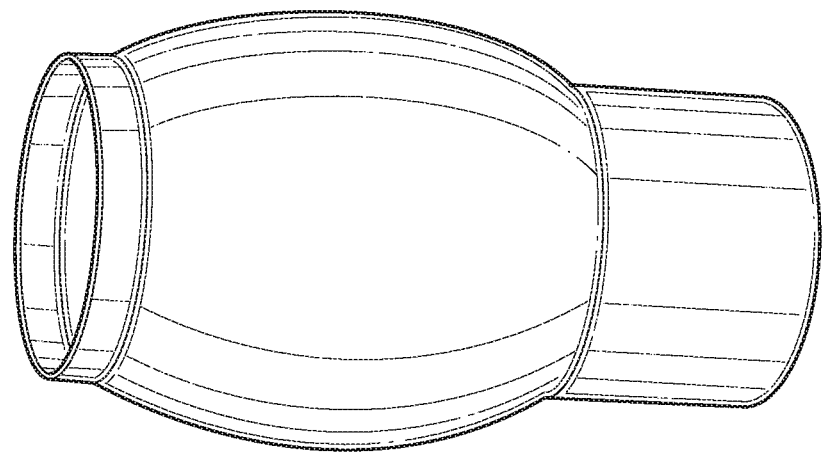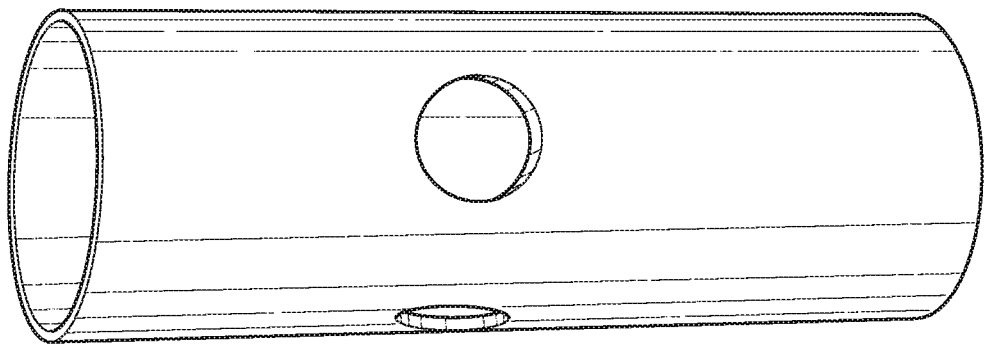
FIG. 38

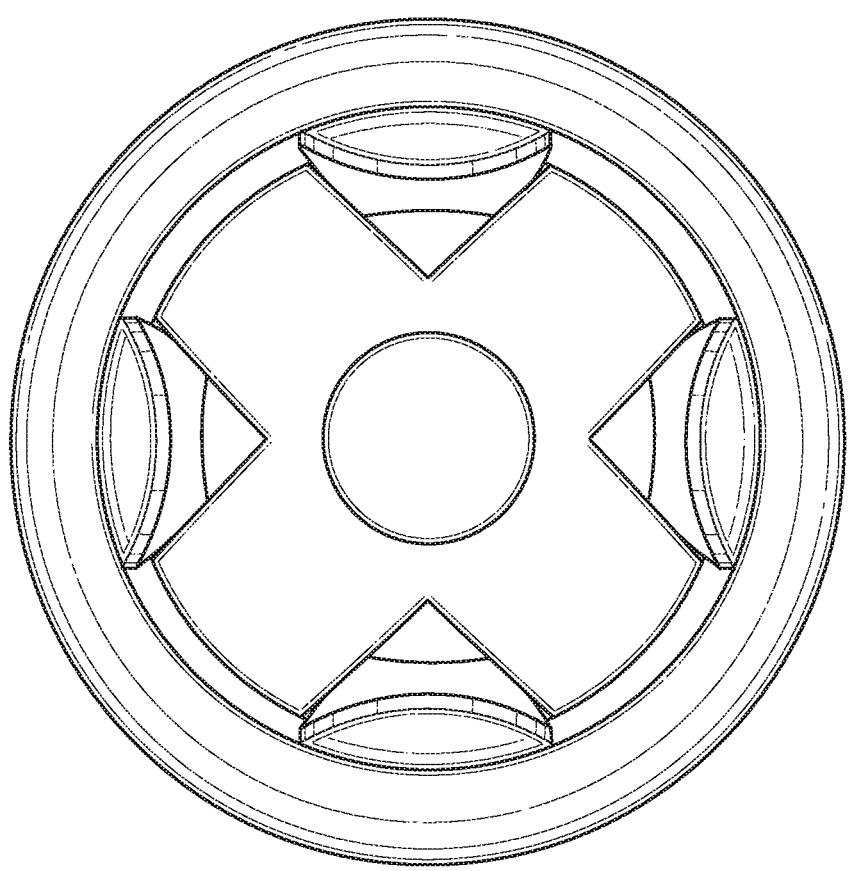
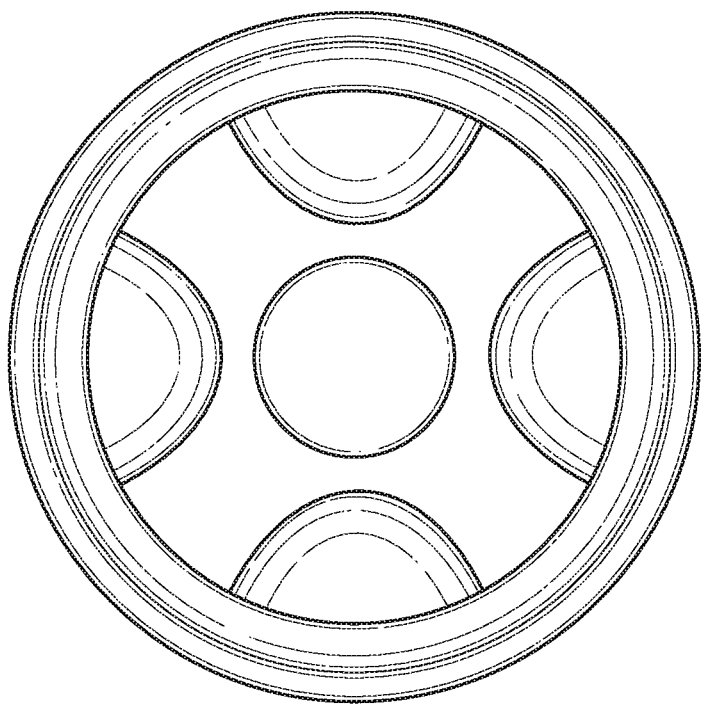
FIG. 39

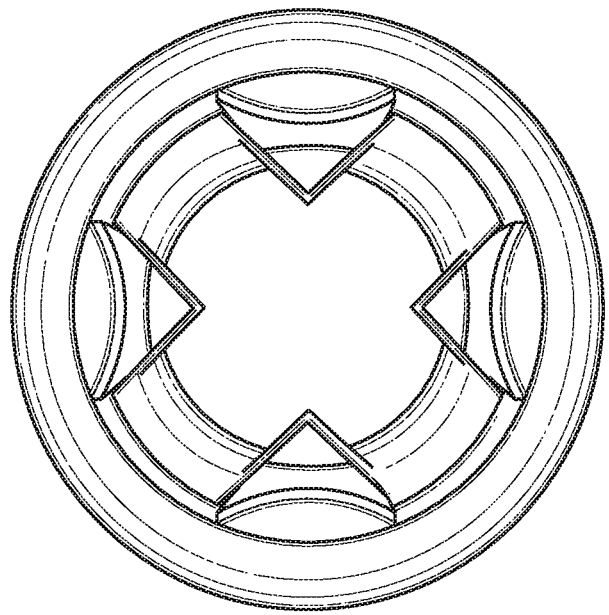
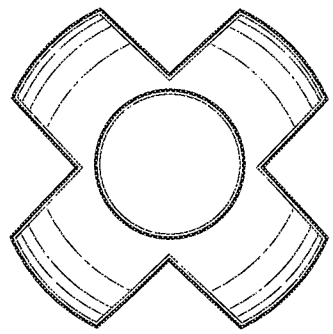
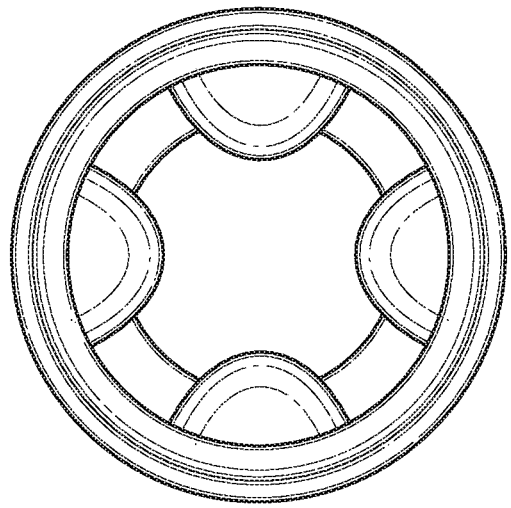
FIG. 40

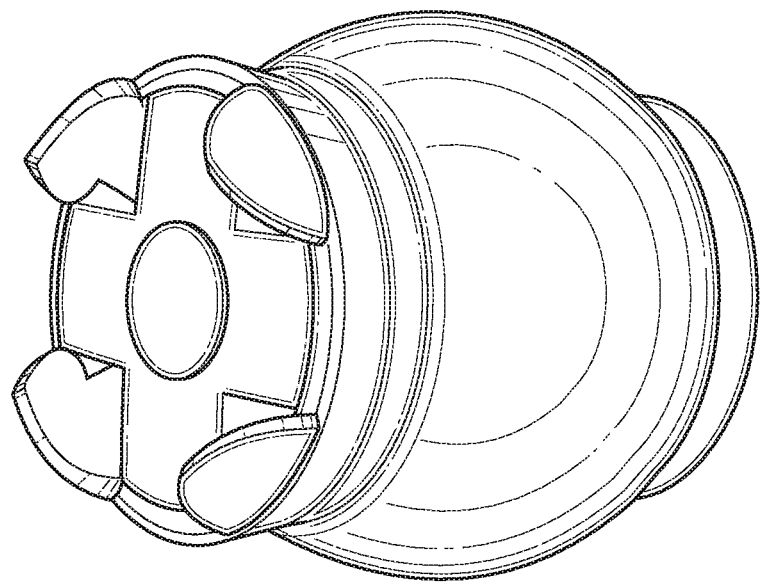
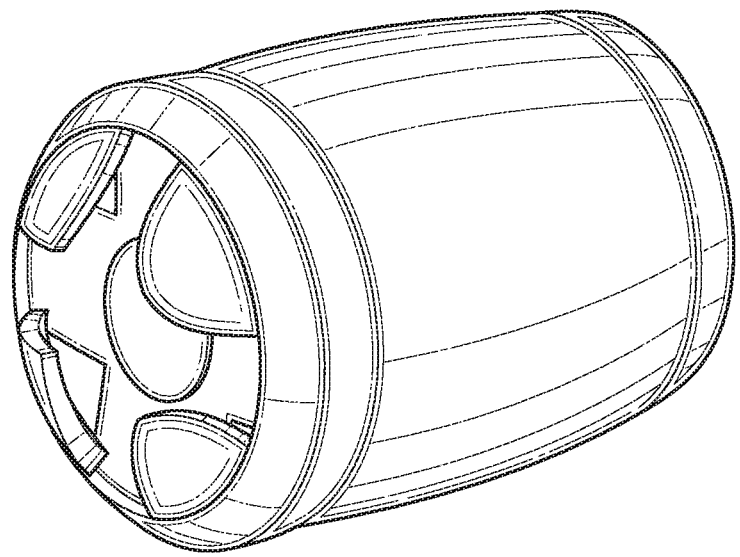
FIG. 42

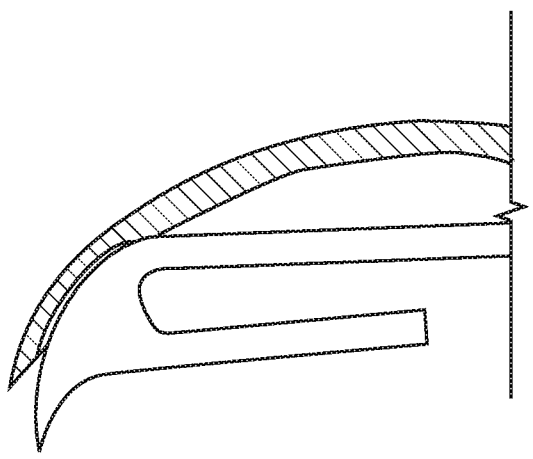
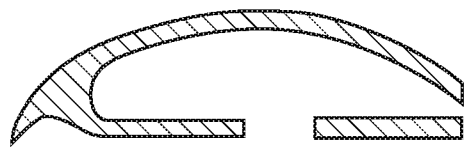
FIG. 43A
FIG. 43B
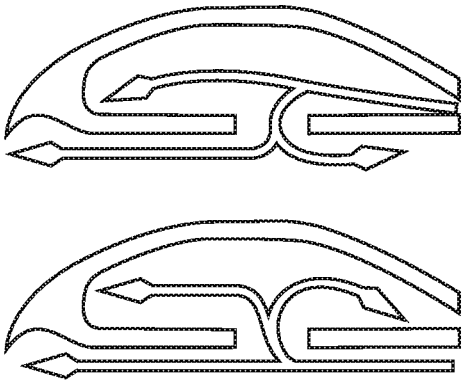
FIG. 43C

FIG. 49
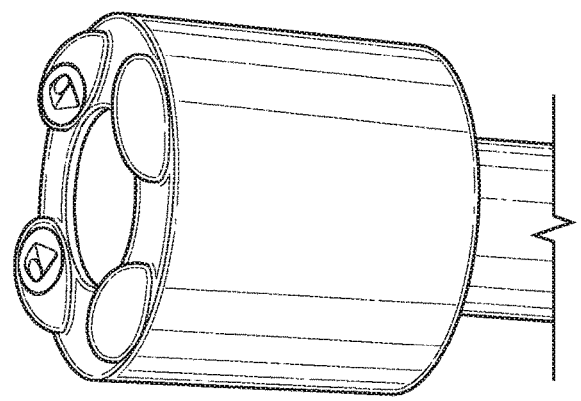
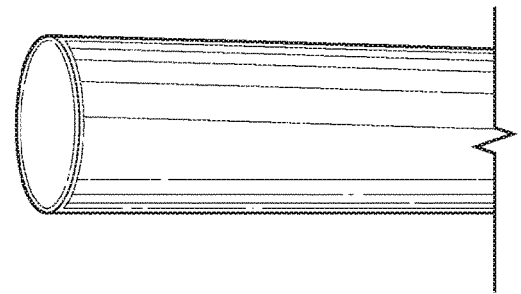
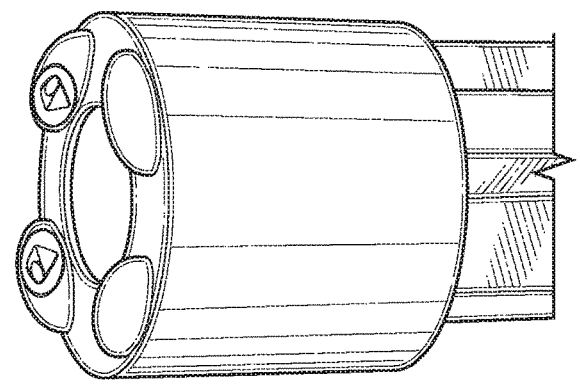
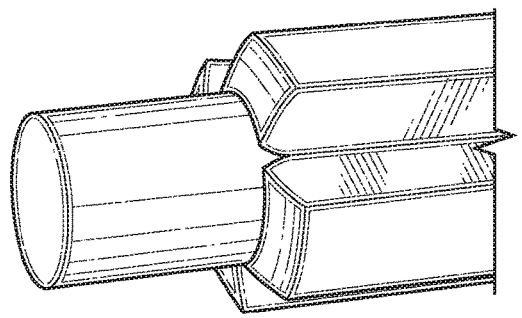
FIG. 50

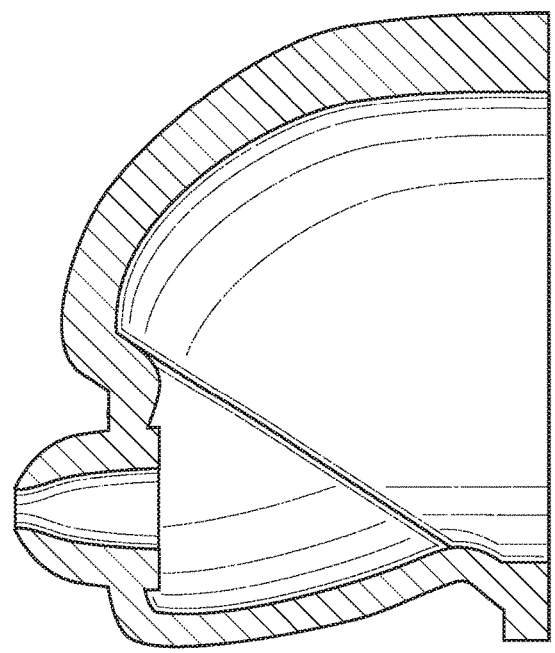
FIG. 54
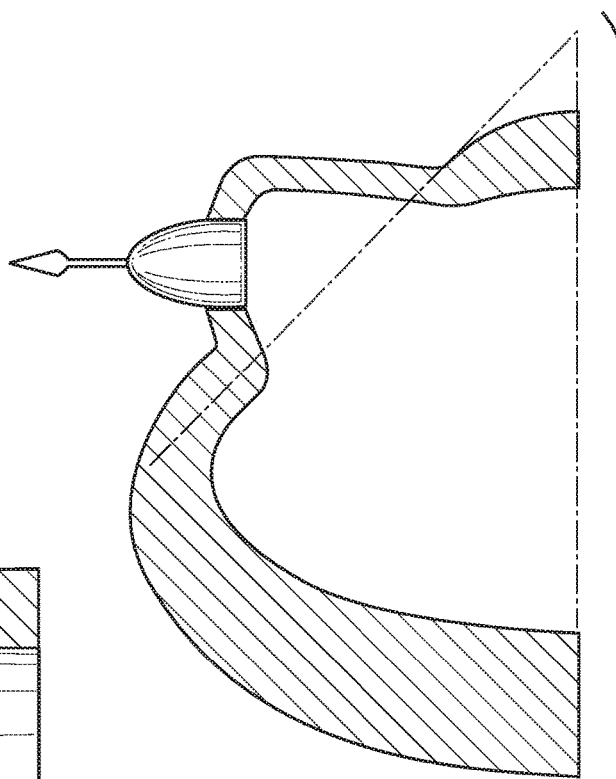
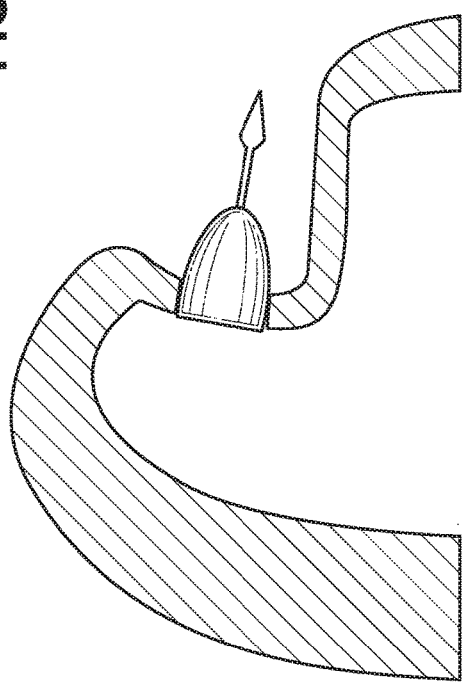
FIG. 55

ENDOSCOPE

CROSS-REFERENCE TO RELATED APPLICATION

The present application is a U.S. National Stage of International Patent App. No. PCT/US2016/061530, filed Nov. 11, 2016, and published as International Patent Pub. No. WO 2017/083648 A1 on May 18, 2017, which claims priority to U.S. Provisional Application No. 62/255,025, filed on Nov. 13, 2015. The contents of both applications are hereby incorporated by reference in their entirety.

BACKGROUND

Typical endoscopic sinus surgery is performed with endoscopes which are introduced into the anterior nose and which look either directly forward or at a fixed rigid angle. Known endoscopes merely enable visualization in a straight line at an angle to the side, preventing a surgeon from seeing around obstructions.

FIG. 1A, shows the endoscope at the opening of the maxillary sinus. The highlighted portion H of the drawing indicates the visual field theoretically possible using the present generation of rigid endoscopes, if intervening structures were removed. In FIG. 1B, the endoscope avoids the obstructing structure I, but is then located farther away from the opening, thus reducing the surgeon's view of the lateral wall L. FIG. 2 is a view of the left lateral nasal wall of a cadaver specimen. The large arrow indicates the natural maxillary ostium location. This surgically impossible orientation is from a directly laterally viewed perspective and is much more revealing than the surgeon's endoscopic view. The small arrows indicate the typical surgical incision locations presently made to access the ostium. FIG. 3 is less revealing than the surgically impossible orientation shown in FIG. 2 and shows the surgeon's best achievable endoscopic view of a normal, non-distorted, non-infected left middle meatus from an anterior approach, using current rigid endoscopes.

When the surgeon introduces a rigid angle endoscope into the nose he typically chooses between using a zero degree scope to best see where he is going or selecting an endoscope with the angle necessary to perform surgery once he arrives at the appropriate location. The surgeon might opt to use a scope with a fixed optical angle which provides only an approximation of rather than the best visualization, in order to avoid the time consuming exercise of withdrawing, disconnecting, substituting scopes, re-connecting, and replacing the scope back into position without being able to see where he is going. Using an angled scope to move forward without being able to see forward also presents challenges.

SUMMARY

The systems and methods described herein are configured to improve the surgeon's ability to visualize target structures relative to prior art devices. For example, a semi-rigid endoscope may include a shaft that is elongate along a longitudinal direction. The shaft including a shaft body that defines: A proximal rigid portion and a flexible tip that is distal to the proximal rigid portion. The flexible tip moves along a lateral direction that is perpendicular to the longitudinal direction. The flexible tip moves along a transverse direction that is perpendicular to both the longitudinal and lateral directions. The endoscope may also include at least one conduit that extends longitudinally along an internal portion of the shaft body. The internal portion may be substantially enclosed, such that the at least one conduit transfers irrigant fluid to and from the flexible tip. The endoscope may also include a baffle that directs irrigant fluid at the flexible tip and an image sensor coupled to the flexible tip. The image sensor may detect electromagnetic radiation within a field of view. The baffle may direct the irrigant fluid to clean the image sensor.

In another example, a system may include a semi-rigid endoscope having a shaft that is elongate along a longitudinal direction. The shaft may include a shaft body that defines a proximal rigid portion and a flexible tip that is distal to the proximal rigid portion. The flexible tip may be configured to move along a lateral direction and a transverse direction, wherein the lateral direction is perpendicular to the longitudinal direction, and the transverse direction perpendicular to the longitudinal and lateral directions. The system may include an image sensor disposed within the flexible tip, the image sensor configured to detect electromagnetic radiation. The system may also include a hand control electrically and mechanically coupled to the semi-rigid endoscope. The hand control may be configured to direct movement of the flexible tip along the lateral and transverse directions, and rotation of the proximal rigid portion about a longitudinal axis that is parallel to the longitudinal direction.

BRIEF DESCRIPTION OF THE DRAWINGS

FIG. 5 illustrates two sets of curvatures starting first distally at the end of the scope and then progressing serially more proximally. The upper curves show what happens when the curve progresses along the entire length at the same time. The inferiorly directed curvatures shows what happens when the curve starts at the tip and then progresses serially only after the distal-most segment has rotated the maximal amount of 15 degrees.

FIG. 6 is a composite rendering of both the continuous, equal curvature scope and the sequentially curving endoscopes' fields of view for several discontinuous angles in a single plane and demonstrates the full 360 degree coplanar viewing capability. The embodiment on the left has a single point of attachment, while the embodiment on the right has serial points of curvature.

FIG. 19 illustrates the range of motion of a scope that combines a short arc 45 degree distal tip angulation in the vertical plane with a full 180 degree long arc in the horizontal plane.

FIG. 20 illustrates the overlapping fields having complete visualization 360 degrees in all directions.

FIG. 32 illustrates the irrigation sheath bases utilizing external connections. Drawing A is a double inflow sheath attached to the endoscope. Drawing B is the doubly supplied sheath alone. Drawings C and D are the cruciform endoscope again demonstrating the orientation vane from both the front and side views. Drawing E is a singly supplied sheath. Drawing F is a cut away view of the sheath with the scope in place.

FIG. 34B is that the hole in the distal cannula is a truncated conical shape to improve focusing the jet stream of irrigation fluid. The bracket which attaches on the side wall of the outer sheath is not drawn as in FIG. 34A.

FIG. 35A is the top view of the endoscope and the sheath which does not incorporate the jet tip nozzle within the extendable cannula. The left view is the low pressure condition with the baffle redirecting fluid flow centripetally. The right view is under the high pressure condition where the cannulae have protruded forwards exposing the full stream of field irrigation fluid. Seen within the open cannulae can be noted the springs which return the cannulae to their initial retracted state.

FIG. 35B is the same view and under the same conditions as in FIG. 35A but this irrigation sheath utilizes the cannulae which incorporate the distal jet tips.

FIG. 38 illustrates on the left the inner irrigation cannula with its fenestrations. The center drawing is the isolated inflated expandable collar. The biased internal cloth is not depicted for simplicity. The right drawing is the combined irrigation sheath with a cutaway in the expanded portion of the collar to show the internal sheath and its fenestrations. The distal (top) collar is mobile and has retracted from the top of the internal sheath upon the collar's expansion. The bottom collar is fixed to the internal sheath proximally.

FIG. 39 is a top view of the irrigation tip with the cruciform endoscope in place. This modification uses a fairly rigid divertible baffle at the distal end of the channel carrying the irrigation fluid. The left drawing is under low pressure conditions and the baffles divert the fluid over the image sensor for cleaning. The right drawing is under high pressure conditions and the collar has been inflated. When inflated, the increase in collar circumference causes the distal rigid mobile portion to move proximally. This movement creates traction on the baffle forcing it to bend pulling the baffle to move out of the stream permitting field irrigation.

FIG. 40 is a similar view as in FIG. 39 but the endoscope is not in place.

Figure 1B:
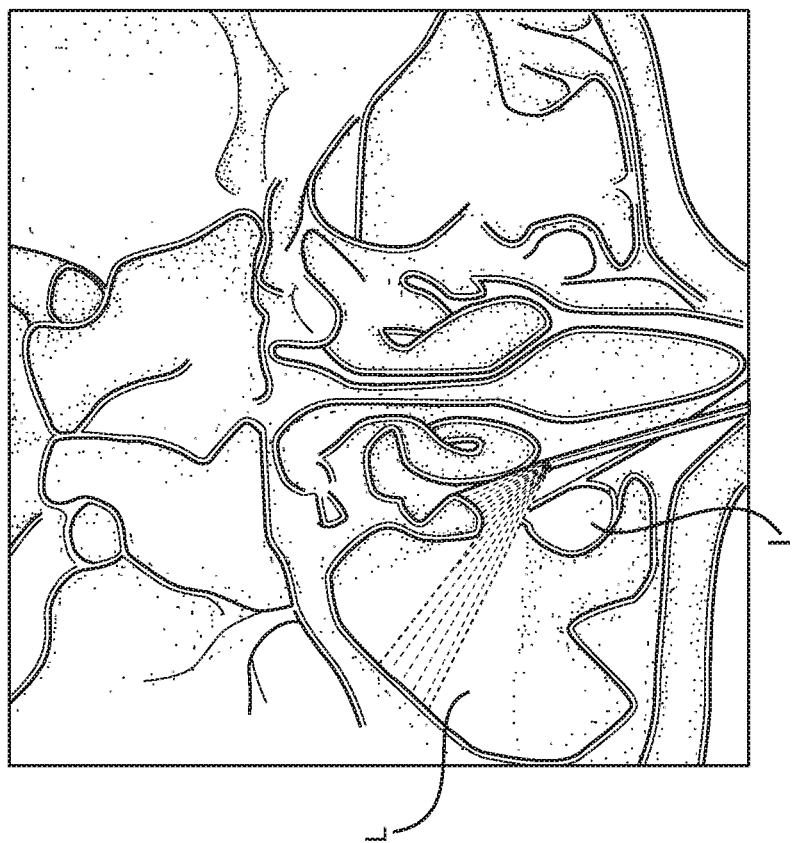
FIGS. 1A and 1B are schematics of an endoscope at the opening of the maxillary sinus.
Figure 1A:
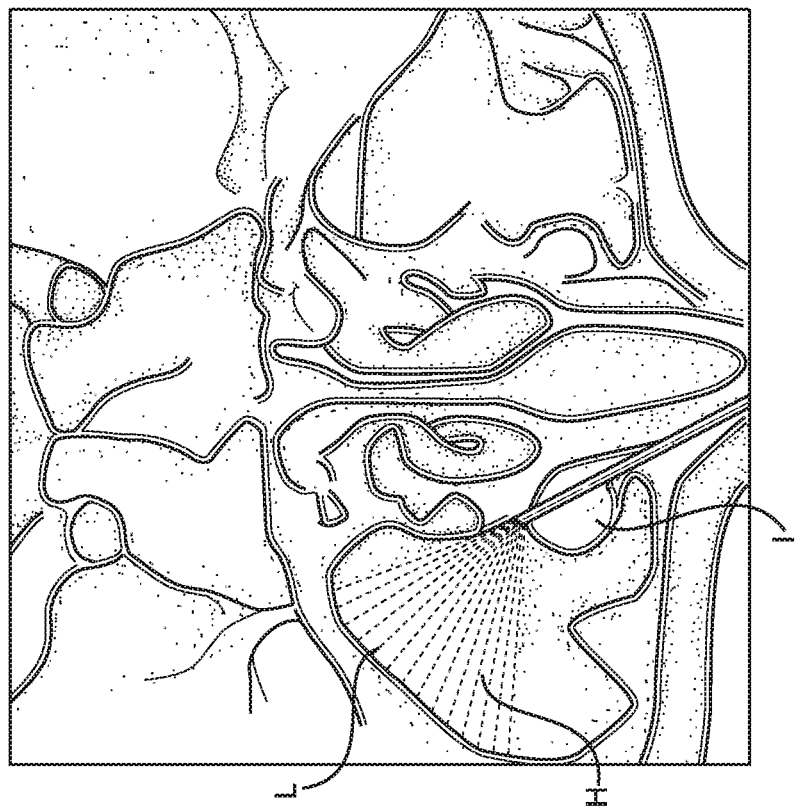
Figure 2:
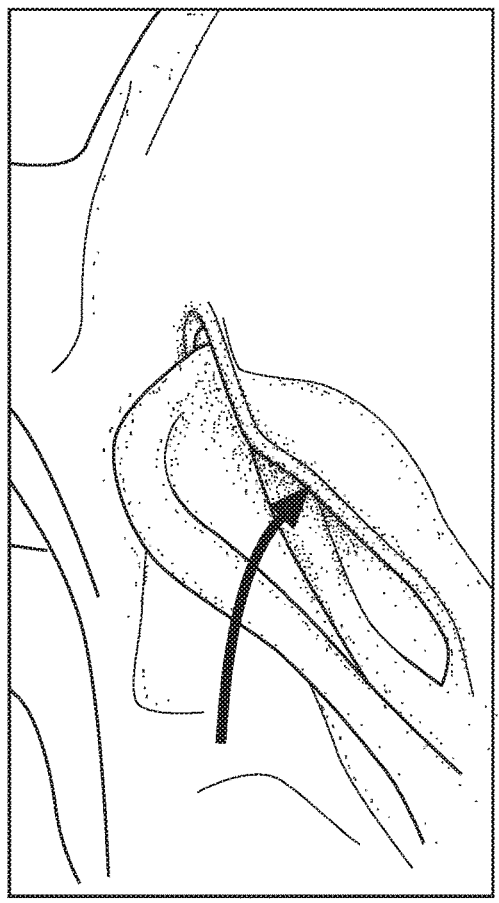
FIG. 2 is a view of the left lateral nasal wall of a cadaver specimen.
Figure 3:
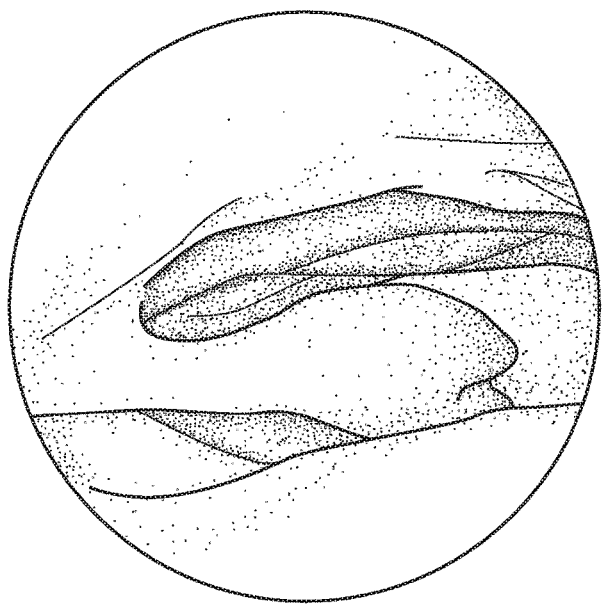
FIG. 3 shows the surgeon's best achievable endoscopic view of a normal, non-distorted, non-infected left middle meatus from an anterior approach, using current rigid endoscopes.

Under these conditions the baffle has been pulled out of the irrigation stream. The farthest right pair of drawings again illustrates the inner wall of the sheath and the separate inflated collar. The height of the collar under pressure is shorter due to its inflation. The distal edge of the collar also demonstrates the change in shape of the connecting band which attaches the baffles to the collar which is also demonstrated in FIG. 42.

FIG. 42 is a superior perspective view of the irrigation tip. The low and high pressure states are illustrated on the left and right respectively.

FIG. 43A illustrates the two cross sections of an irrigating tip baffle. The low pressure, un-inflated condition on the left and the inflated, high pressure condition on the right. The design of the collar allows fluid circulation even in the 'collapsed' condition. The higher pressure causes the collar to bow the external wall centrifugally which rotates the directing baffle and uncovers the distal ends of the irrigation channels.

FIG. 43B is a composite or superimposition of the two drawings (seen in FIG. 43A) of the un-inflated and inflated conditions. The small arrow at the top demonstrates the rotation of the baffle from its initial low pressure condition to the high pressure condition. Depicted is the minimal amount of rotation necessary to completely uncover the conduit ends. With more inflation further rotation would occur. The non-distensible threads (Depicted in FIGS. 36 and 37) could be combined with a third thread which would limit the maximal amount of distention possible. The third thread is oriented circumferentially at right angles to the long axis of the endoscope. The amount of rotation of the baffle tip depends on the amount of bowing of the side wall of the expandable collar; however, it is also dependent on where the inner side wall connects to the inner cannula. The more proximal the centripetal wall connects to the inner sheath the more rotation is possible (FIG. 44) as it has a longer lever arm of rotation.

FIG. 43C illustrates the cross sectional drawings of the two different possible flow patterns. The left drawing shows the irrigation fluid proceeding from the conduits and directly proceeding to the ejection port straight ahead. The back pressure would then push fluid into the surrounding expandable collar inflating it through the side fenestration into the inner sheath. The far right drawing demonstrates a different fluid path. The irrigation fluid proceeds longitudinally distally until it gets to the proximal extent of the collar where it is entirely diverted first into the collar chamber. The fluid then circulates within the collar confines and exits the collar back into the internal sheath through the fenestrations. This would help to equalize the delivered pressure to all exit ports. Also varying the size of the fenestrations in the side wall provides for a predictable and controllable pressure drop of the final delivered irrigation stream. This design is preferable if pressure requirements for the 'inflation' of the collar are higher than the pressure desired for irrigation of the surgical field.

Figure 44:
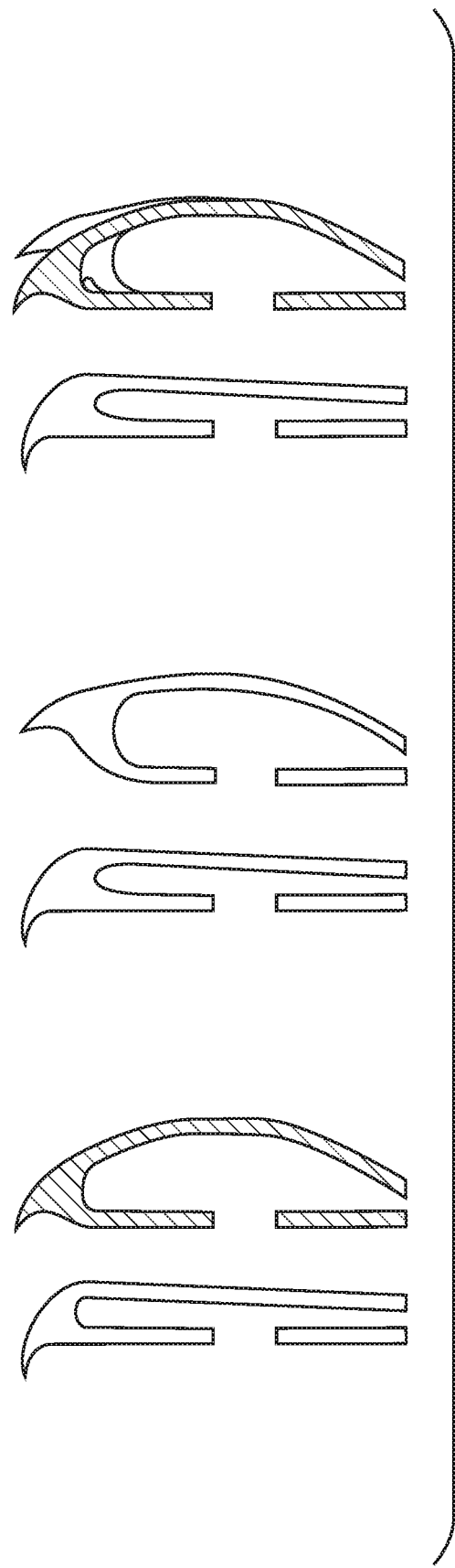

FIG. 44 illustrates the difference in the rotation possible by altering the centripetal contact point. The pair of drawings to the left is the same as depicted in FIG. 43A. The center pair has a lower, more proximal point of fixation to the inner cannula. The distal cap which is attached to the redirecting baffle has a lower arch and has more material within the cap. When it is pulled proximally and centrifugally by the hydraulic inflation of the collar, the baffle is rotated wider and is pulled proximally. The longer lever arm caused by the lower rotation point may require less tension to move the baffle out of the way. This adjustment will allow for the utilization of varying materials of different elasticity for its construction. It moves considerably more out of the way of the field irrigation stream with the same amount of collar inflation. The overlaid pair of inflated cross sections on the right demonstrates the comparison of the amount of rotation possible using the illustrated differences.

Figure 45:
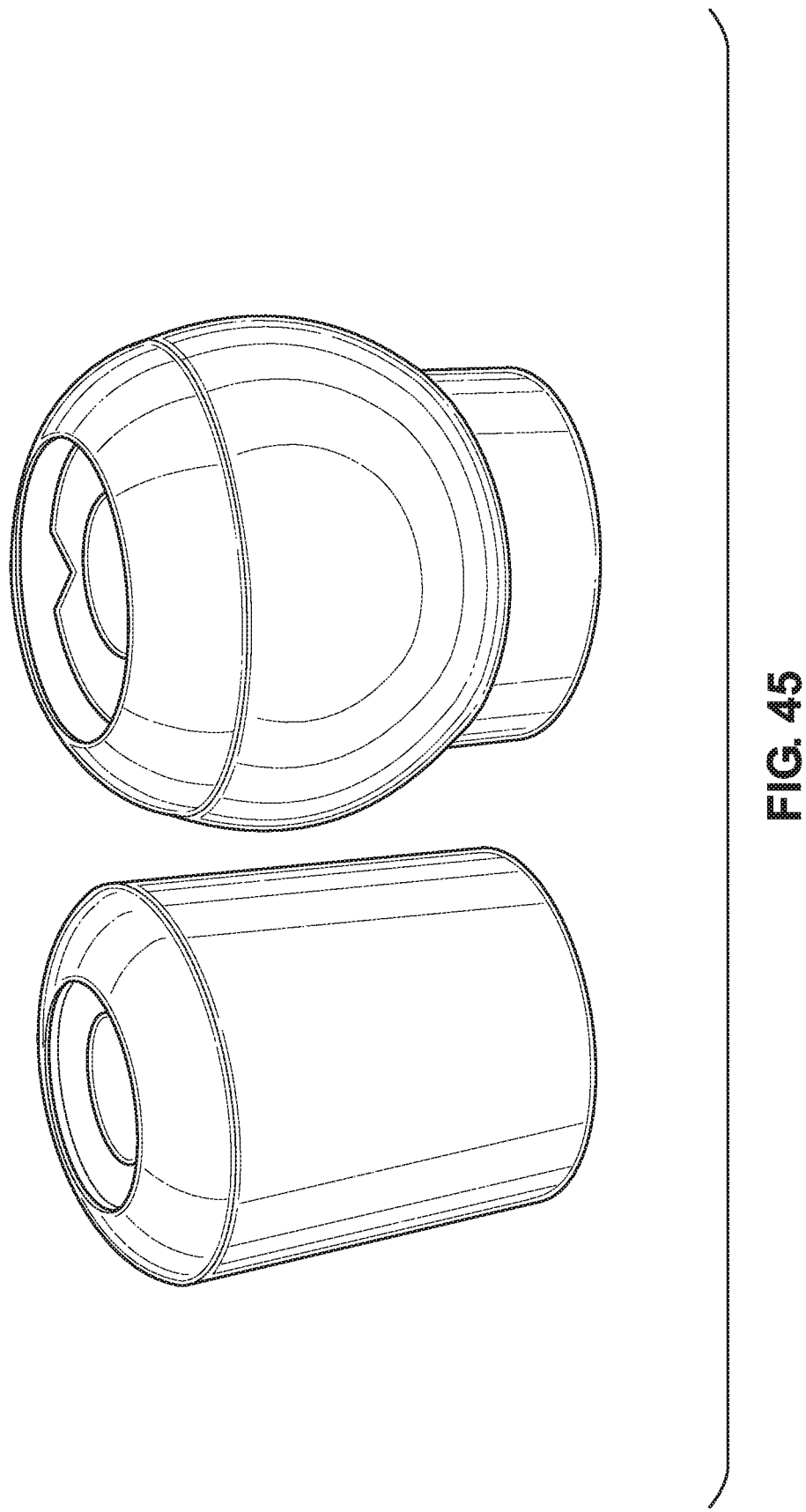

FIG. 45 depicts perspective drawings illustrating the distal tip of the irrigation sheath in the low pressure condition and the higher pressure condition.

FIGS. 46A & B illustrate the irrigation tip of FIG. 45.

Figure 47:
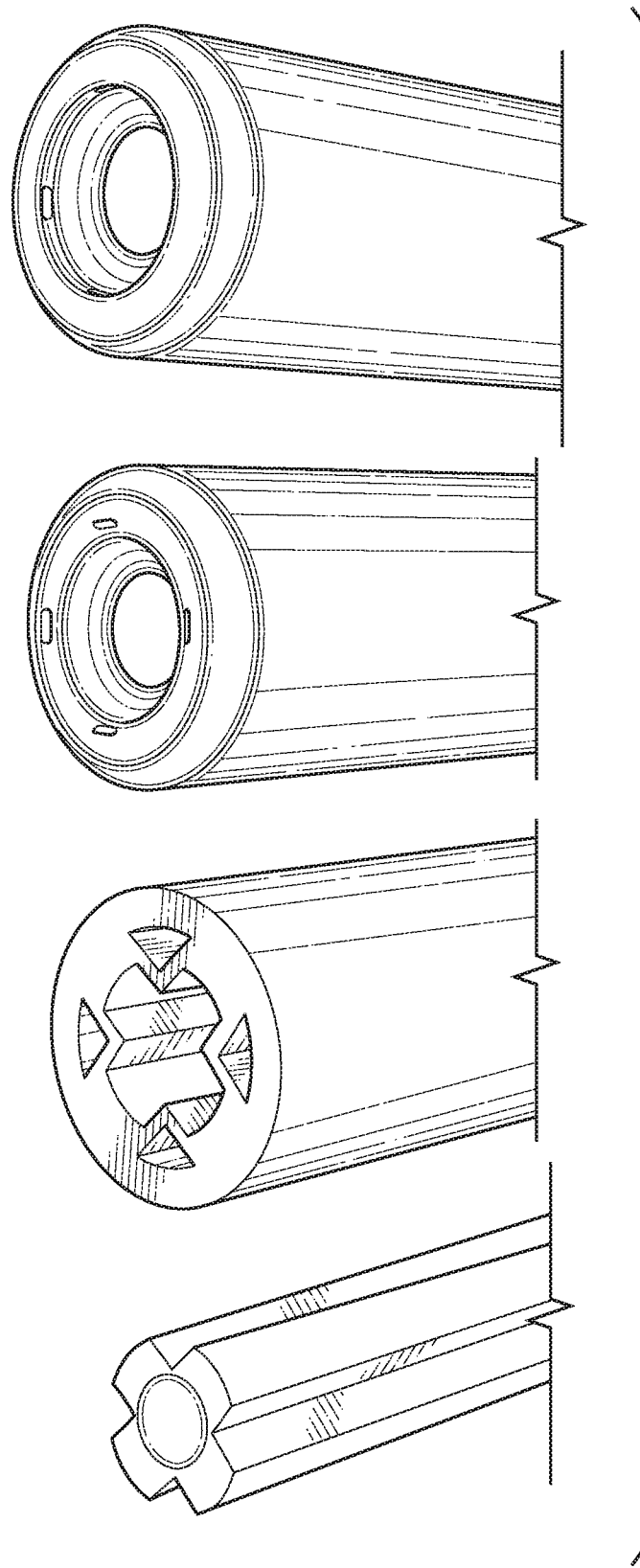

FIG. 47 illustrates on the far left a cruciform endoscope tip with exposed image sensor, the middle left the empty irrigation sheath with the internal conduits without the circumferential baffle, the middle right the assembled endoscope and sheath with its circumferential tip with nozzles in the inflated, or high pressurized condition, and the far right diagram an assembled scope and sheath but it is in the non-inflated, low pressure or non-irrigating condition.

Figure 48:
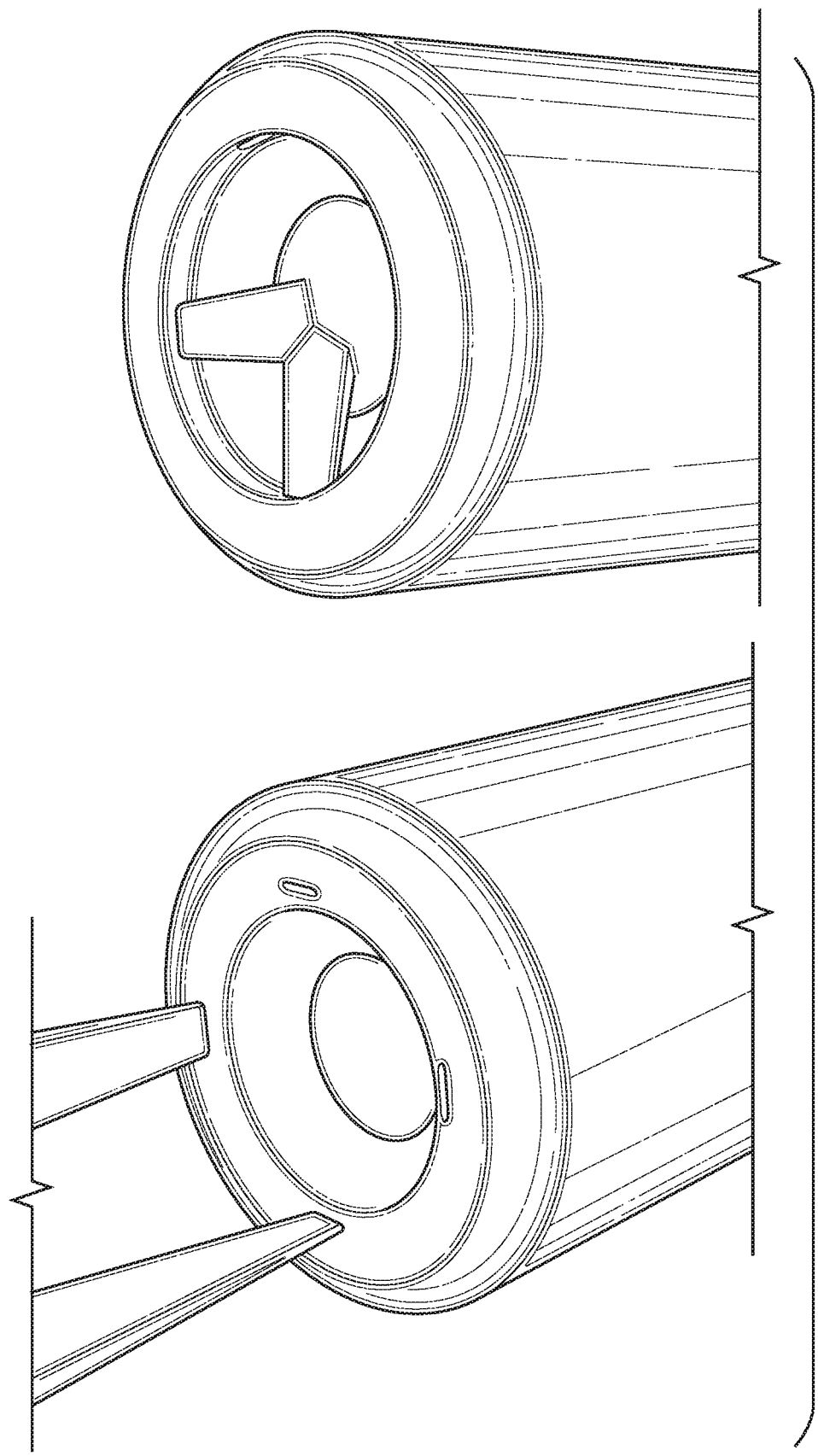

FIG. 48 illustrates a close-up view of the two conditions of the inflatable collar highly pressurized and under low pressure conditions and demonstrates the pressure's effect on the irrigation streams. The drawings schematically show two of the four irrigation streams and their orientations. The remaining two ports demonstrate their relative positions without the irrigation streams.

FIG. 49 illustrates the cross section of the circumferential irrigation channel. As noted by the drawing on the left, the channel is bulging outwards under the high pressure conditions for field irrigation. In this conformation the irrigation fluid is directed forwards. Once the pressure has been reduced, either during low pressure lens cleaning irrigations or when not irrigating at all, the channel collapses to its original relaxed state as drawn on the right. In this conformation the stream is directed towards the image sensor.

FIG. 50 illustrates two design assembles. The two drawings on the left illustrate the cruciform endoscope without the cruciform wings on the image sensor housing. The right two drawings illustrate a cylindrical endoscope. Once assembled the two scopes are indistinguishable by external visualization. The nozzles are shown in the non-pressurized condition.

Figure 51:
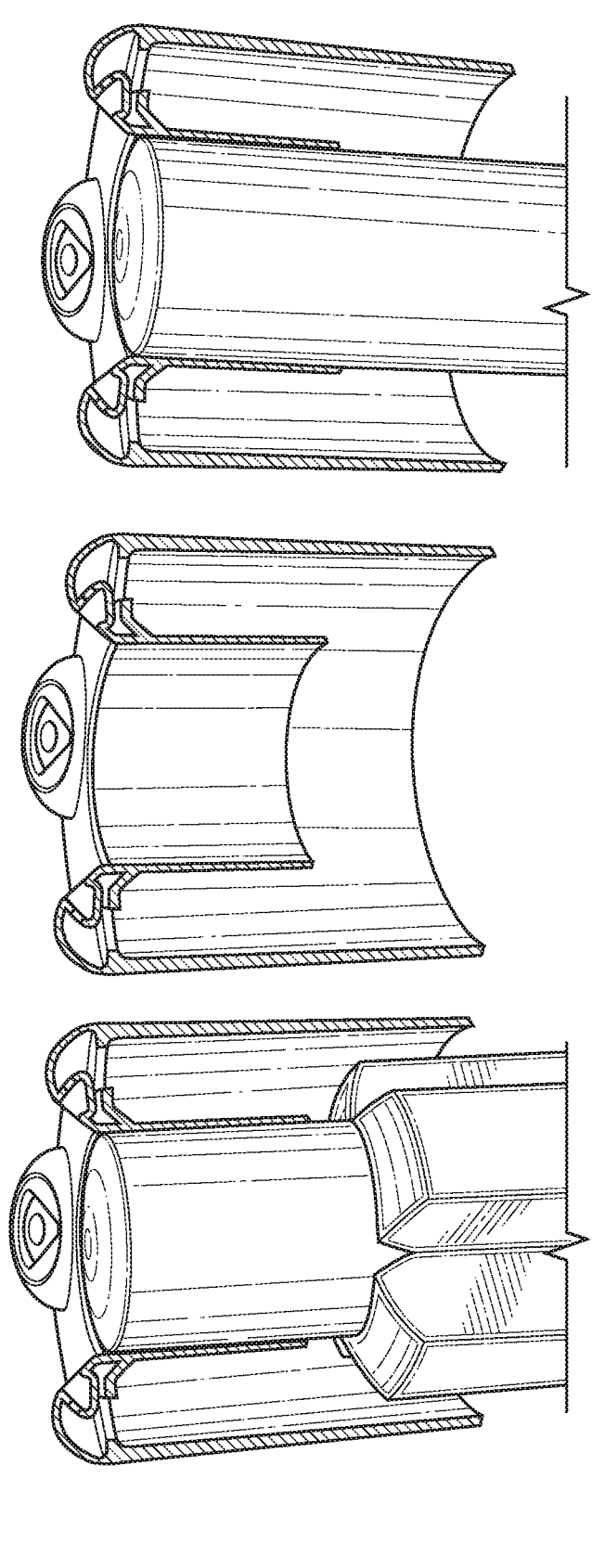
Figure 51B:
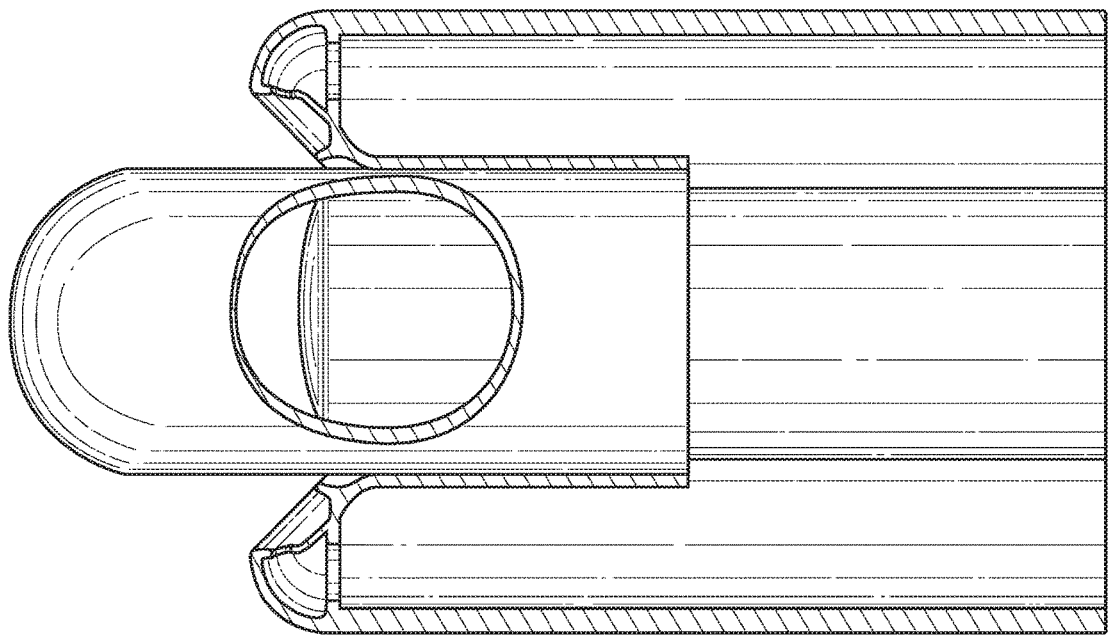

FIG. 51 illustrates cutaway views of the same two endoscope assemblies as in FIG. 50.

Figure 51A:
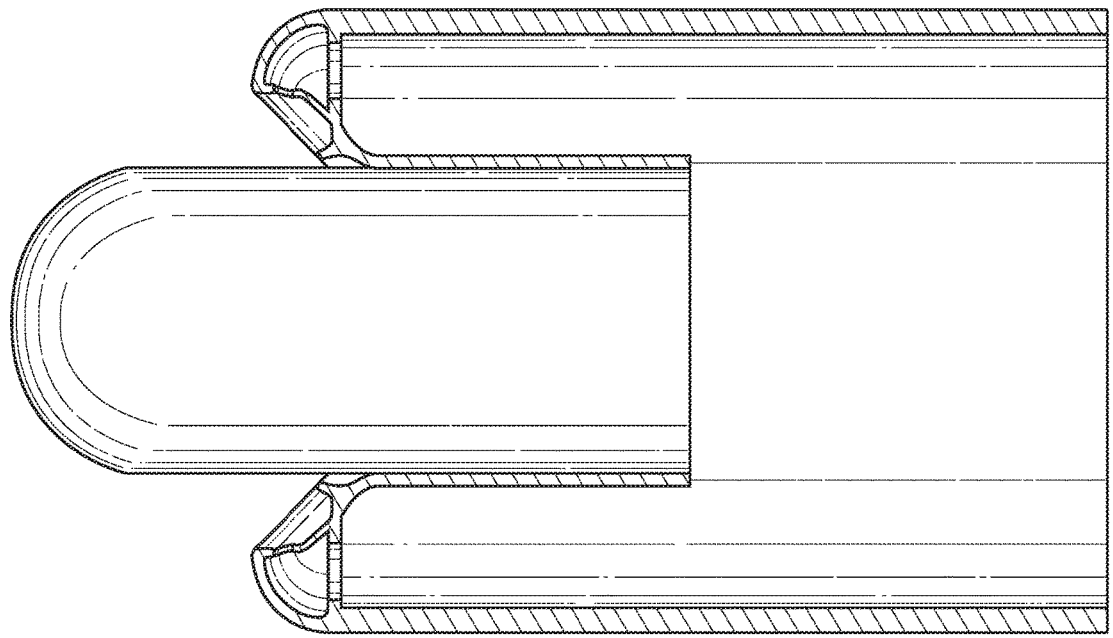

FIG. 51A and B show a self-dissolving insertion capsule stent. FIG. A illustrates the empty endoscope sheath with the capsule in place. The capsule may comprise a dissolvable material coupled to the centripetal flange, wherein the dissolvable material is initially rigid, and dissolves when it physically touches a fluid. FIG. B illustrates the sheath and capsule combination with the scope in place prior to the dissolution of the capsule. Gelatin is an example of a possible material.

Figure 52B:
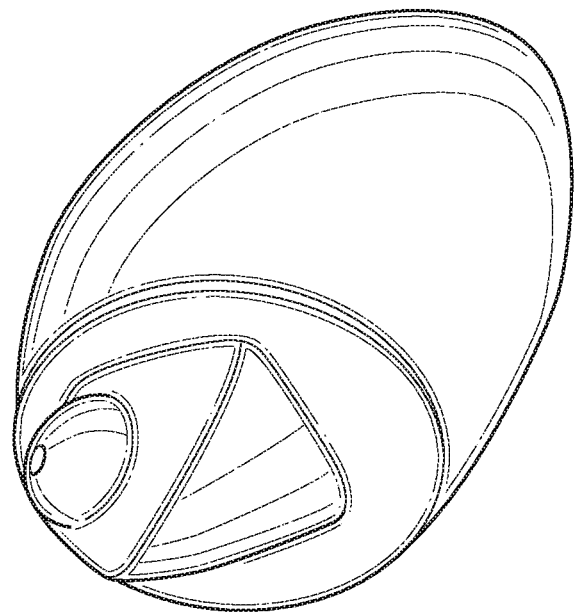
Figure 52A:
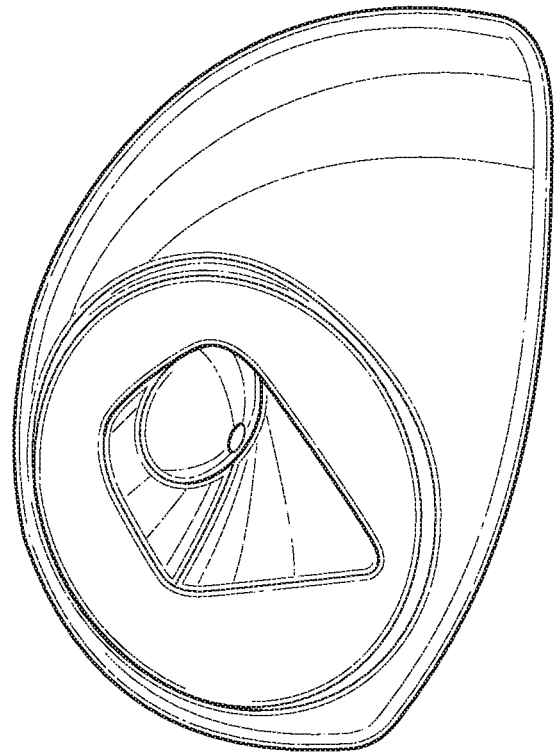

FIGS. 52A and B illustrate perspective views of the isolated exit ports. FIG. 52A is the low pressure and non-pressurized condition. FIG. 52B is the pressurized condition where the hooded nozzle has been everted. With the decreasing of fluid pressure, the everted hood reassumes its relaxed state as in FIG. 52A.

Figure 53:
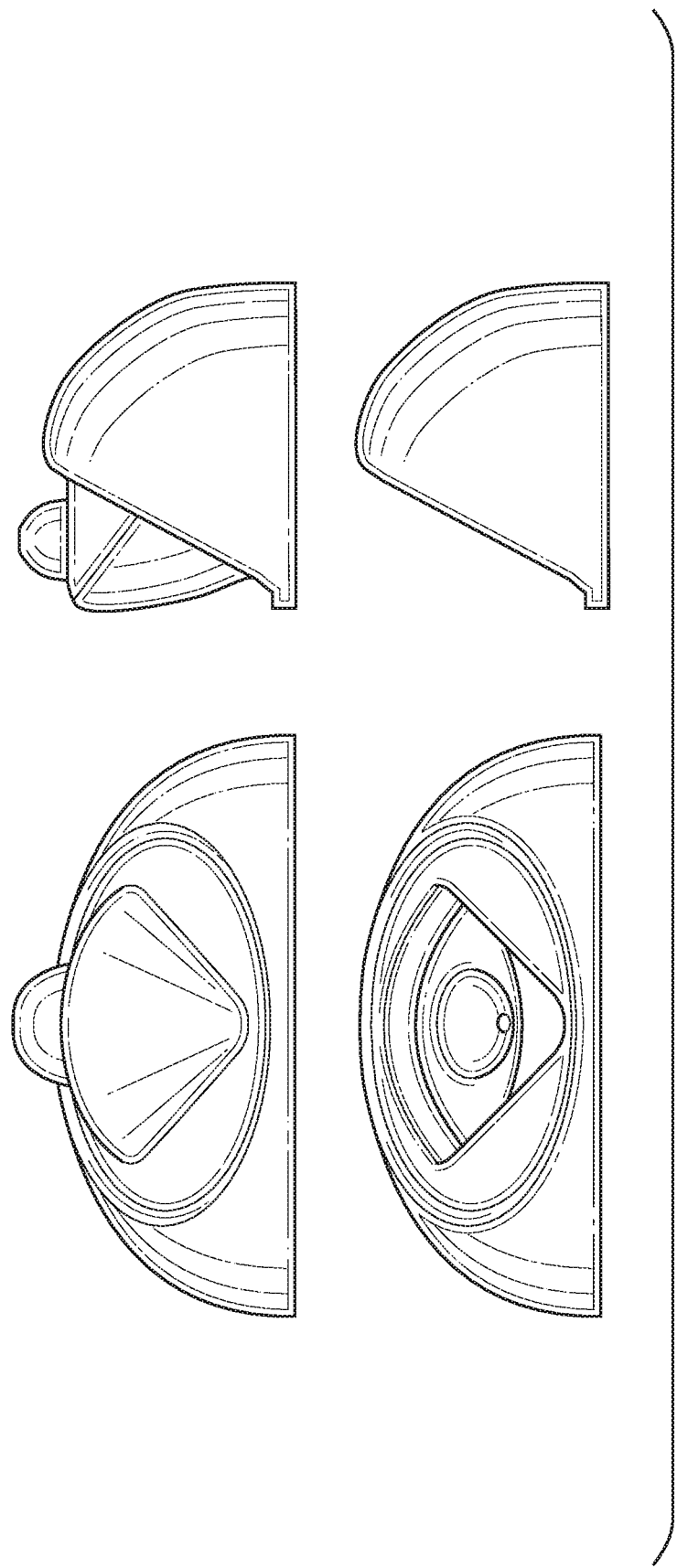

FIG. 53 illustrates the frontal and side views of the individual ejection ports. The upper pair is in the high pressure condition. The lower pair is in the low pressure or non-pressurized condition.

FIG. 54 is a cross section sagittal rendered view of the high pressurized ejection port demonstrating the forwardly directed jet nozzle and the everted hood.

FIG. 55 illustrates two schematic cross sectional views of the non-pressurized and pressurized conditions demonstrating the fluid ejection angles. Also shown is the 45 degree angle for the housing of the inverted and everted hood with its attached jet nozzle. The 45° angle is the cutoff angle for the peripheral edge of the image sensor's field of view.

Figure 56:
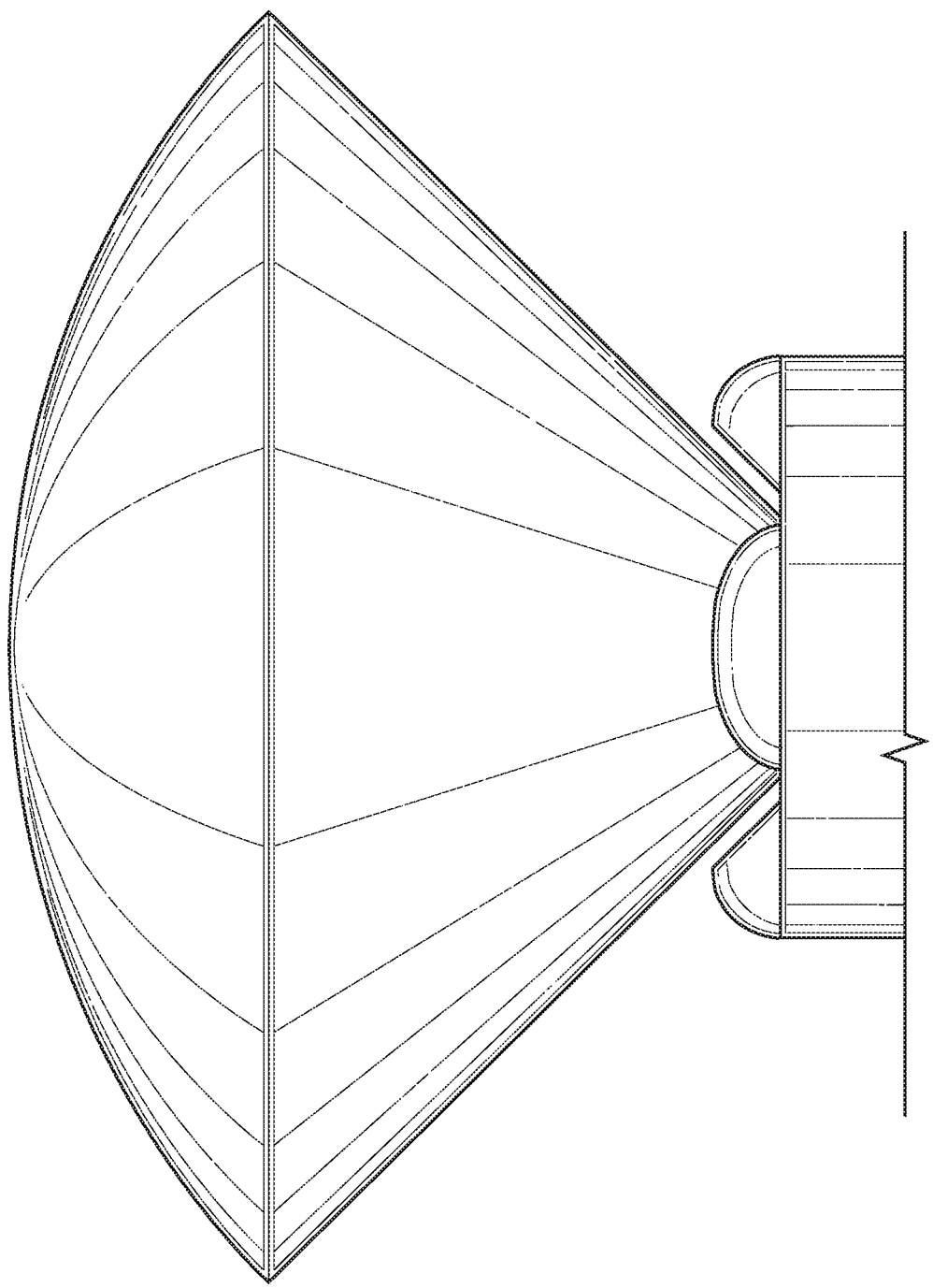
Figure 57D:
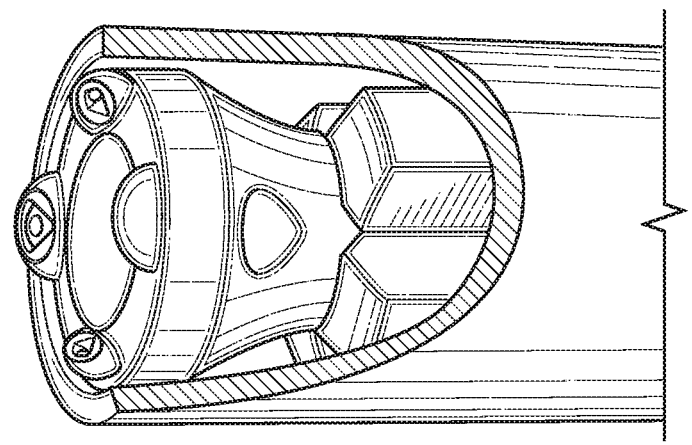
Figure 57C:
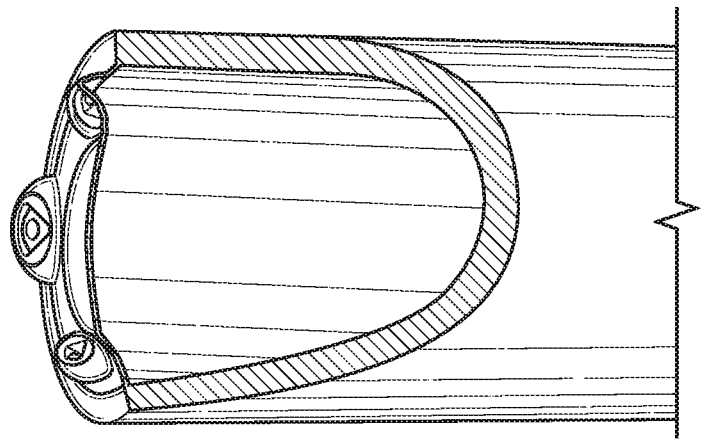
Figure 57B:
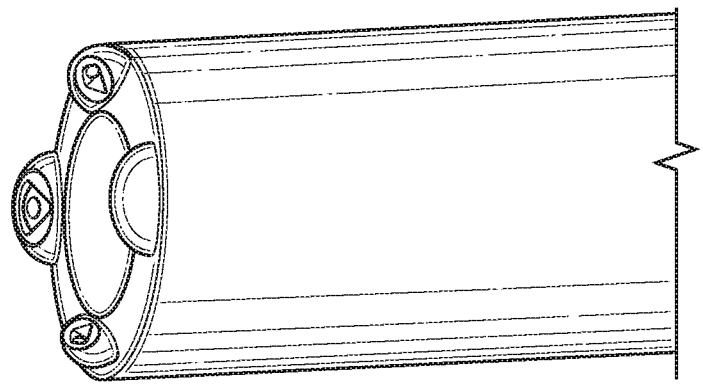
Figure 57A:
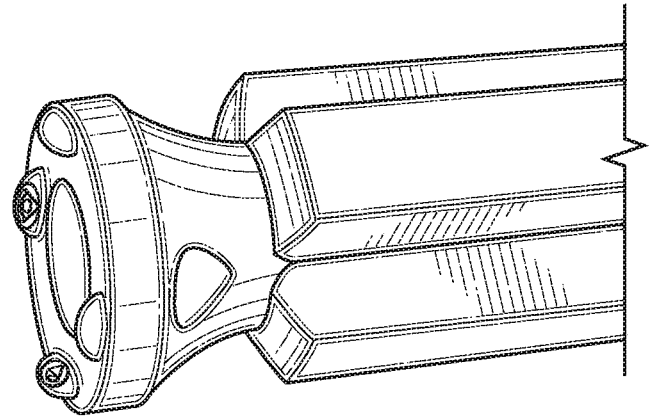

FIG. 56 illustrates the side view of the end of the irrigation sheath with the individual ejection ports. The conical area depicts the 90° visual field typical of contemporary image sensors. There may be no cutoff of the image sensor view. This is true whether the continuous circumferential or the individual ports design is utilized (in the low pressure condition).

FIG. 57 illustrates the design concept of the sealed irrigation sheath using a clear lens cover. Illustration A is the isolated semi-rigid endoscope with a distal plate. This plate supports and aligns the irrigation sheath. The distal-most actuator arms (wings) are affixed to the proximal housing for the image sensor but do not extend uninterruptedly to the tip. Distal to the arms but proximal to the plate is a space which allows for fluid redistribution and pressure equalization. Illustration B is the sealed sheath. Externally it appears the same whether there is a scope internally contained or not. Illustrated is the design for the individual everting nozzles (For nozzle detail see FIGS. 50 through 55), although the circumferential design (FIGS. 47 through 49) works equally well. Illustration C is the cut away view of the sheath without the internal endoscope. FIG. D is a cut away illustrating the endoscope in place. For illustration purposes the clear plastic lens cover is drawn segmentally to differentiate it from the rest of the sheath which need not be transparent.

Figure 58:
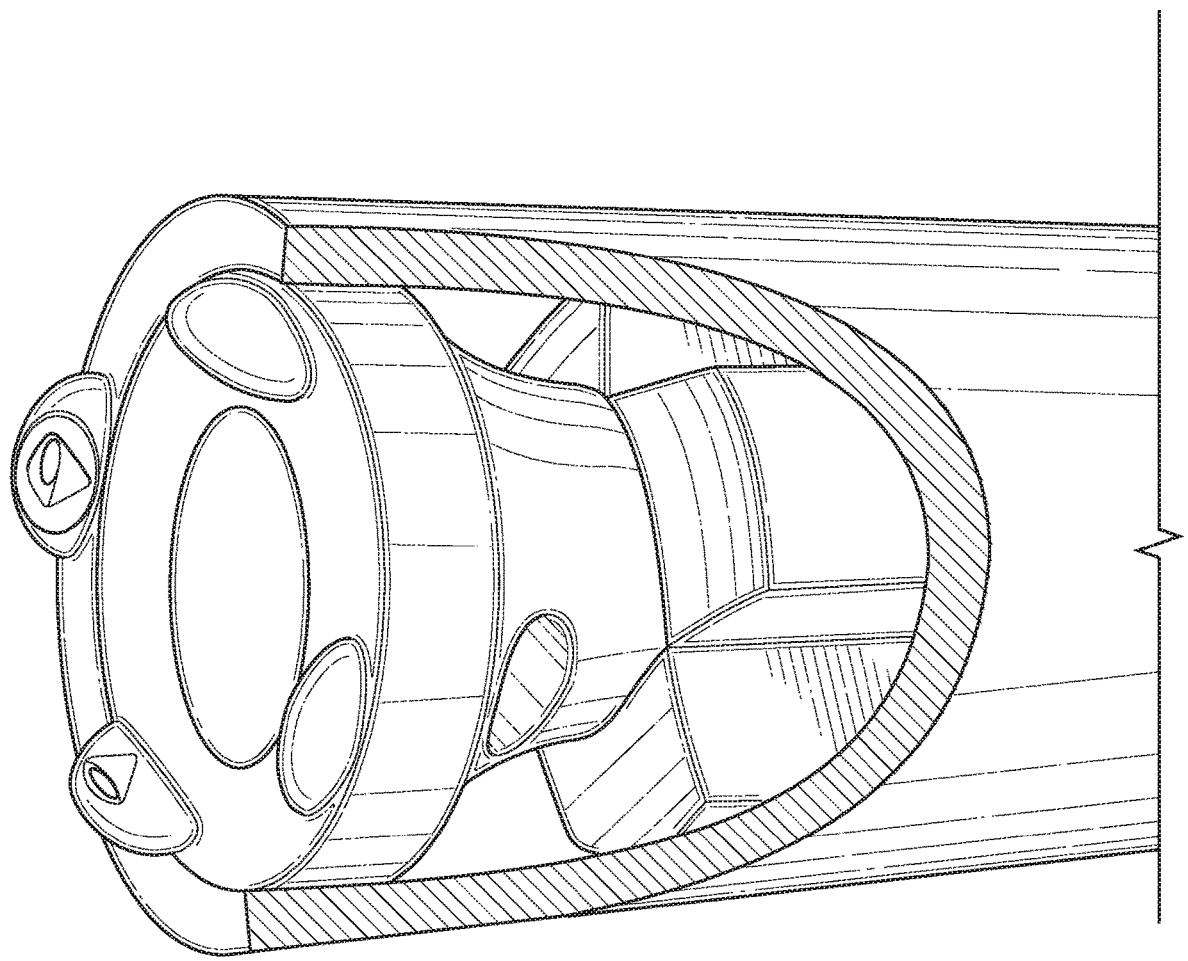

FIG. 58 is an enlarged isolated labeled view of the irrigation sheath in place with the cruciform endoscope.

Figure 59:
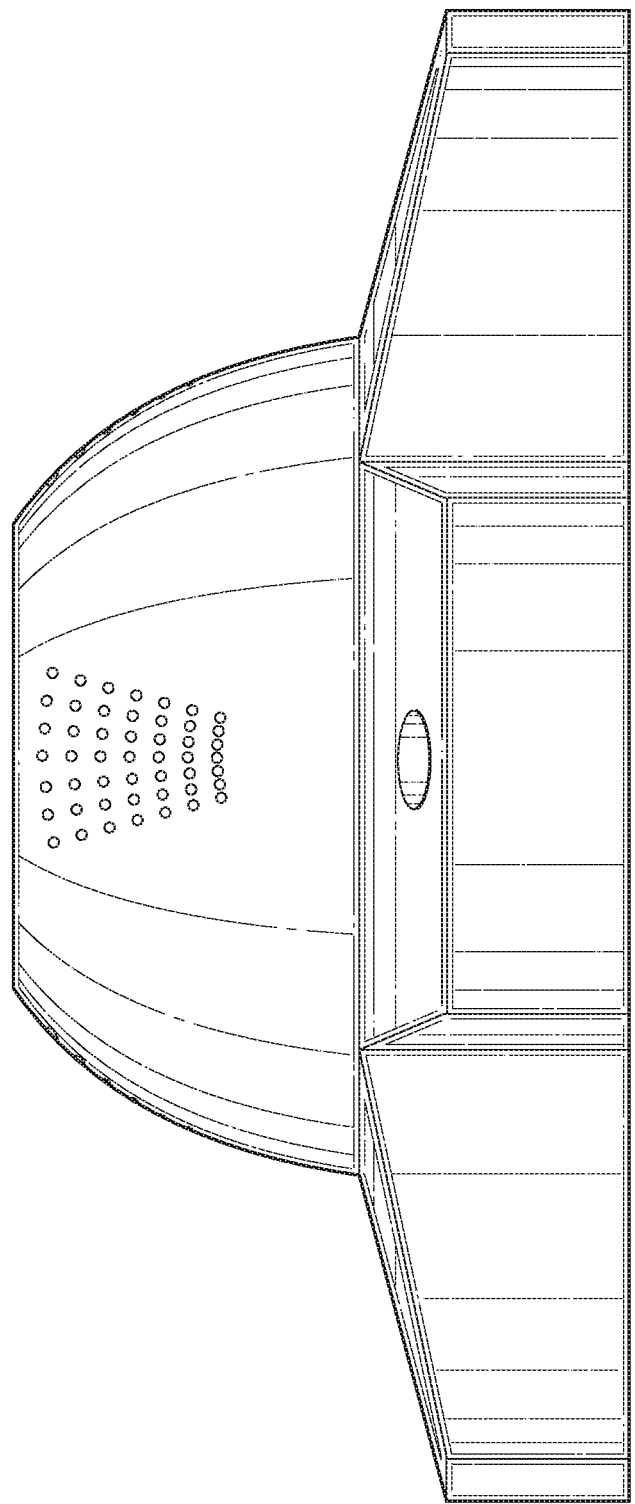

FIG. 59 illustrates a rendered external side view aspect of an individual linkage. For illustration purposes, the male convex surface is shown having inverted elongated pyramidal pits. The pits may alternatively, be arrayed on the female, concave surface. The pits are arrayed so that in every 5° arc in both the horizontal and vertical direction there is another pit. The linkage in all other ways is similar to the linkages described above in the discussion of the cruciform endoscope.

Figure 60:
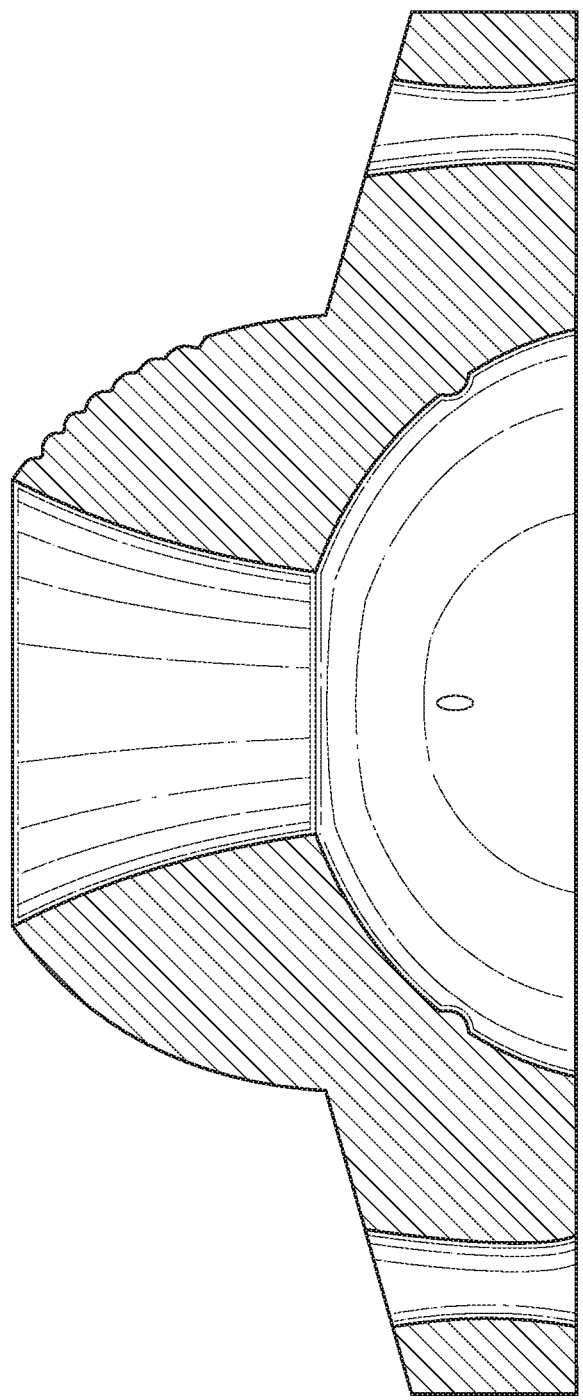

FIG. 60 illustrates a mid sagittal cut through a cruciform linkage. On its internal concave surface is shown the pyramidal appendage which will interdigitate with the external pit array once adjacent linkages are coated. Again, the appendages may be located on either the concave or convex surface.

Figure 61:
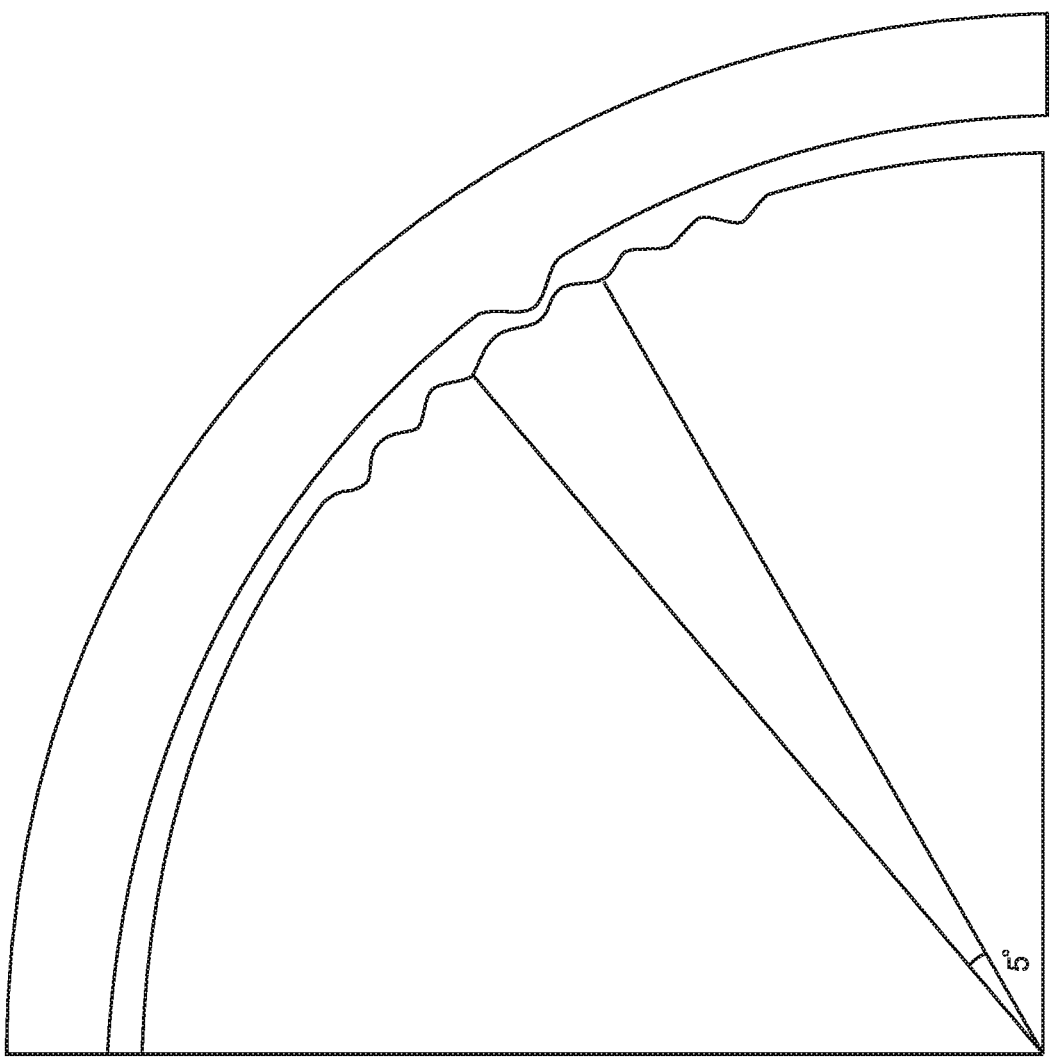

FIG. 61 is a silhouette view of male and female contact portions of the locking mechanism. There is a 5° arc distance between adjacent pits in each array. There are four arrays, one on each aspect of the linkage and are situated above the actuator arms of the linkage. Also see FIG. 59.

Figure 62A:
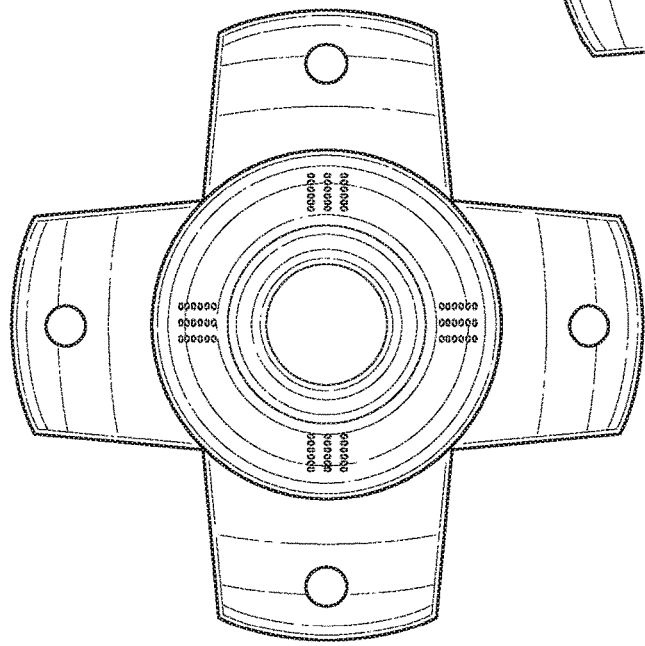

FIGS. 62A, B, & C illustrate the positioning of the appendages in the pit arrays with different angulations in differing directions. FIG. A is in the neutral or straight orientation. The "pins" are in the centrally located pits, with three empty pits in each direction from its current location. FIG. B illustrates the position of the appendages from the next most distal linkage when it is rotated 10° to the left. The "pins" have moved two holes to the left in the top and bottom arrays. The 'pins' are still in the center of the arrays in the right and left pit arrays. Figure C illustrates the position of the appendages from the next most distal linkage when it is rotated 10° to the left and 15° down. The 'pins' are now to the lowest row on the right and left arrays indicating the downwards 15° rotation. They are still in the second to the last rows to the left in the top and bottom arrays indicating 10° leftwards rotation.

FIGS. 63A through D illustrate the exaggerated motion of the concave portion of the locking mechanism as it contacts and locks with the convex portion. In the illustration only the pit array portion of the mechanism is shown so that both sides of the matched pits and appendages can be seen more easily. The centripetal surface of both the appendage and the pit are parallel not only to each other but also to the line of travel for the concave half of the mechanism. This permits smooth locking for all angles of rotation. The drawings exaggerate the amount of motion for illustrative reasons. The pyramidal shapes facilitate the alignment of the pit and appendage as only the tip of the appendage engage the outer limits of the pit. As the two halves are drawn together their shapes engage them to be more intimately aligned. Upon release of tension and the application of a rotational force, the pyramidal contours also allow easy disengagement and rotation.

Figure 64:
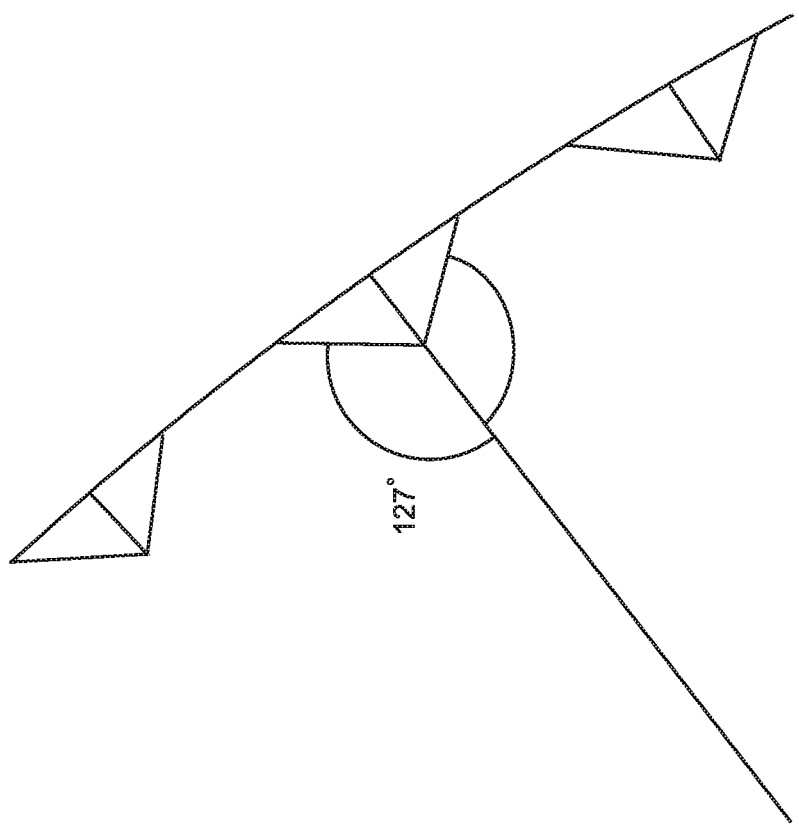

FIG. 64 is a magnified view illustrating the 53° angle on each side of the pyramidal pit of the convex aspect of the locking device. The matching appendage is the same shape but slightly larger. The noted 127° is the complimentary angle and is labeled for simplicity.

Figure 65:
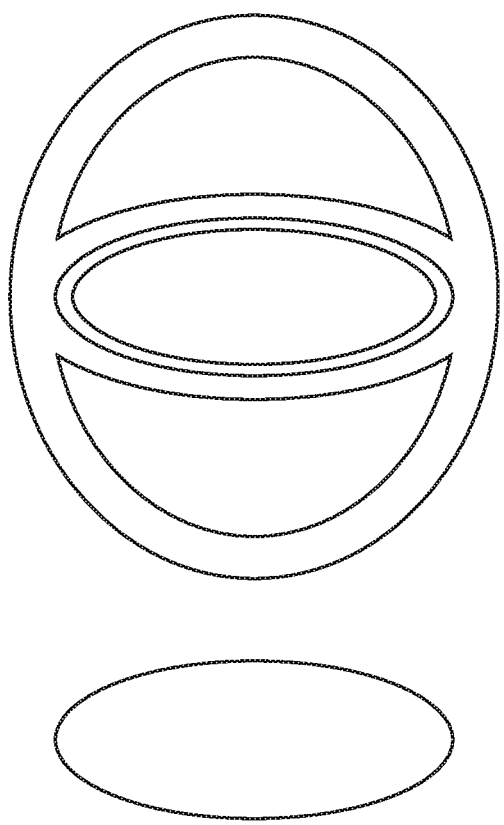

FIG. 65 is a simplified drawing indicating the orientation of a coplanar endoscope alone on the left and the endoscope within the irrigation sheath on the right.

Figure 66:
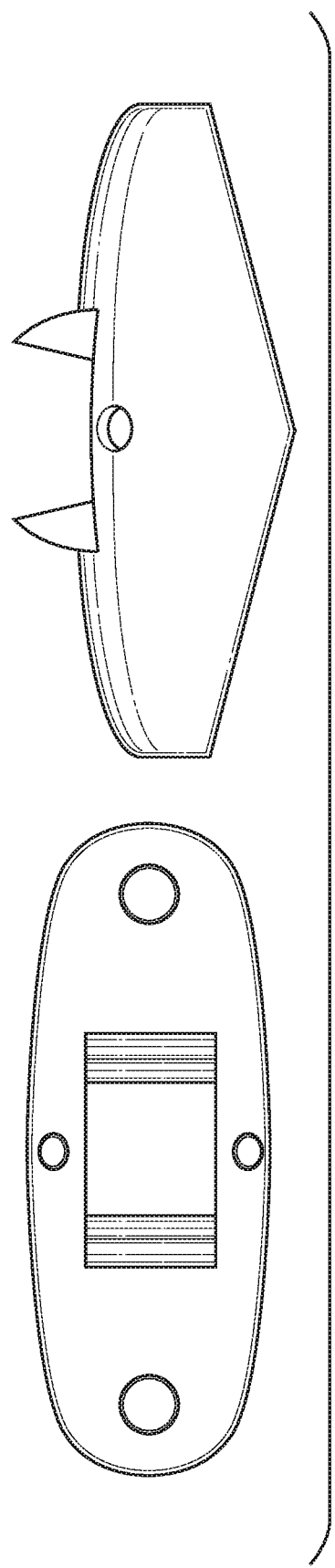

FIG. 66 is a detailed view of the two directional linkages with the optional holes for the extra guide wires. These wires allow for increased tension to lock the endoscope in position by increasing friction between linkages. The extra holes are in the middle of the linkage. Determination for their necessity will depend on the stability of the endoscope while in the locked condition.

Figure 67:
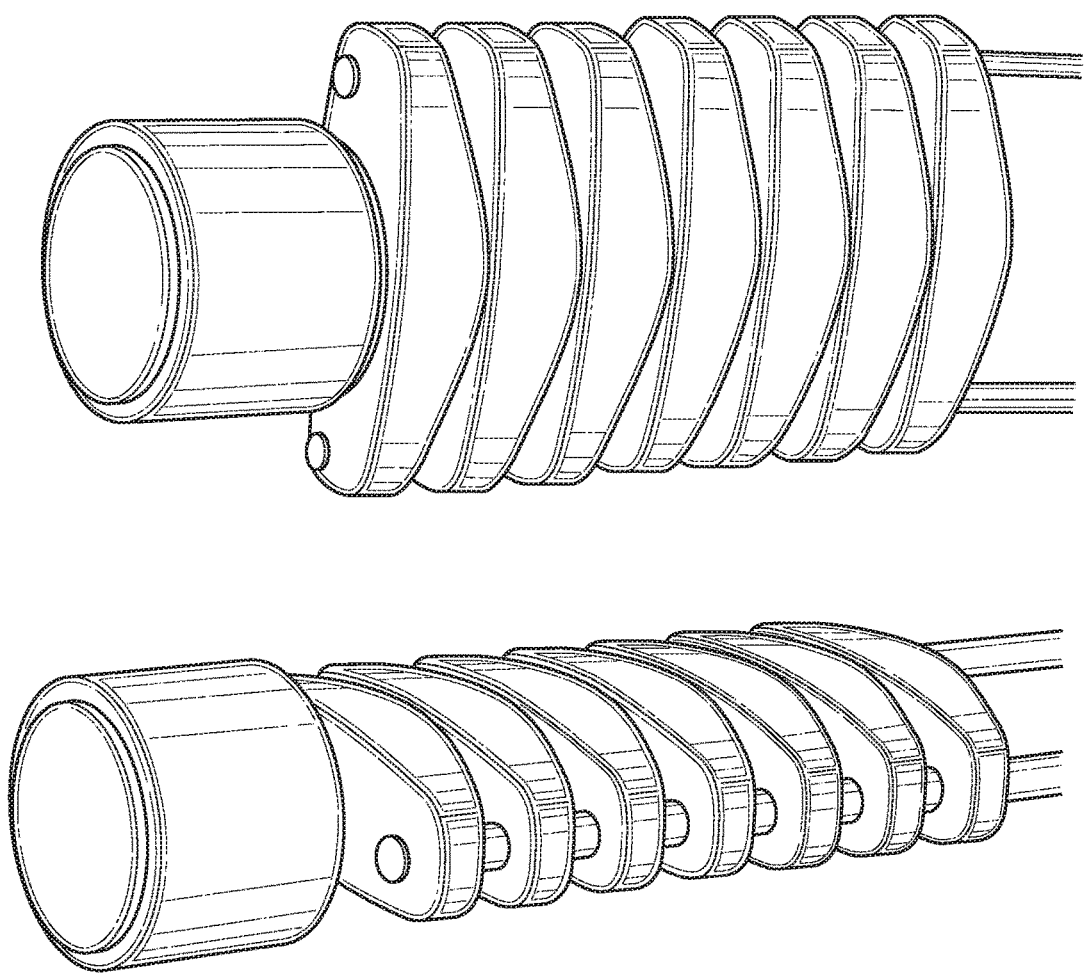

FIG. 67 is a skeletonized view of the assembled two directional endoscope without the internal flexible sheath. The guide wires which control curvature are in place but the extra possible tensioning wires are not apparent. This scope is designed to curve sequentially from distal to proximal.

Figure 68:
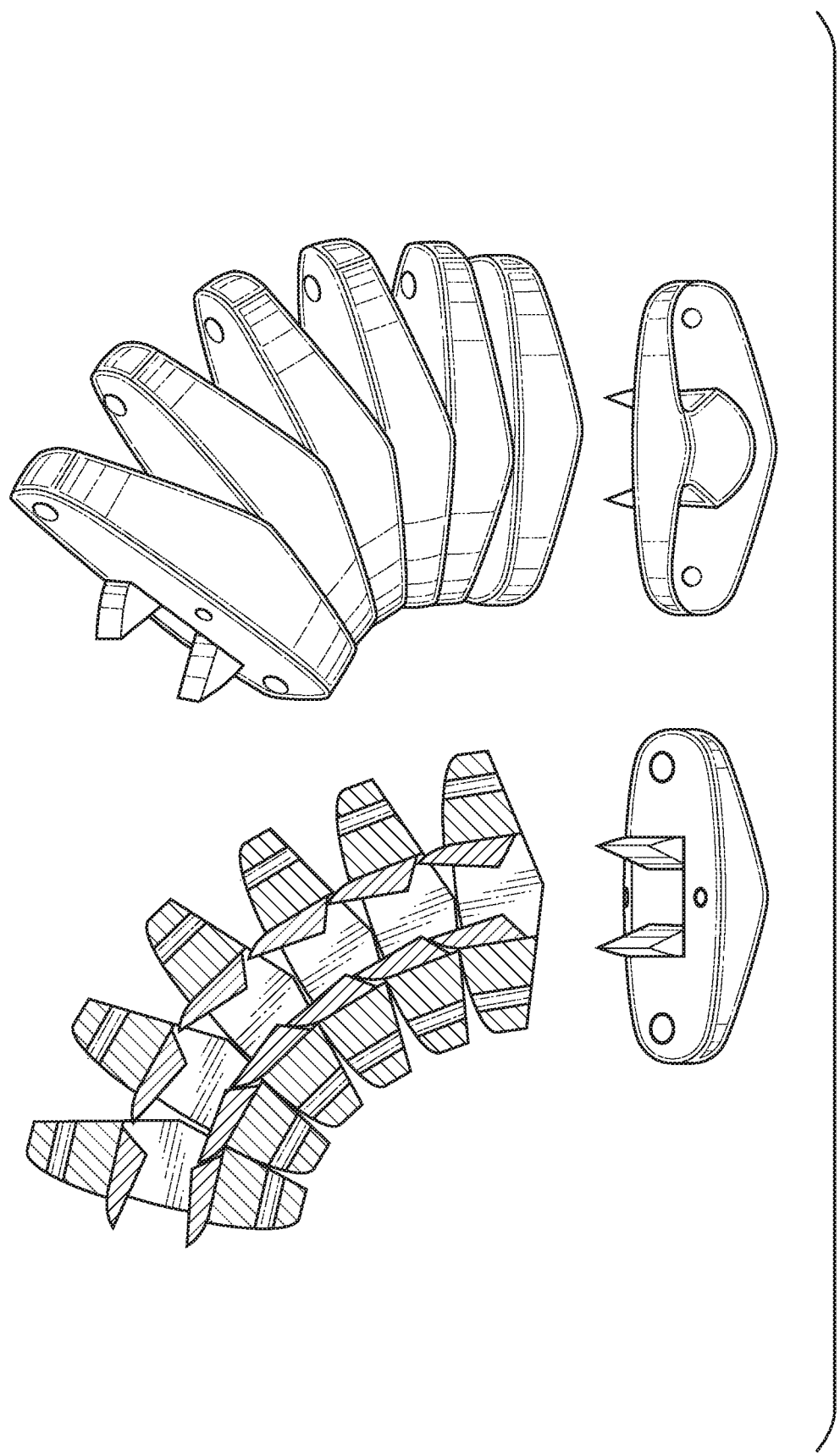

FIG. 68 illustrates the two directional endoscope maximally curving 15° per linkage. On the left is a split mid sagittal view. Each linkage rotates on a hemi-cylindrical prominence projecting off of the lower linkage. The upper linkage encases the cylinder on either end as well as 'rides' on the top. This adds to the stability of the design. The right drawing is the external view. The bottom illustrates a top and side view of an individual linkage. This embodiment does not have the extra tensioning wire holes in contrast with FIG. 66.

Figure 69:
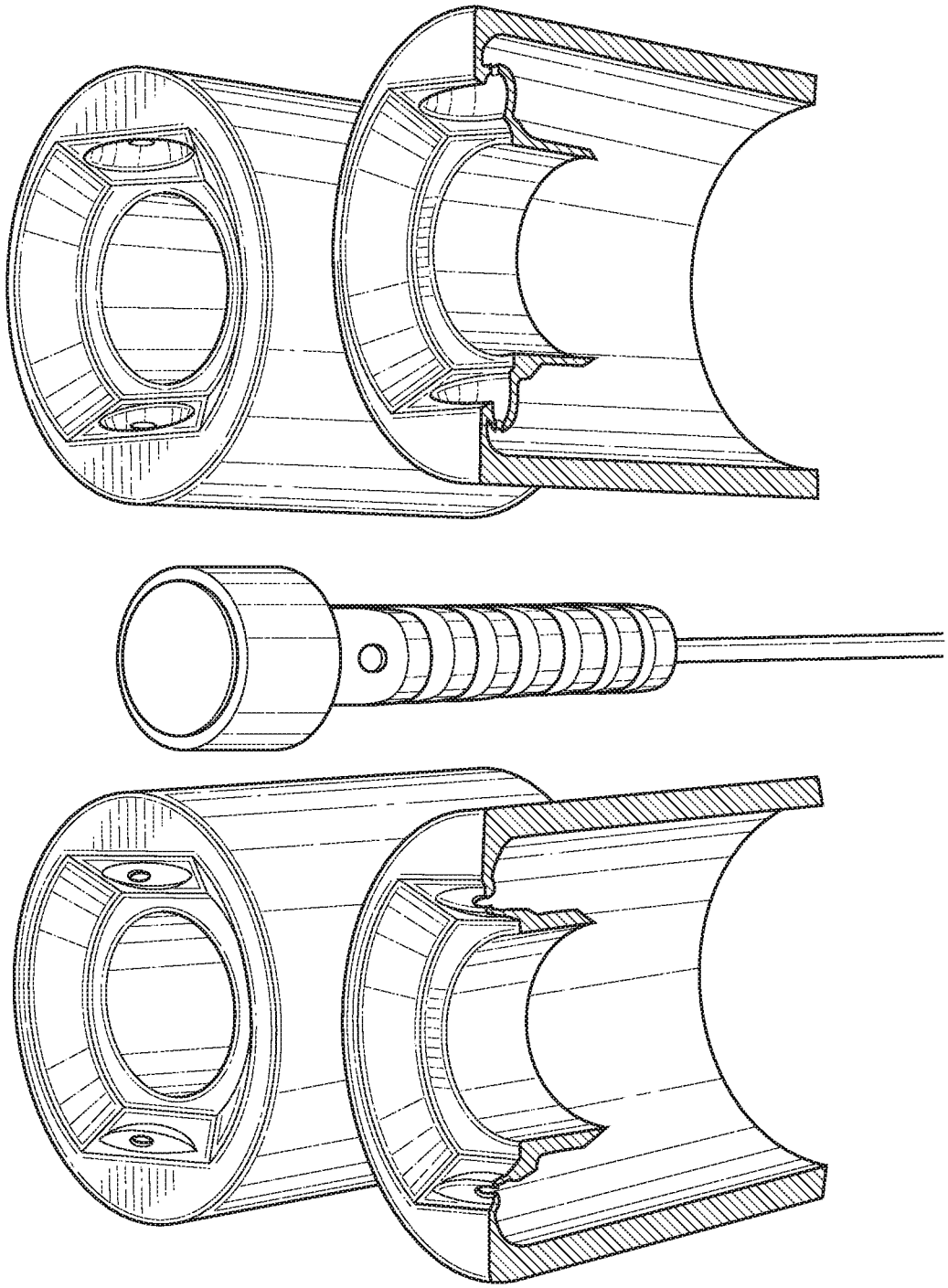

FIG. 69 illustrates the orientation of the two directional endoscope and the irrigation sheath. The scope's elliptical long axis is at right angles to the sheath's.

Figure 70:
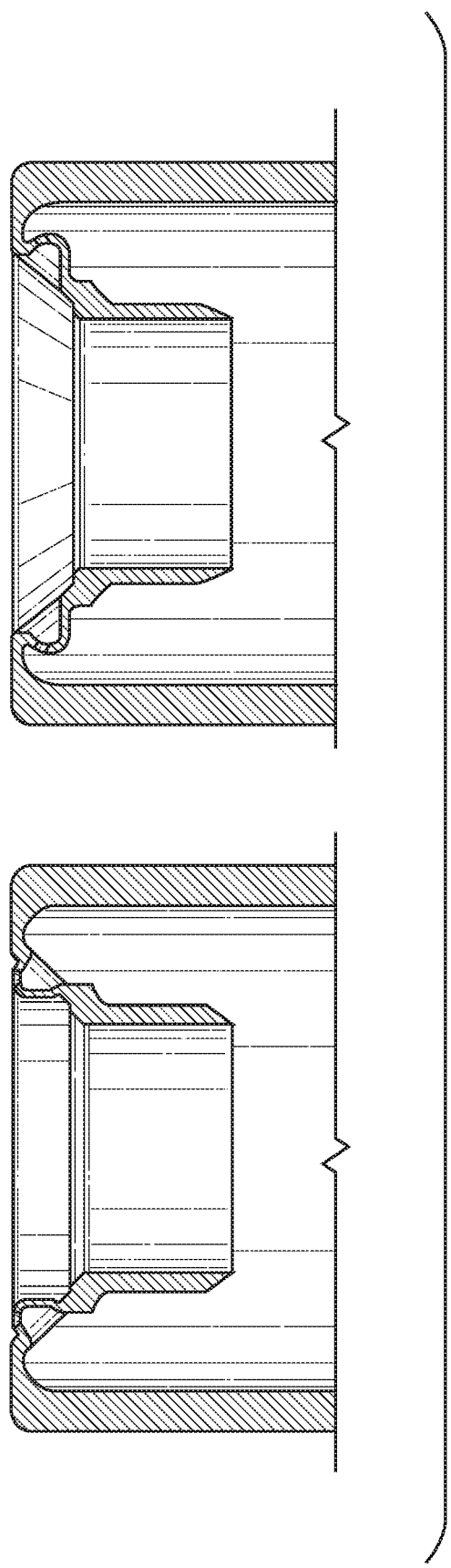

FIG. 70 is a sagittal cross section of the two directional endoscope sheath. The left illustration is the pressurized condition where the irrigation stream is directed towards the surgical field and the ports are everted. The right illustration is in the baseline or low pressure condition. Any irrigation in this configuration would direct the irrigation streams centripetally towards the image sensor for cleaning. Its design is similar to Irrigation Design F as described in sections pertaining to the cruciform scope in FIGS. 47 through 49. The centripetal flange is designed to be self-sealing and its placement aided by the gelatin stent also described above. The 90° field of view typical of the image sensor is not encroached upon by the sheath and its ejection ports.

DETAILED DESCRIPTION OF ILLUSTRATIVE EMBODIMENTS

Figure 21:
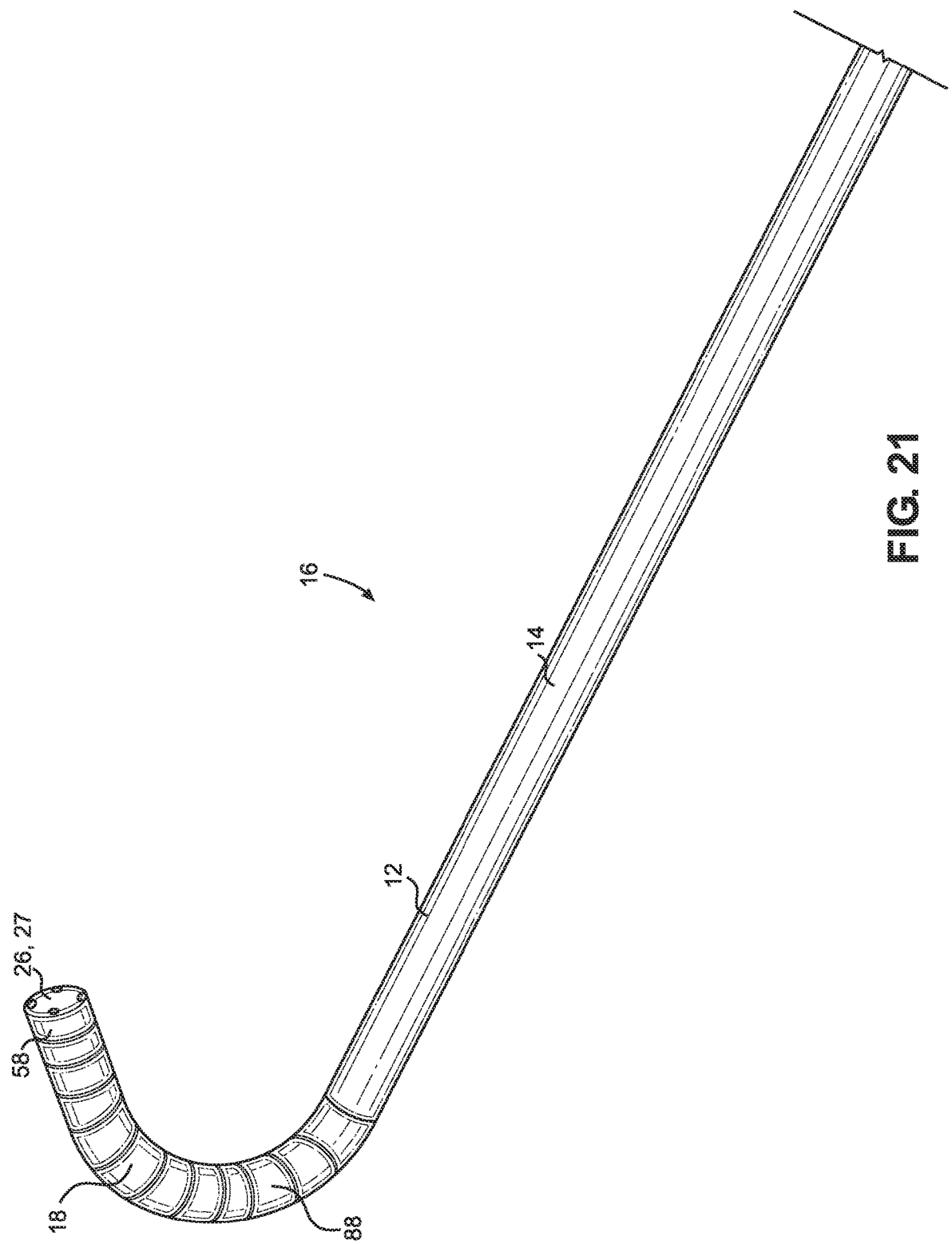
FIG. 21 is a proof-of-concept design of a semi-rigid endoscope.
Figure 22B:
FIGS. 22A and 22B illustrate a semi rigid endoscope within the maxillary sinus cavity.
Figure 22A:
Figure 23:
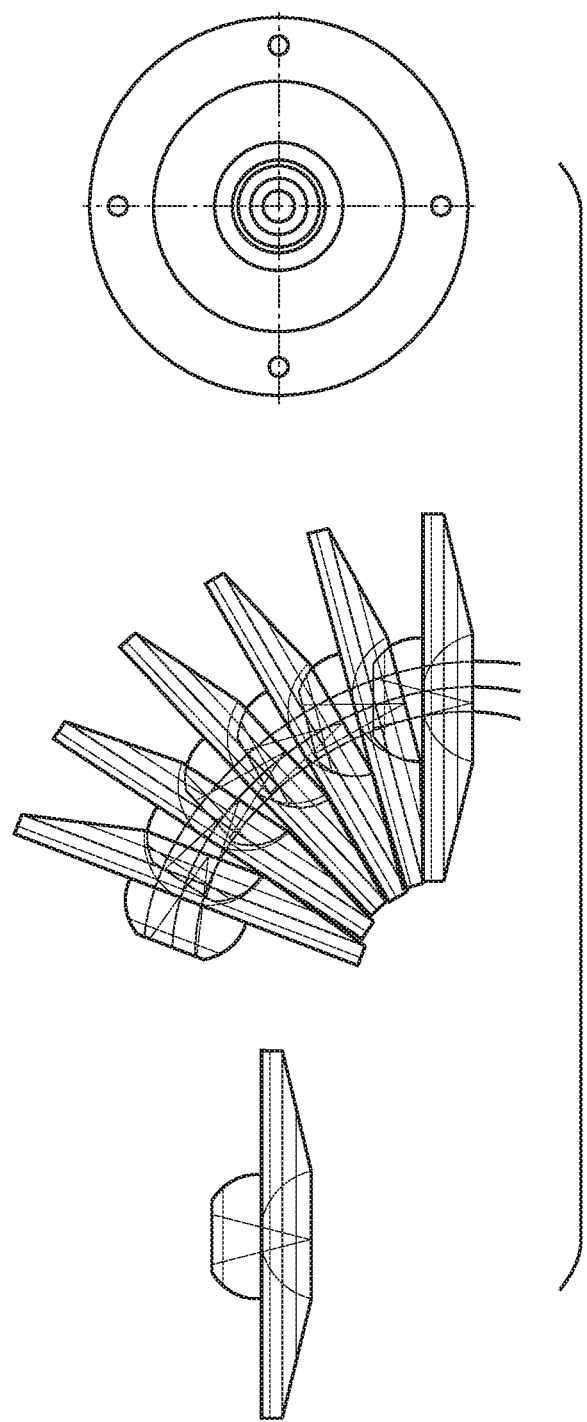
FIG. 23 is an enlarged, isolated view of linkages having a deep ball and socket design; the tendons which direct it will stabilize the endoscope even at its maximum curvature.
Figure 24:
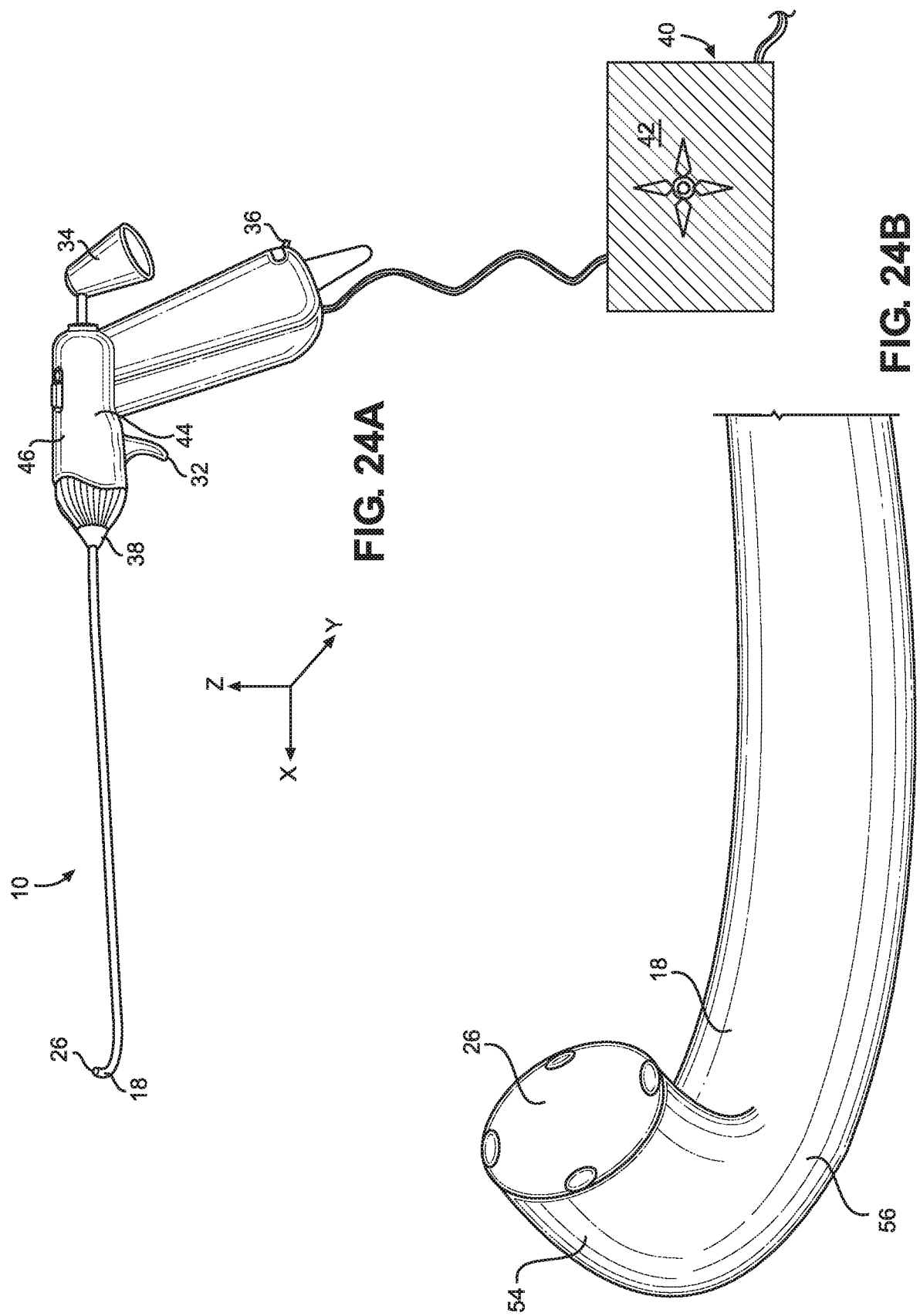
FIG. 24A is a schematic of a semi-rigid endoscope-having both an irrigation input and output port.
FIG. 24B is a schematic of the semi-rigid endoscope shown in FIG. 24A magnified to show the tip.

With reference to FIGS. 21, 24A, and 24B, a semi-rigid endoscope 10 that may be configured to visualize and/or perform surgery on an interior region of the body, e.g., head and neck. Semi-rigid endoscope 10 includes a shaft 12 that is elongate along a longitudinal direction X. The shaft 12 includes a shaft body 14 that defines a proximal rigid portion 16. Shaft body 14 may have an outside diameter of from about 4 to about 8 mm. The shaft body further defines a flexible tip 18 that is distal to the proximal rigid portion 16. The flexible tip 18 is configured to move relative to the longitudinal direction in both a lateral direction Y that is perpendicular to the longitudinal direction and a transverse direction Z that is perpendicular to both the longitudinal and lateral directions. Specifically, the flexible tip 18 may be configured to flex along the lateral direction Y and the transverse direction Z. Proximal rigid portion 16 may also be configured to rotate axially about a longitudinal axis that is parallel to the longitudinal direction X.

Figure 26:
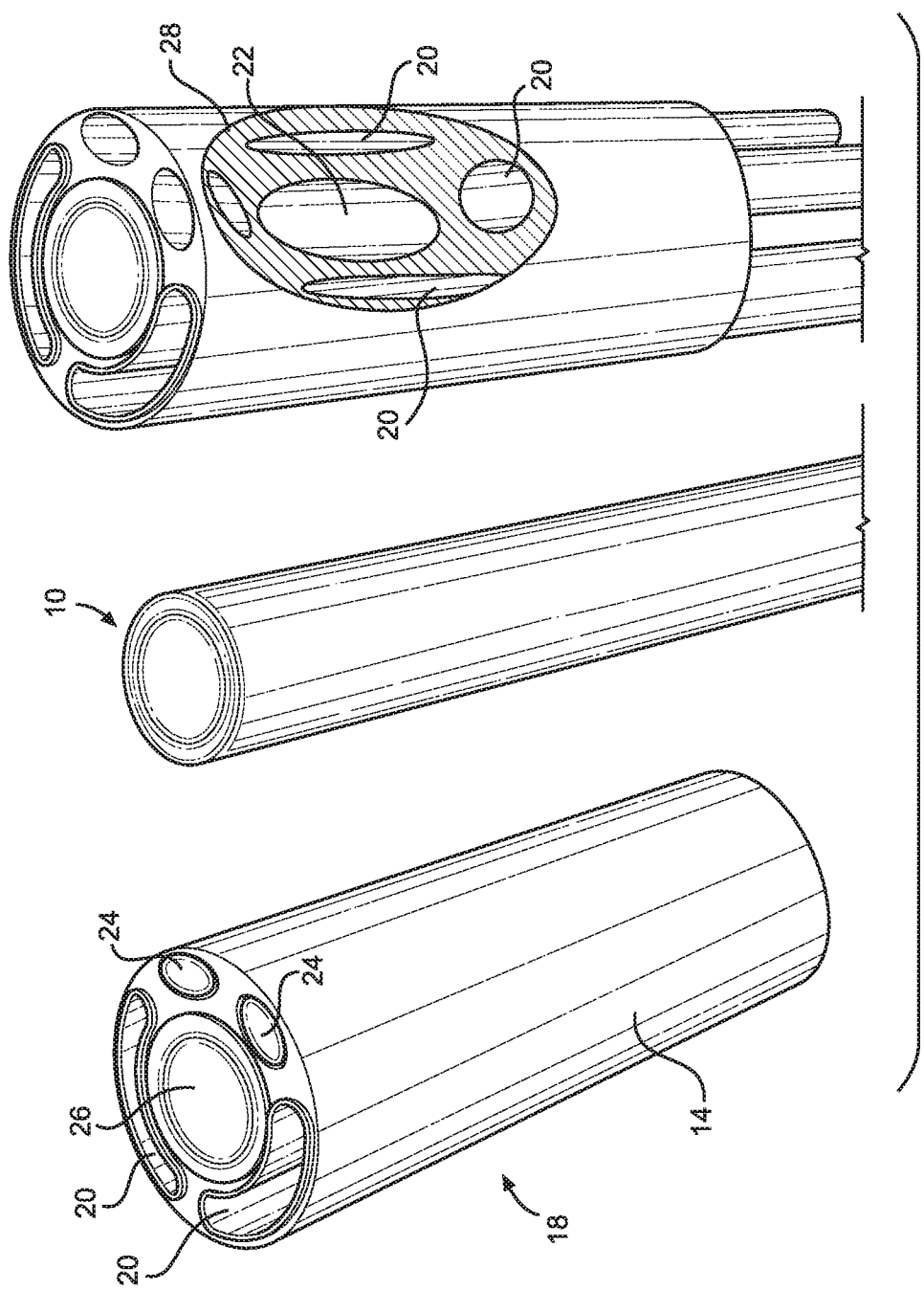
FIG. 26 illustrates a portion of an assembled scope and irrigator on the left, a bare endoscope in the center, and an assembled scope and irrigator with a cutaway demonstrating the exposed isolated conduit channels on the right.

With reference to at least FIG. 26, the endoscope 10 includes at least one conduit 20 which extends longitudinally along an internal portion 22 of the shaft body 14. The internal portion 22 is substantially enclosed such that at least one conduit 20 is configured to transfer irrigant fluid to and from the flexible tip 18. The at least one conduit 20 may be configured to transfer fluid in a first direction and a second direction that is different from the first direction. A tip portion 28 of the at least one conduit 20 may be inflated or deflated. The endoscope 10 may also have at least one image sensor 26 coupled to the flexible tip 18. Image sensor 26 may include a camera, for example, having a covering lens. The image sensor 26 may be configured to detect electromagnetic radiation or other alternative modality such as ultrasound within a field of view. Image sensor 26 may detect electromagnetic radiation having a spectrum having a range that extends from gamma to infrared frequencies. Alternatively, image sensor 26 may detect electromagnetic radiation restricted to frequencies within the spectrum visible to human beings. Image sensor 26 may include a lens 27 coupled to the flexible tip 18. The flexible tip may be configured to allow the image sensor 26 to visualize images over 360-degrees along the lateral and transverse directions. Image sensor 26 may include an integrated circuit chip and may be capable of generating its own imaging modality.

Figure 13:
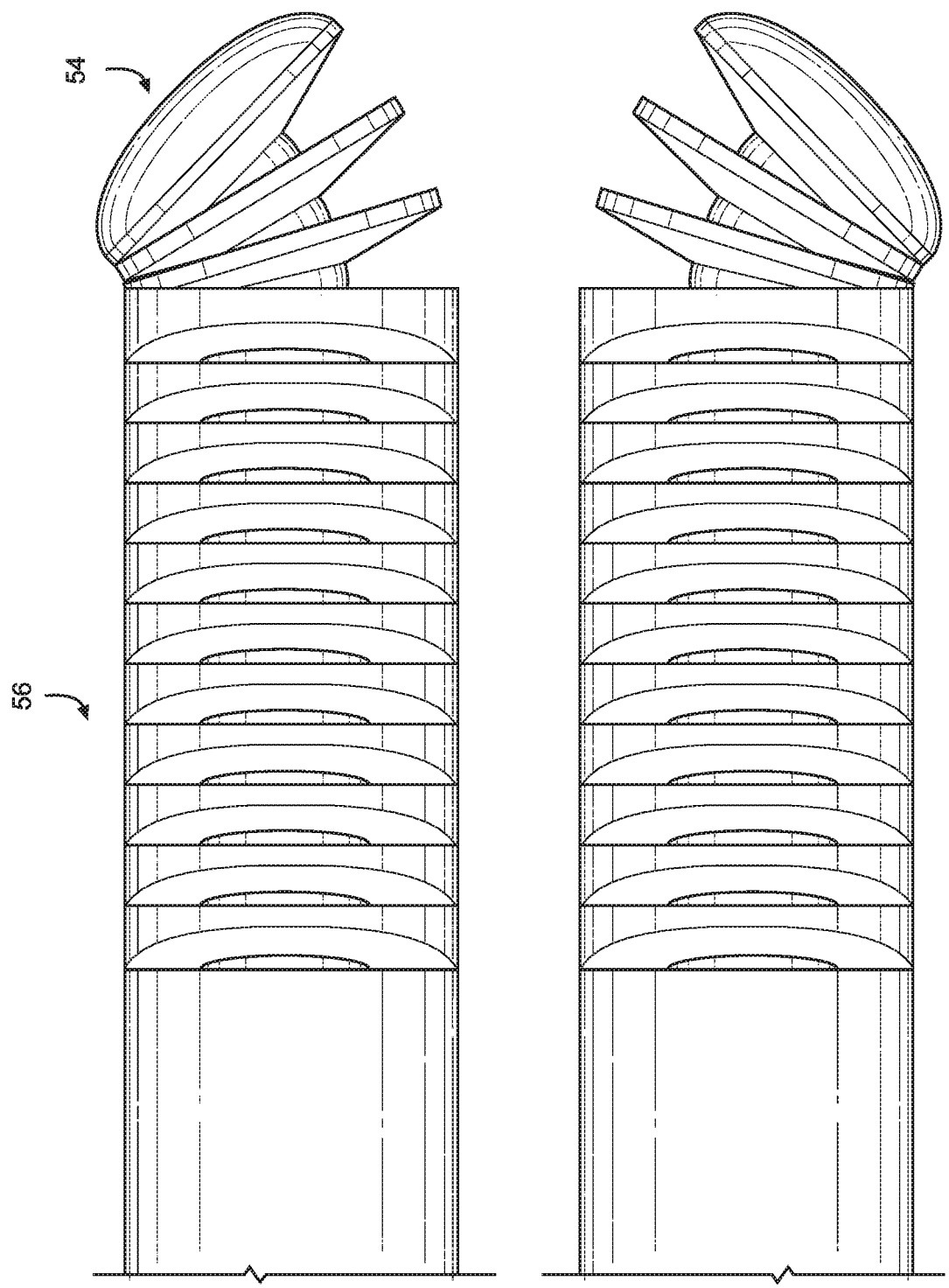
Figure 27:
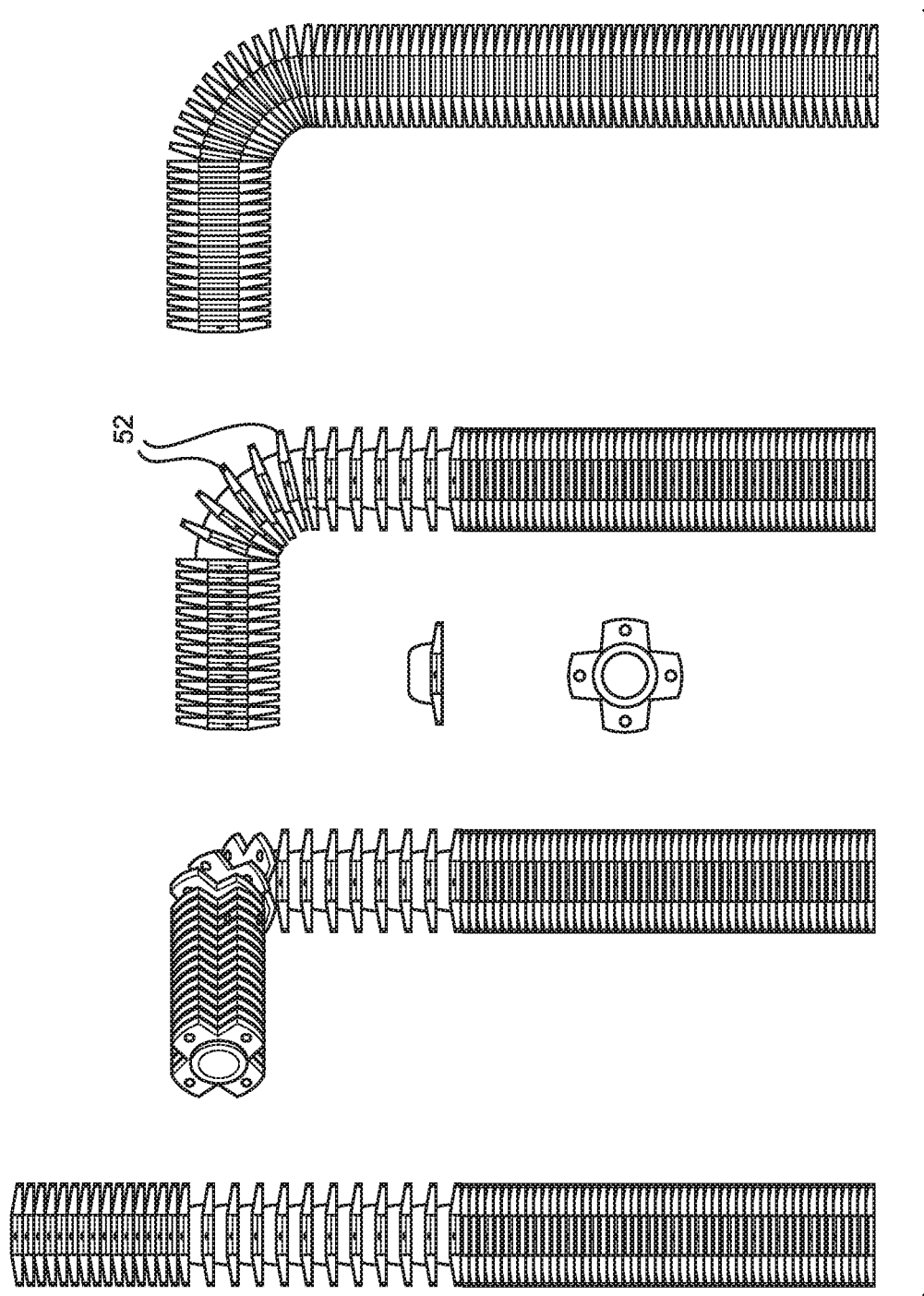
FIG. 27 shows the cruciform endoscope.

With reference, for example, to FIG. 27, the flexible tip 18 may include a plurality of segments 52 configured to flex along both the lateral and transverse directions. The flexible tip 18 may be configured to allow the image sensor 26 to obtain a 360° field of view. With reference, for example, to FIG. 13, the flexible tip 18 may define a distal portion 54 and a proximal portion 56 that is disposed proximal to the distal portion and spaced along the longitudinal direction from the distal portion. The distal and proximal portions 54, 56 of the flexible tip 18 may have the same or different progression or range of curvatures and are separately controllable. The curvatures may be sequential or synchronous.

The shaft body further includes at least one baffle 24 at the flexible tip 18 that is configured to direct irrigant fluid at the flexible tip 18. The at least one baffle 24 is configured to direct the fluid to clean the lens 27 of the image sensor 26 and/or irrigate the surgical field, such as a sinus area of a patient. For example, with reference to at least FIG. 42, a baffle 24 may be configured to move between a first position whereby the baffle 24 substantially directs the irrigant fluid towards the image sensor 26/lens 27, and a second position whereby the baffle 24 substantially directs the irrigant fluid towards the surgical field.

Figure 46:
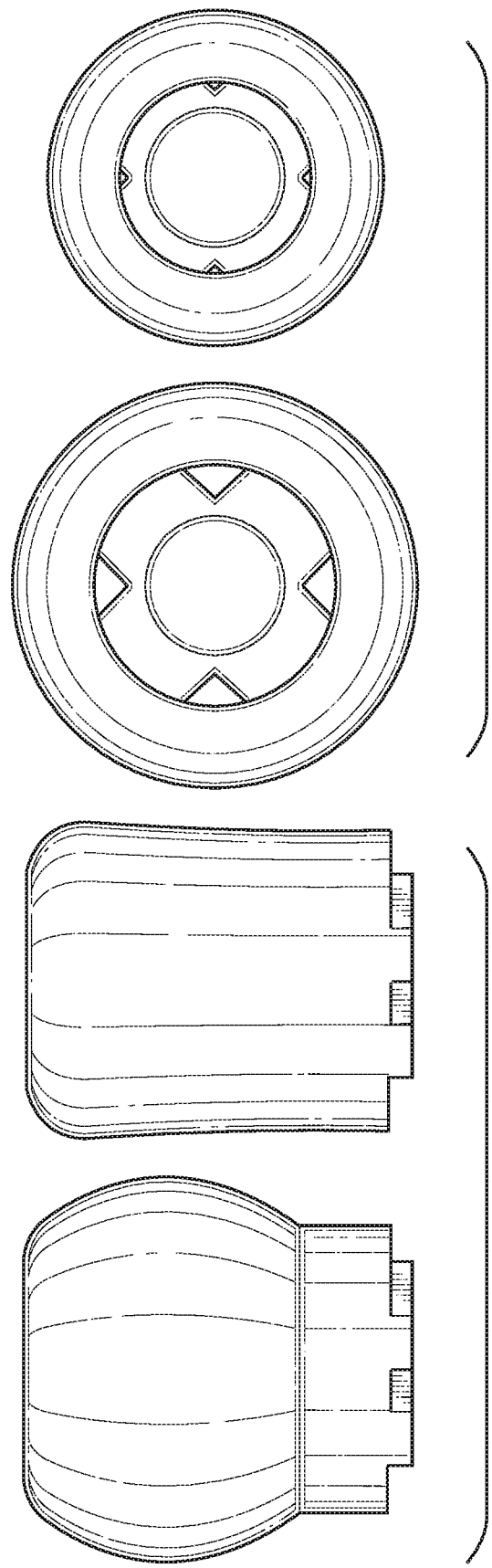

Further, when the baffle 24 is in the first position, a portion, such as a portion of the conduit at the distal end of the shaft, of the at least one conduit may be deflated. When the baffle 24 is in the second position, the portion, such as a portion of the conduit at the distal end of the shaft, of the at least one conduit may be inflated. In one example, as shown in FIG. 46, when the baffle 24 is in the first position, the at least one conduit 20 contains fluid at a first pressure. When the baffle 24 is in the second position, the at least one conduit 20 contains fluid at a second pressure. Here, the second pressure is greater than the first pressure. Specifically, the inflated, high pressure condition is on the left and initial and low pressure condition is on the right. FIG. 46A is the side view and 46B is the top view. The side view in FIG. 46A shows the extent of the increase in diameter and slight increase in height when inflated. FIG. 46B demonstrates the uncovering of the distal ends of the irrigation channels while the collar is inflated from the top view. The low pressure condition allows for complete covering of the channels for the re-direction of the fluid stream onto lens 27 of the image sensor 26.

Irrigant fluid may have a first pressure, a second pressure that is less than the first pressure, a third pressure that is zero, and a fourth pressure that is negative. In one example, the first pressure causes the baffle 24 to be in a first position and the second, third and fourth pressures cause the baffle to be in a second position.

Further, in FIG. 47, the far left drawing is a cruciform endoscope tip with exposed lens. The middle left diagram illustrates the empty irrigation sheath with the internal conduits without the circumferential baffle. The middle right diagram is the assembled endoscope and sheath with its circumferential tip with nozzles in the inflated, or high pressurized condition. The nozzles are pointing coaxially forwards. The far right diagram is also an assembled scope and sheath but it is in the non-inflated, low pressure or non field irrigating condition. The nozzles are pointing centrally towards the image sensor. The circumferential 'wall' is configured to not cutoff the image sensor's visual field (assuming a typical 90 degree field of view.) (See FIG. 56)

When the baffle is in the first position, the fluid may flow at a first fluid flow rate. When the baffle is in the second position, the fluid may flow at a second fluid flow rate. In one example, the second fluid flow rate is greater than the first fluid flow rate. Further, the baffle 24 may define a first shape when the baffle is in the first position and a second shape when in the second position. The first shape is different from the second shape. When the baffle 24 defines the first shape, a portion of the baffle may curve towards the image sensor. Accordingly, when the baffle is in the first position, the baffle is further configured to remove fluid from the image sensor. For example, when the baffle is in the first position, the fluid is configured to flow from the proximal portion towards the flexible tip and onto the image sensor. When the baffle is in the first position, the fluid may be further configured to flow from the image sensor towards the flexible tip and into the proximal portion. Further, when the baffle defines the second shape, a portion of the baffle curves away from the image sensor.

When the baffle is in the first position, the fluid is further configured to flow from the surgical field, such as the sinus area, towards the flexible tip and into the proximal portion.

For example, the left drawing in FIG. 45 is a perspective drawing illustrating the distal tip of the irrigation sheath in the low pressure condition. In this configuration the irrigation fluid is directed onto the image sensor for cleaning. The collar is not significantly inflated by the low irrigation pressure. The right drawing illustrates the collar 'inflated' under the higher pressure condition. The circumferential baffle has been retracted proximally and centrifugally by the bowing of the side wall of the inflatable collar. The distal ends of the conduit channels are uncovered and the irrigation fluid is not redirected centripetally. The stream is then allowed to project directly forwards onto the surgical field. Decreasing the irrigation pressure then allows for deflation of the collar and the re-establishment of the initial shape and configuration of the baffle.

Endoscope 10 may further include a light emitting diode 58 coupled to the flexible tip and electrically coupled to a power source (not shown), the light emitting diode configured to illuminate the field of view.

Figure 28:
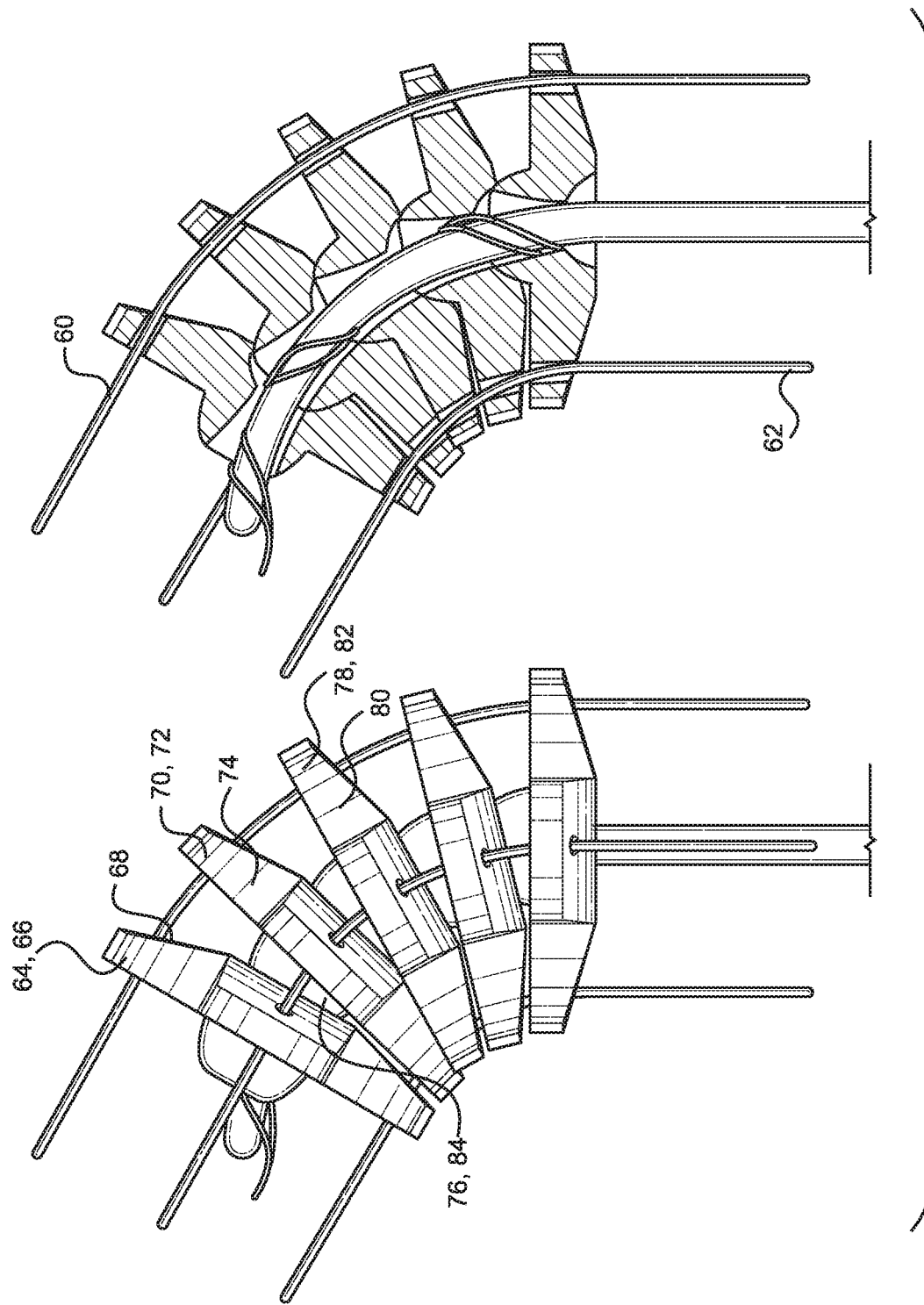
FIG. 28 shows the cruciform endoscope detail.
Figure 29:
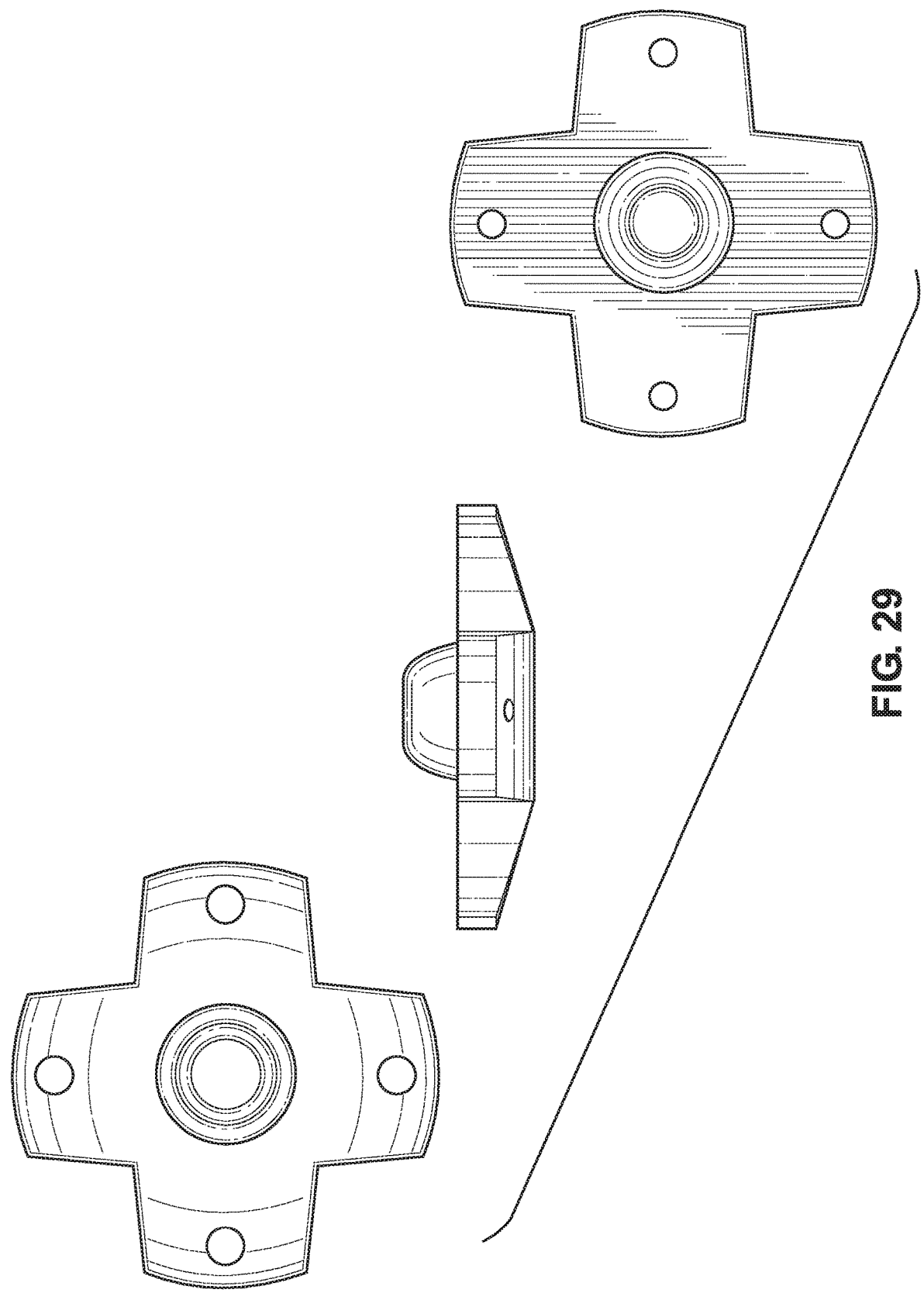
FIG. 29 shows cruciform linkages that provide for 15 degrees of rotation in both the Y and Z planes.
Figure 30:
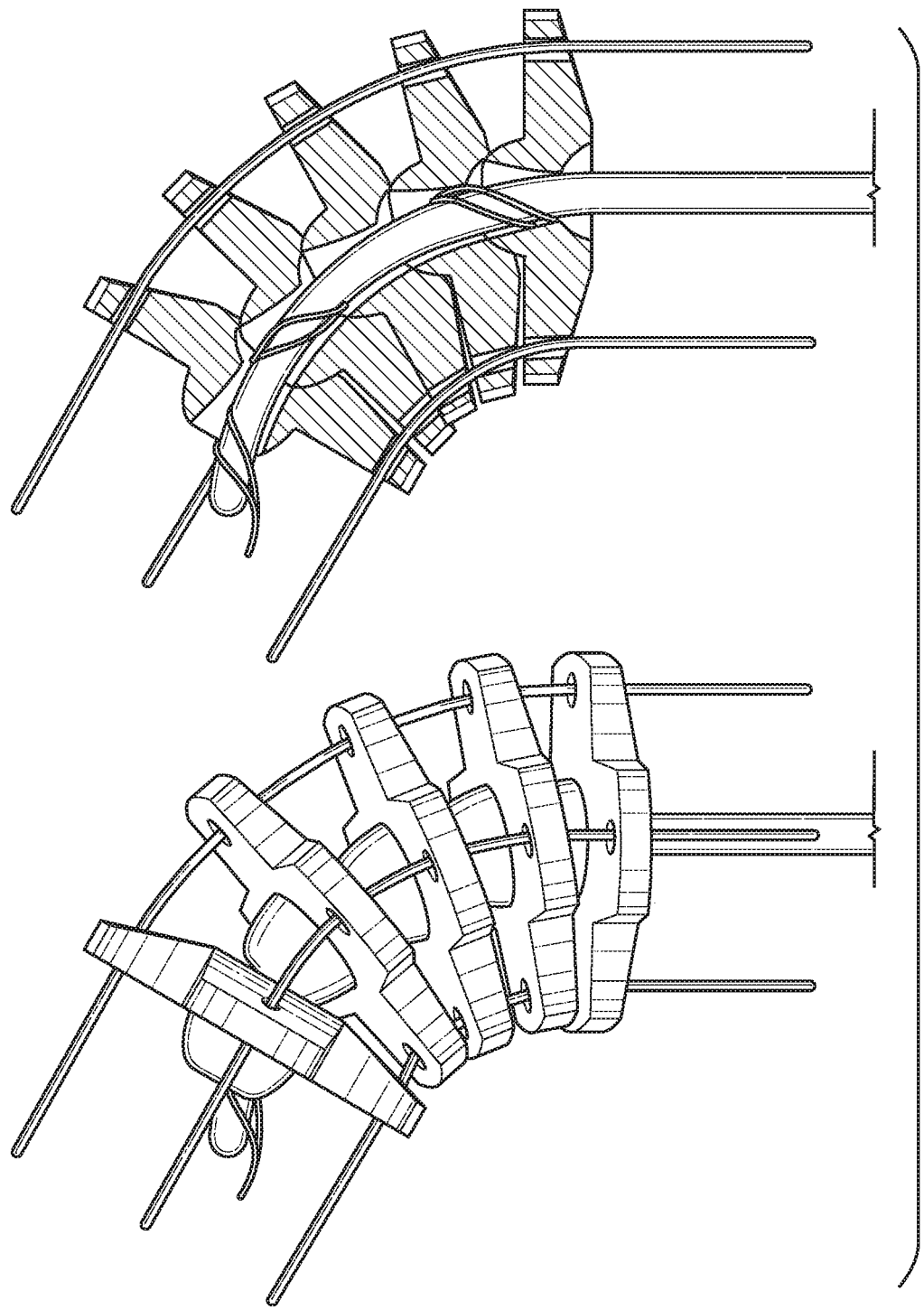
FIG. 30 illustrates perspective views for the cruciform scope.
Figure 31A:
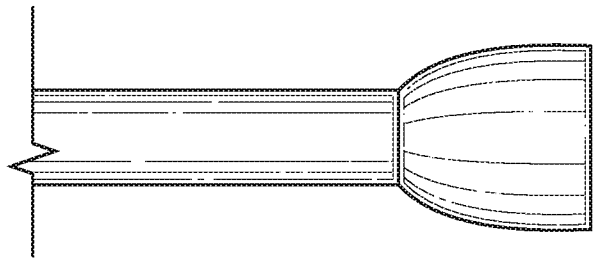
FIG. 31 illustrates the irrigation sheath bases utilizing internal connections. Drawing A is the irrigation sheath alone. Drawing B is the cruciform endoscope as it attaches to the hand piece (See FIG. 24). Drawing C is the combined sheath and endoscope. Drawing D is a cutaway view of a combined sheath and scope which has two inflow ports. Drawing E illustrates single inflow port but is also labeled to assist with identification.
Figure 31B:
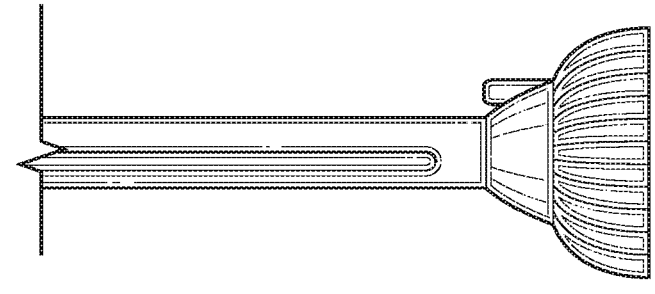
Figure 31C:
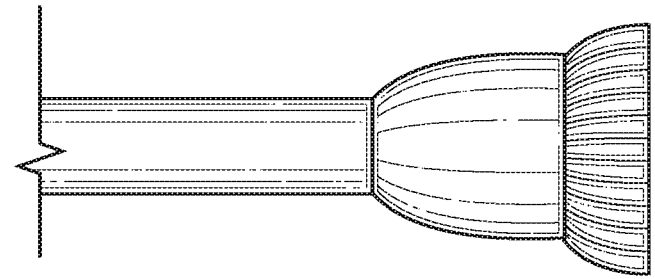
Figure 31D:
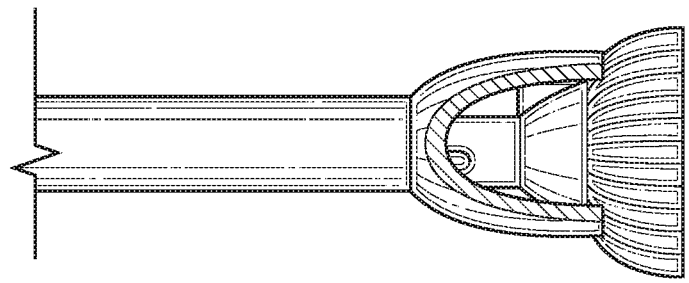
Figure 31E:
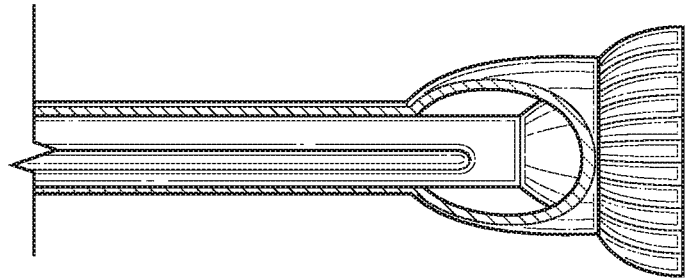

With reference to at least FIG. 28, endoscope 10 may include a first guide wire 60 that is elongate along the longitudinal direction and disposed within the internal portion of the shaft body. The endoscope 10 may also have a second guide wire 62 that is elongate along the longitudinal direction and disposed within the internal portion of the shaft body opposite the first guide wire. When one of the first or second guide wires tightens and the other of the first or second guide wires relaxes, the flexible tip 18 curves towards the first or second guide wire that is tightened. The endoscope may also have a first linkage 64 having a distal surface 66 and a proximal surface 68. The first linkage 64 is disposed within an internal portion of the shaft body 14. The endoscope may also have a second linkage 70 having a distal surface 72 and a proximal surface 74. The second linkage 70 may be disposed proximal to the first linkage 64 within the internal portion of the shaft body 14 such that the distal surface 72 of the second linkage 70 is operably coupled to the proximal surface 68 of the first linkage 64. The first and second linkages may each include a locking device 76 that is configured to lock the first linkage relative to the second linkage when they move relative to each other such, and wherein the flexible tip can be locked at a desired curvature.

Semi-rigid endoscope 10 may further include a third linkage 78 that has a distal surface 80 and a proximal surface 82. The third linkage 78 may be disposed proximal to the second linkage 70 within the internal portion of the shaft body. Flexible tip 18 may move at either the first linkage 64, the second linkage 70, and/or the third linkage 78, such that the flexible tip 18 is configured to have different types of curvatures and different radii of curvature. Endoscope 10 may include any number of linkages, such as one, two, three, four, five, or more linkages.

The locking device 76 may include at least one protrusion 84 that protrudes from the proximal surface of each of the first and second linkages and at least one recess 86 that recedes in to the distal surface of each of the first and second linkages. The at least one recess 86 is configured to receive the at least one protrusion 84 to thereby lock the at least one protrusion with respect to the at least one recess.

The endoscope 10 may also include a hand control 30 that 1) regulates the fluid flow and 2) directs the movement of the flexible tip 18. The hand control 30 may further include 1) an irrigation control 32 that regulates the fluid flow and 2) a tip control 34 that adjusts the movement of the flexible tip. Irrigation control 32 may be a trigger and tip control 34 may be sized and shaped to receive a human thumb. The hand control 30 may further comprise: 3) an input port 36 that is in fluid communication with the at least one conduit 20 such that the input port 36 transfers fluid to the at least one conduit 20 and 4) an output port 38 that is in fluid communication with the at least one conduit 20 such that the output port transfers fluid from the at least one conduit.

Hand control 30 may be electrically and mechanically coupled to the semi-rigid endoscope 10 and configured to direct movement of the flexible tip 18 along the lateral Y and transverse directions Z, and rotation of the proximal rigid portion 16 about a longitudinal axis that is parallel to the longitudinal direction X. The endoscope 10 may further include a screen 40 that is electrically connected to the hand control 30 and image sensor 26, whereby the screen 40 is configured to display an image 42 that is based upon a digital signal from the image sensor. Hand control 30 may be configured to adjust, invert, and/or rotate the image 42 displayed on the screen. Hand control 30 may further be configured to move the image 42 displayed on the screen 40. Hand control 30 may be configured to rotate the image 42 displayed on the screen 40, for example, by 90-degrees in either direction (left or right) on the screen 40. The hand control may be configured to direct the movement of the flexible tip 18 along the lateral Y and transverse Z directions. Hand control 30 may have a sensor 88 that is electrically and/or mechanically coupled to the flexible tip 18. Sensor 88 may be configured to detect an amount of curvature of the flexible tip and to provide a signal when the flexible tip is retroflexed more than 90 degrees.

Hand control 30 may define: 1) an internal portion that is substantially enclosed and 2) an external surface 46 that is opposite the internal portion. The system may further comprise an internal tube (not shown) that is located along the internal portion of the hand control, the internal tube being in fluid communication with the at least one conduit 20 whereby the internal tube is configured to transfer fluid to and from the at least one conduit.

The endoscope 10 may alternatively or additionally include an external tube (not shown) that is located along the external surface of the hand control, the external tube being in fluid communication with the at least one conduit whereby the external tube is configured to transfer fluid to and from the at least one conduit. An external surface 46 of the hand control defines a groove that is configured to receive the external tube.

The system may be configured such that the image 42 reorients itself in response to a thumb control movement of the hand control 30 when the endoscope is retroflexed more than 90 degrees such that the image 42 always depicts the "up" direction as towards the top of the patient's head.

Exemplary Embodiments

In some embodiments, the proposed endoscope design utilizes a rigid proximal shaft and a distal flexible tip, which can allow the surgeon to place the scope accurately and also to mobilize structures. Its optical and light capacity abilities are superior to that of current semi-rigid fiberoptic endoscopes, and it affords the surgeon the ability to see around obstacles. One feature is the ability to remain oriented in relation to the patient's anatomy when looking in all directions without producing rotational artifact. It provides for inspection of the anterior wall of the maxillary sinus or into the confines of the frontal sinus. It also provides for surgery in some locations without being in the way of the dissecting instruments, and is ergonomic for the surgeon and comfortable for the patient.

This design combines the strengths of both types of currently available endoscopes. It provides for maneuverability of the scope into the nose with the tip facing forward so that the surgeon may see directly where he is going. When he arrives at his destination, the surgeon can look in multiple directions without a change in orientation of the monitor. It provides visualization in a smooth 360° in two different planes, thus maximizing the surgeon's efficiency because he does not need to pre-select a fixed optical angle. Having obtained the desired visual field, the endoscope tip can be "locked" to maintain that view and orientation. In this "locked" configuration, the endoscope can also be used to gently retract structures.

By providing different views on demand, it allows the surgeon to avoid the time consuming and cumbersome exercise of having to change endoscopes during the case. A continuously semi-rigid endoscope allows for micro alterations of visualization of the surgical field, allowing panning, rather than quantal multiple degree jumps in visualization in the viewing angle which is required by using individual fixed angle endoscopes. The endoscope offers excellent visualization and illumination and could provide more physical flexibility than the present fiberoptic endoscopes.

The positions of the optical tip are controlled by an electronic controller that activates pairs of oppositely placed guide wires. Unless activated by the controller, the guide wires are immobile. When activated, tightening one wire of the pair while relaxing its mate forces curvature of the tip in the direction of the tightened wire. Alternatively, curvature in the other direction occurs by the opposite relaxation and tension. Both sets of wires run longitudinally along the long axis of the endoscope but are set at right angles to each other, as viewed coronally from the tip of the scope. This arrangement produces motion in both Y and Z planes.

Figure 4:
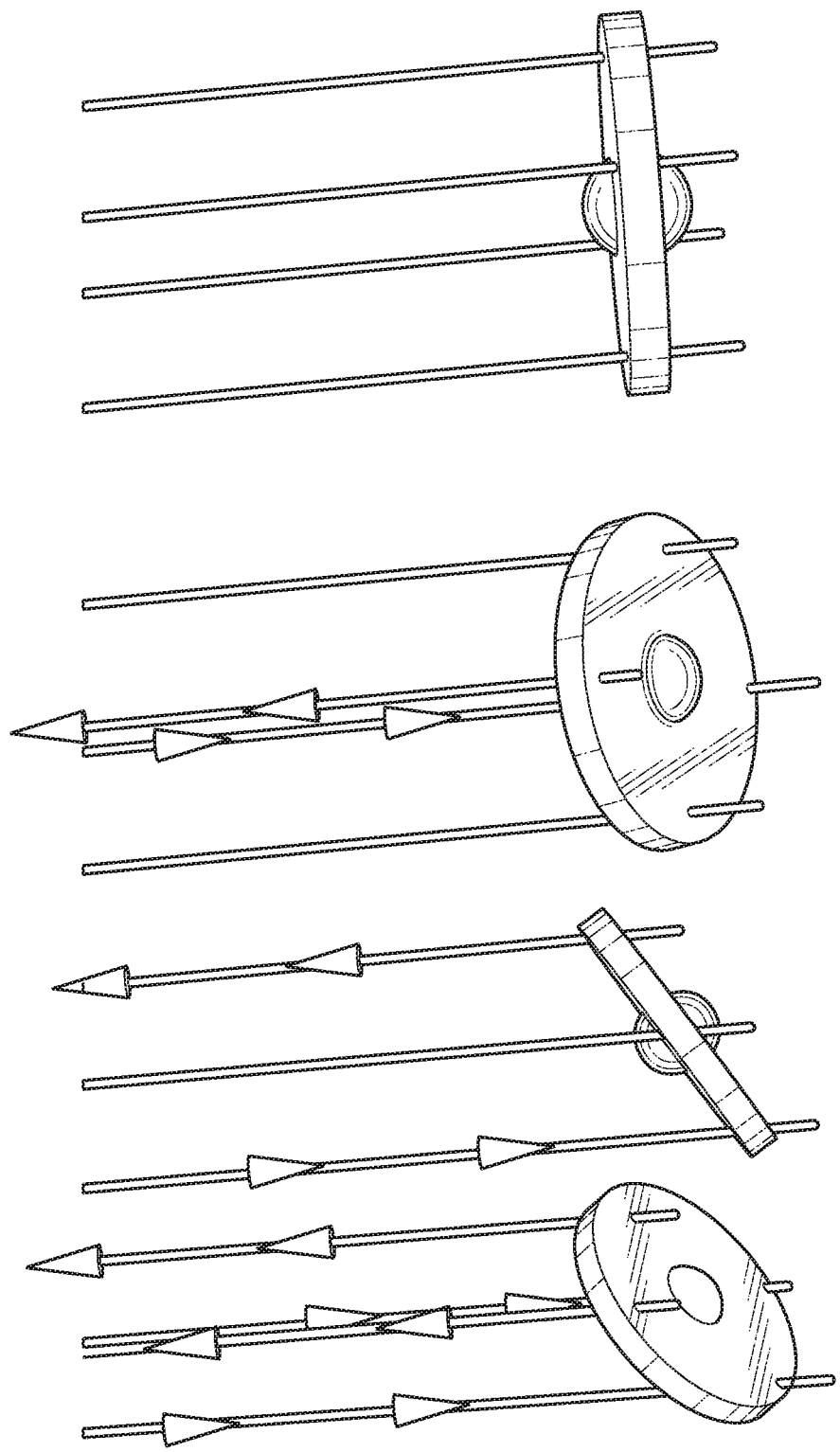
FIG. 4 is an illustrative drawing of the actions of the guide wires.

FIG. 4 is an illustrative drawing of the actions of the guide wires. The top linkage is in a neutral position. (The wire extensions do not completely penetrate the linkage if it is the terminal link. They are shown here to diagrammatically help orient the viewer to the location of the wires. This drawing shows the linkage pulled to the right. The motion of the guide wires is noted by the cones in this and each of the following diagrams. This drawing represents the linkage directed upwards. This drawing demonstrates the linkage directed superiorly and to the right at the same time. The series of diagrams in FIG. 4 illustrate only one linkage. In the constructed complete endoscope there may be, for example, twelve linkages. The combination of multiple links permits three dimensional directionality.

As noted above, when the electronically assisted controller is not actively changing the curvatures at the tip, the wires are all placed under relatively higher tension and locked in place. This rigidity is caused by the increased friction between adjacent linkages. Because only the tip of the endoscope is malleable while not under tension, restricting the motion of all guide wires that control this relatively small distance results in a non-pliable endoscope configuration. (Additional alternative locking techniques are available.)

The proximal portion of the scope can be axially rotated within the handle to allow a comfortable ergonomic hand position and yet permit an appropriate anatomic alignment to the body. For example, thumb activated electronically assisted 'joy stick' controls the distal flexible tip segment(s). It is designed to be easily convertible between right and left handed utilization. As noted above, when the joy stick is not activated, the potentially curvable portion is held rigid. In each design an image sensor is affixed to the distal end of the endoscope. The surgeon optionally may rotate the endoscope within the handle to optimally orient the direction of curvature of the semi-rigid portion of the scope. As the scope is axially rotated to align the curvature, the image viewed on the monitor is also obligated to rotate. This undesirable result is remedied by having a circuit which electronically rotates the image to the correct orientation. This control is conveniently placed on the top of the handle. The image sensor is much smaller and lighter than a camera head. It also results in a lighter, more ergonomic instrument. The circuit can not only rotate the image, but can also invert the image. This switched control for image inversion is also on the handle. In each of these new endoscopes the semi-rigid arcs of curvature of the distal tip are in two orthogonal planes, Y and Z. These run parallel to the long axis of the scope and can have similar or different curvatures depending on which of the following designs is chosen. The semi-rigid portion of the endoscope is encased in a thin, soft, semi-rigid inner sheath which permits the scope to curve unrestrictedly but isolates the inner mechanisms from the patient and as will be demonstrated any irrigation fluids.

Option 1

One configuration of the endoscope utilizes equal distal tip curvature abilities in both the Y and Z planes. It has arcs of full 180° rotation in both planes. One possible progression of the endoscope curvature is to gradually and synchronously deform from straight to completely retroflexed in an ever tightening smooth arc. Another progression is to start the curvature at the tip and then progressively and serially curve the more proximal segments. A comparison of these two types of curvature progression is illustrated in FIG. 5. The upwards directed curvatures illustrate gradual progressive curvature along the entire length of the semi-rigid portion of the scope. A significant detracting feature of this design option is that this scope cannot be well utilized in cramped locations.

FIG. 5 illustrates the different curvatures caused when designing the endoscope to either curve with each linkage curving equally throughout the entire semi-rigid segment (upwards curvatures), or when causing each linkage to rotate only after the next most distal linkage has rotated through its complete range of 15° rotation (downwards curvatures). Straightening the endoscope's curvature progresses in the opposite progression with straightening the linkages serially from proximal to distally. The differences in contour are most pronounced with relatively small amounts of curvature. There is no curvature difference at 0° and 180° of complete retroflection. The gradual equal rotation curved scope requires more room to effect its small angle. Only after the end segment(s) has (have) maximally rotated does the next linkage move.

The potential fields of view of both progressions are illustrated in FIG. 6. Both of these configurations allow the scope to see around obstacles and can be placed somewhat distant from the surgical site so as to avoid getting in the way of the dissecting instruments. The design also allows greater freedom of motion and placement. If the surgeon retroflexes the scope more than 90° in the vertical plane the image becomes inverted and might become disorienting. The electronic image correction circuit would optionally be utilized in this circumstance. The image is upside down but not reversed right to left.

FIG. 6 is a composite rendering of both the continuous, equal curvature scope and the sequentially curving endoscopes' fields of view for several discontinuous angles in a single plane and demonstrates the full 360 degree coplanar viewing capability. In the left drawing, all curvatures occur at the same location, i.e. at the distal end of the rigid portion of the endoscope. The right drawing illustrates the curvatures occurring at differing locations along the length of the semi-rigid portion of the scope thereby minimizing the space required for relatively small angles of curvature.

Figure 7:
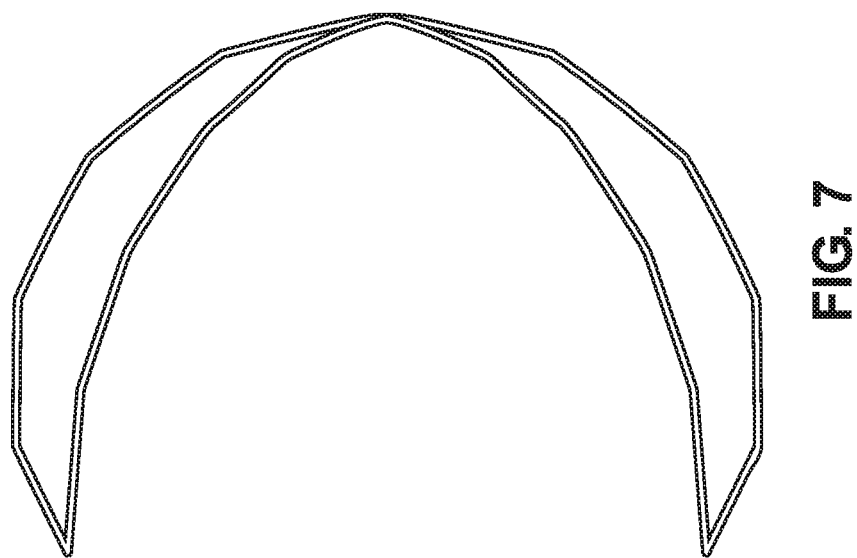
FIG. 7 illustrates the position of the tip of the endoscope for both designs as they curve from 180° flexion in one direction through zero degrees and back to full 180° flexion in the other direction.

FIG. 7 illustrates the position of the tip of the endoscope for both designs as they curve from 180° flexion in one direction through zero degrees and back to full 180° flexion in the other direction. The flatter curve (inner curve in FIG. 7) is related to the serially flexed scope and the rounder, larger curve relates to the continuously curving scope. The segmentally curved scope requires less physical lateral space to visualize surgical fields at small scope angulations.

Figure 8:
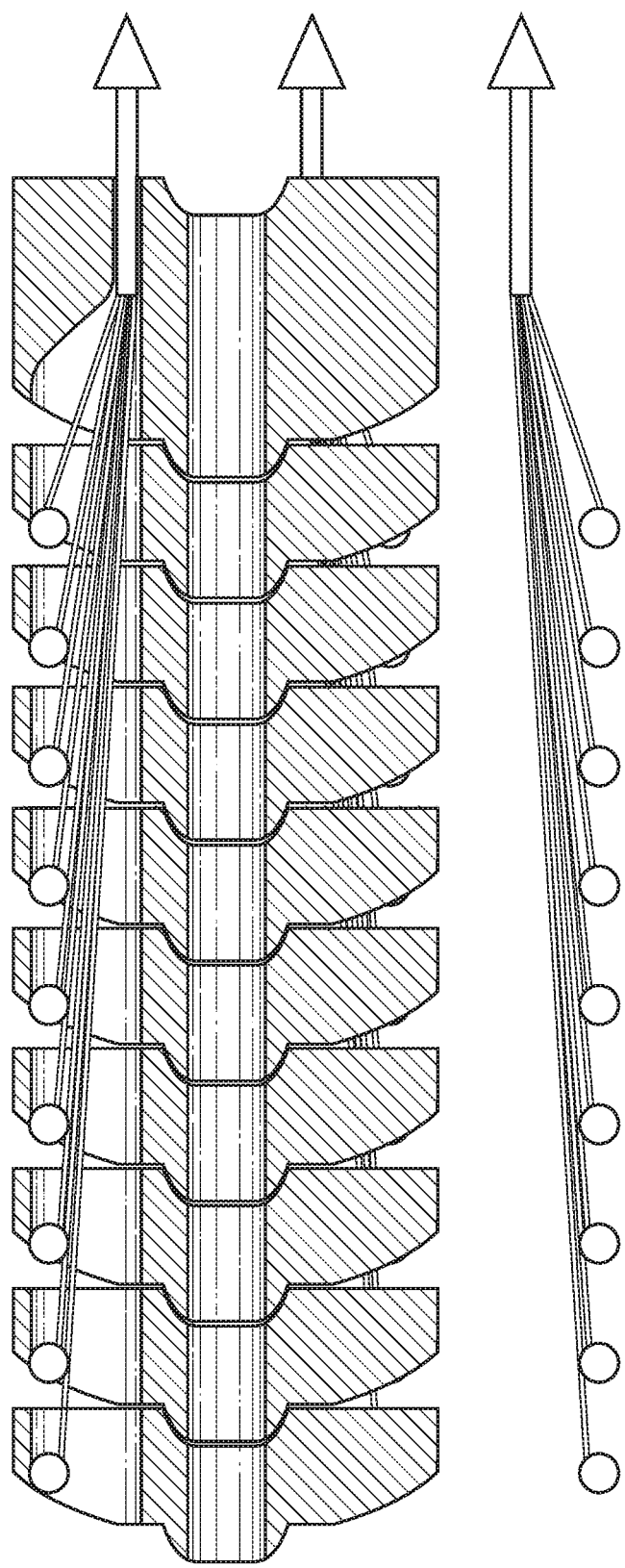
FIGS. 8 & 9 illustrate the guide wire configurations for endoscopes to curve either continuously or serially from distal to proximal.
Figure 9:
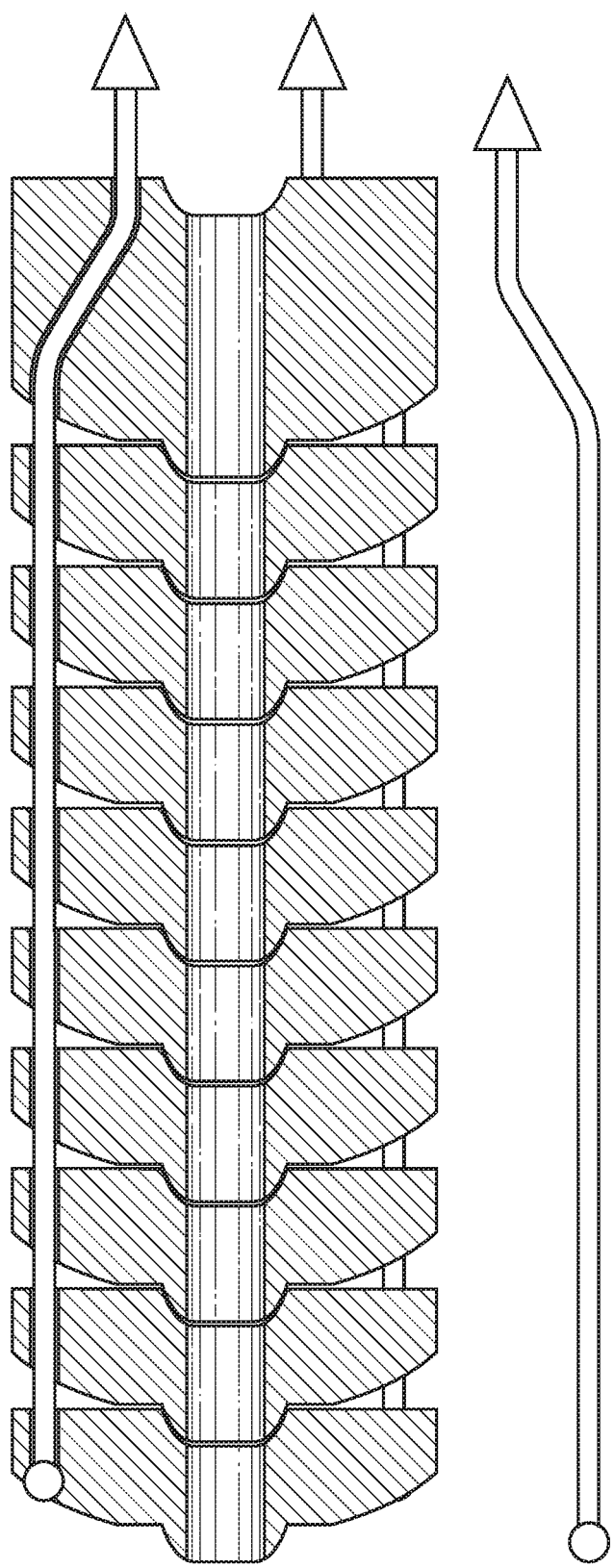
Figure 11:
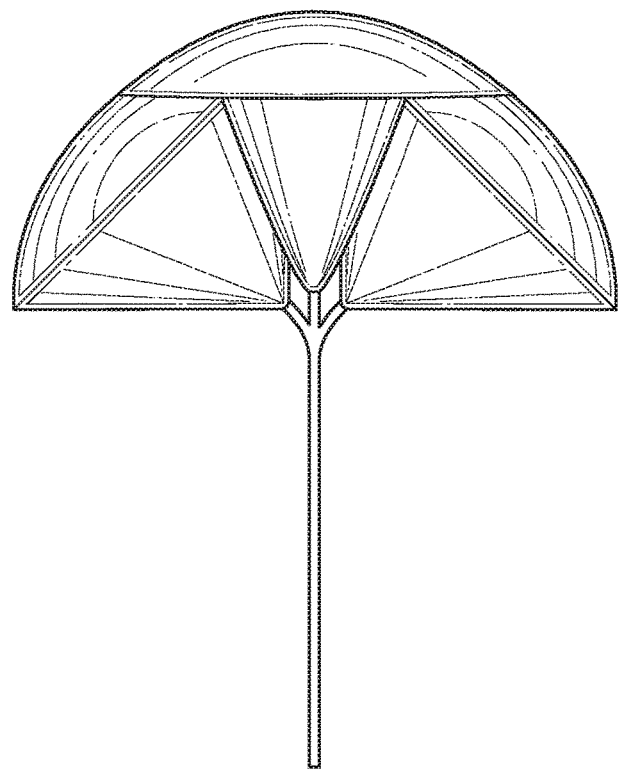
FIG. 11 is a composite drawing illustrating a full vertical 180 degree visualization using this design.

FIGS. 8 & 9 illustrate the guide wire configurations for endoscopes to curve either continuously or serially from distal to proximal. They are primarily illustrating the wires and not the linkage design. The same wire configurations are used no matter how many armature wings exist on each linkage and no matter how many linkages in the sequence are being rotated. Also illustrated is the more centripetal location for the guide wire once it has reached the rigid portion of the scope.

FIG. 8 illustrates the guide wire arrangement for an endoscope where all the segments curve synchronously and with equal amounts of curvature. The proximal combined wire is approximately 3 times the diameter of each of the smaller wires which ensures the same combined strength of the 9 individual wires. The distance the combined wire must move in order to completely curve the endoscope is only the distance required to rotate each of the linkages. The top of FIG. 8 shows the wire array in place and the bottom portion of the drawing shows the isolated wire array.

FIG. 9 illustrates the semi-rigid guide wire arrangement for the endoscope where each linkage is rotated in serial fashion. The guide wire is only anchored to the distal most linkage. When tension is applied to the wire it first rotates the end linkage as this is the only attachment point. Once that linkage has rotated it contacts the next most proximal linkage and then tension is applied to rotate it. This progression is then repeated in serial fashion causing the endoscope to curve from distal to proximal. The total distance that the guide wire must travel to cause complete curvature of the endoscope is 9 times the distance needed to rotate each of the individual linkages. This is 9 times the distance required compared to the array illustrated in FIG. 8. The amount of tension required to effect curvature however is 9 times less (neglecting frictional effect). The top of FIG. 9 shows the wire in place and the bottom portion of the drawing shows the isolated wire.

Option 2

Figure 15:
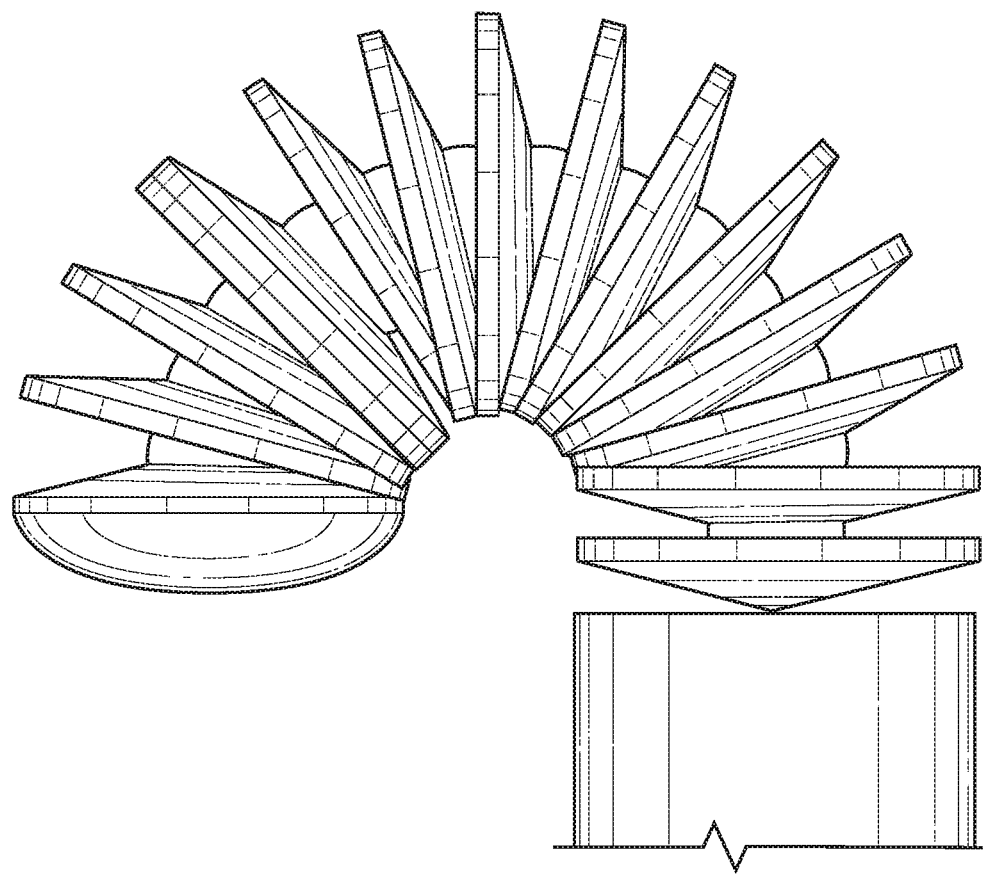
FIGS. 14 and 15 are schematics of the construction of the scope with the 180 degree curvature.
Figure 14:
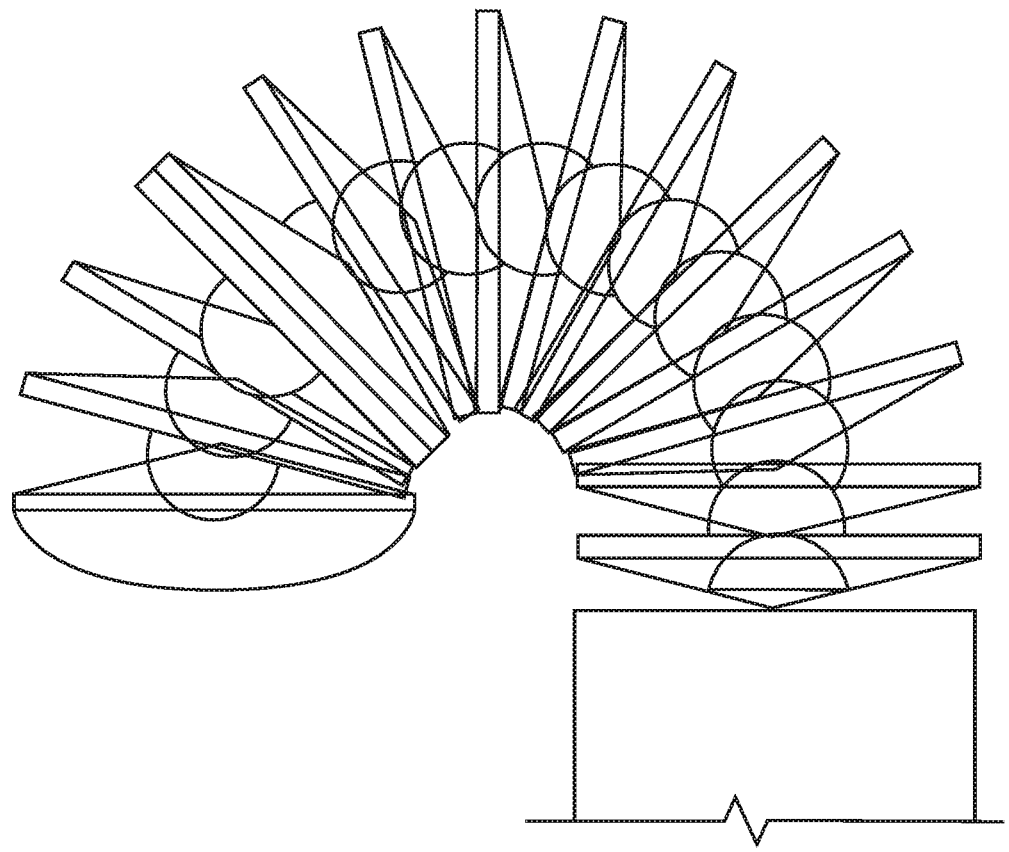

Another design angulates the tip in a short arc of a maximum of 45 degrees in only one plane, e.g. vertical, (FIGS. 10, 11, 12 & 13) and a much longer arc of curvature in the plane at right angles to it, e.g. horizontal (FIGS. 14 & 15). The short vertical arc is accomplished by designing the distal most three linkages to be able to equally rotate in both planes. (FIGS. 16 & 17) The remaining nine linkages can only swivel in the 'horizontal' plane. As the distal 3 links are the only linkages which can move in the vertical plane, vertical angulation and visualization is obtained in a very small region of the endoscope. The longer horizontal arc accomplishes its full 180° curvature by utilizing the two different arc segments (the distal 3 and the more proximal 9.) Each linkage rotates with a continuous 15 degree arc yielding a continuous smooth curve as in the first design discussed in option 1. This design obligates the surgeon to use the more sharply angulating vertical segment for close work. This visualization is relatively similar to currently available rigid endoscopes. By restricting the vertical tip motion to only three links, each link rotates up to 15 degrees. In order to visualize obliquely, the scope must be axially rotated. As with today's endoscopes, this produces rotational distortion that requires correction (this electronic correction circuitry is designed on the handle). The maximal arc of visualization of 45 degrees is obtained within a short distance of the distal tip thereby minimizing the space needed to orient the image sensor. Contrarily, the horizontal curvature is four times longer, or has 12 linkages, so a comparable arc of 45 degrees makes a much longer, gentler curve with each linkage only rotating 3.75 degrees. This requires much more space and so cannot be used in cramped locations. This design allows for visualization in very tight spaces by using the 'vertical tip' where a wide arc of curvature is not desired. It also has the ability to curve around obstructions by using the more semi-rigid longer 'horizontal' curve. This configuration would allow the surgeon to choose to orient the scope when initially placing it into the nostril (i.e., when used in sinus surgery), depending on the arc necessary to perform the procedure to be done at that time. This can be accomplished by rotating the endoscope within the hand piece by rotating the knurled knob. The electronic correction circuit mentioned above permits physically rotating the scope within the handle so that the long arc can be oriented vertically but maintains the image on the monitor correctly aligned. These different abilities afford more options to the surgeon than Design Option 1. This is also a physically more robust design. Because this design inherently allows greater curvature in only one plane, the surgeon must keep in mind the orientation of the scope during any dissection. The electronic image correction of the image sensor can be changed while the scope is in place.

Figure 10:
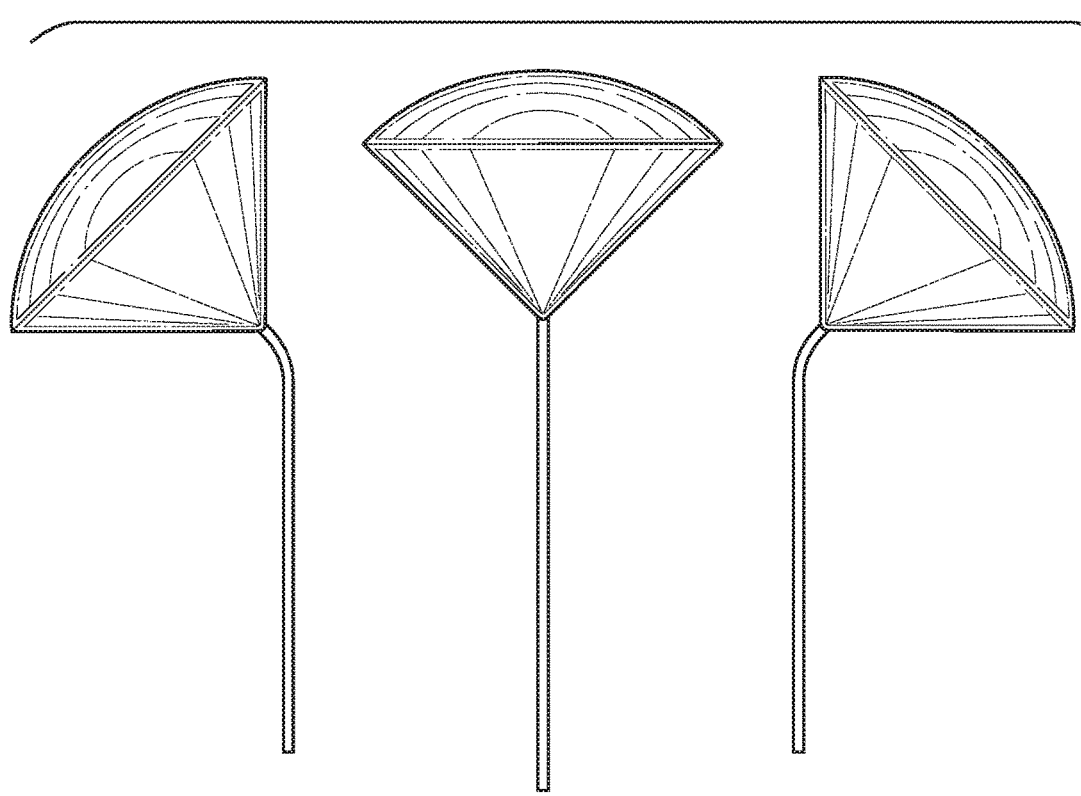
FIG. 10 represents the typical field of view for the image sensors with ranges of 90°.
Figure 12:
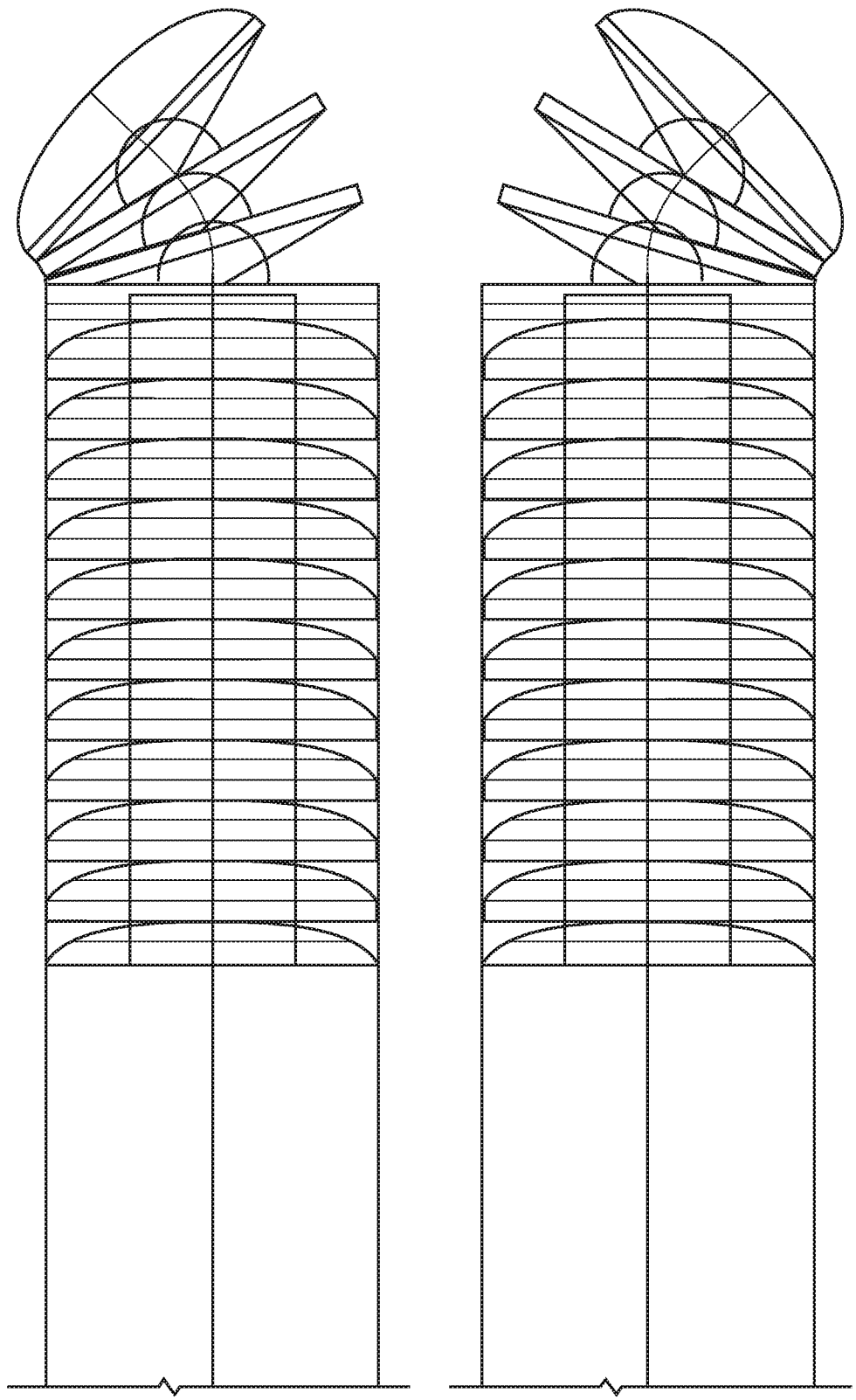
FIGS. 12 and 13 are schematics of the construction of the scope with the restricted 45 degree vertical curvature.

The drawings in FIG. 10 represent the typical field of view for the present generation of Chip Tip image sensors of 90°. The Option 2 design maintains this familiar surgical view but also allows the surgeon to introduce the scope while visualizing straight ahead, as well as up to 45° above or below the horizon. Design Option 2 thus encompasses both the most frequently used 0 and 30 degree views and the less frequently used 45 degree view. The extreme 70, 90 and 110° angles, which are used the least (primarily for surgery of the frontal recess and frontal area sinuses) would be able to be visualized using the 'horizontally' oriented curved portion of the scope if the endoscope was rotated 90° about the longitudinal axis. The distortion created by this rotation is corrected with the controls on the handle. This design allows one to visualize 90° directly above and below the tip of the scope, albeit at the extreme range of the field of vision. There is no intrinsic reason that the scope must be restricted to this angle. The angle could be increased by adding more linkages or by increasing the angle of rotation per linkage.

Figure 16:
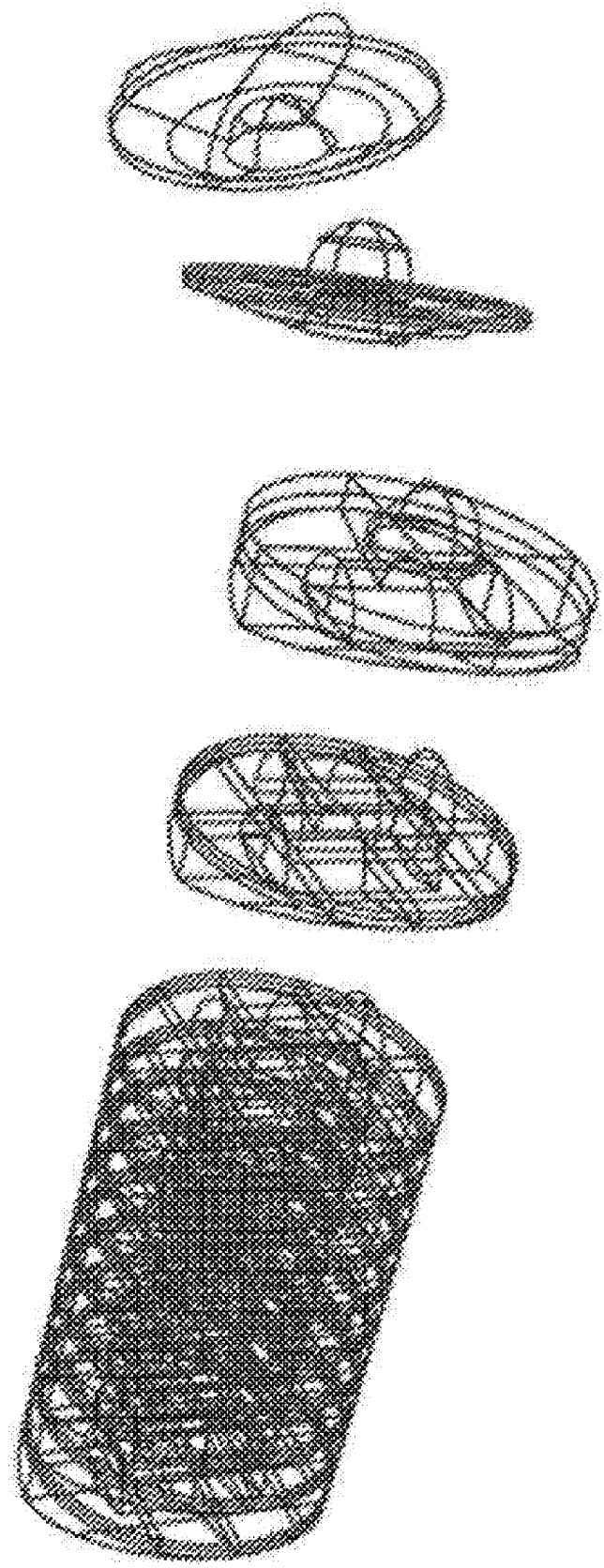
FIGS. 16 and 17 are wireframe and rendered perspective views of individual linkages with control wires, fiber optic channels, central lumen, and casing not shown.
Figure 17:
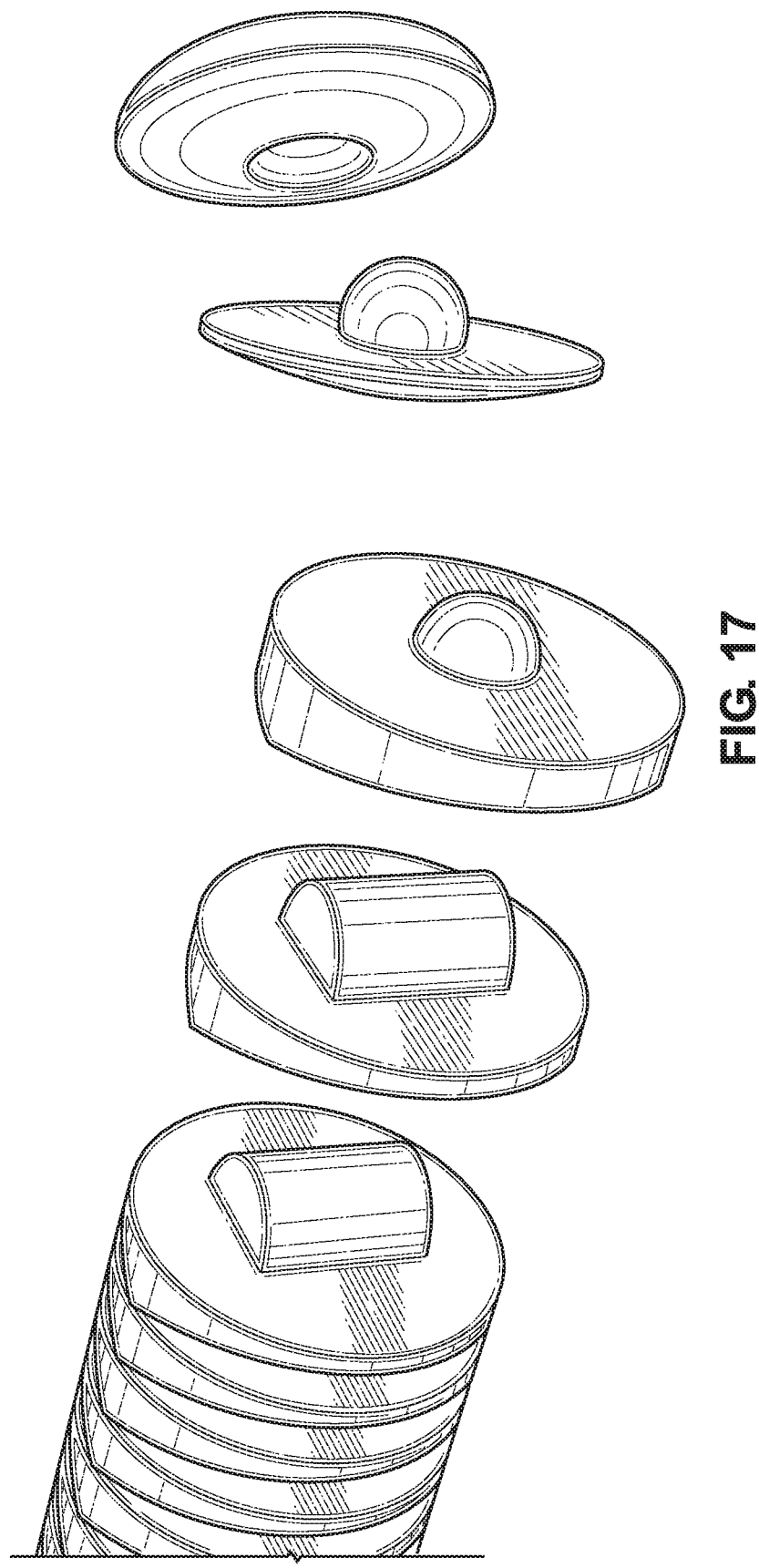
Figure 18:
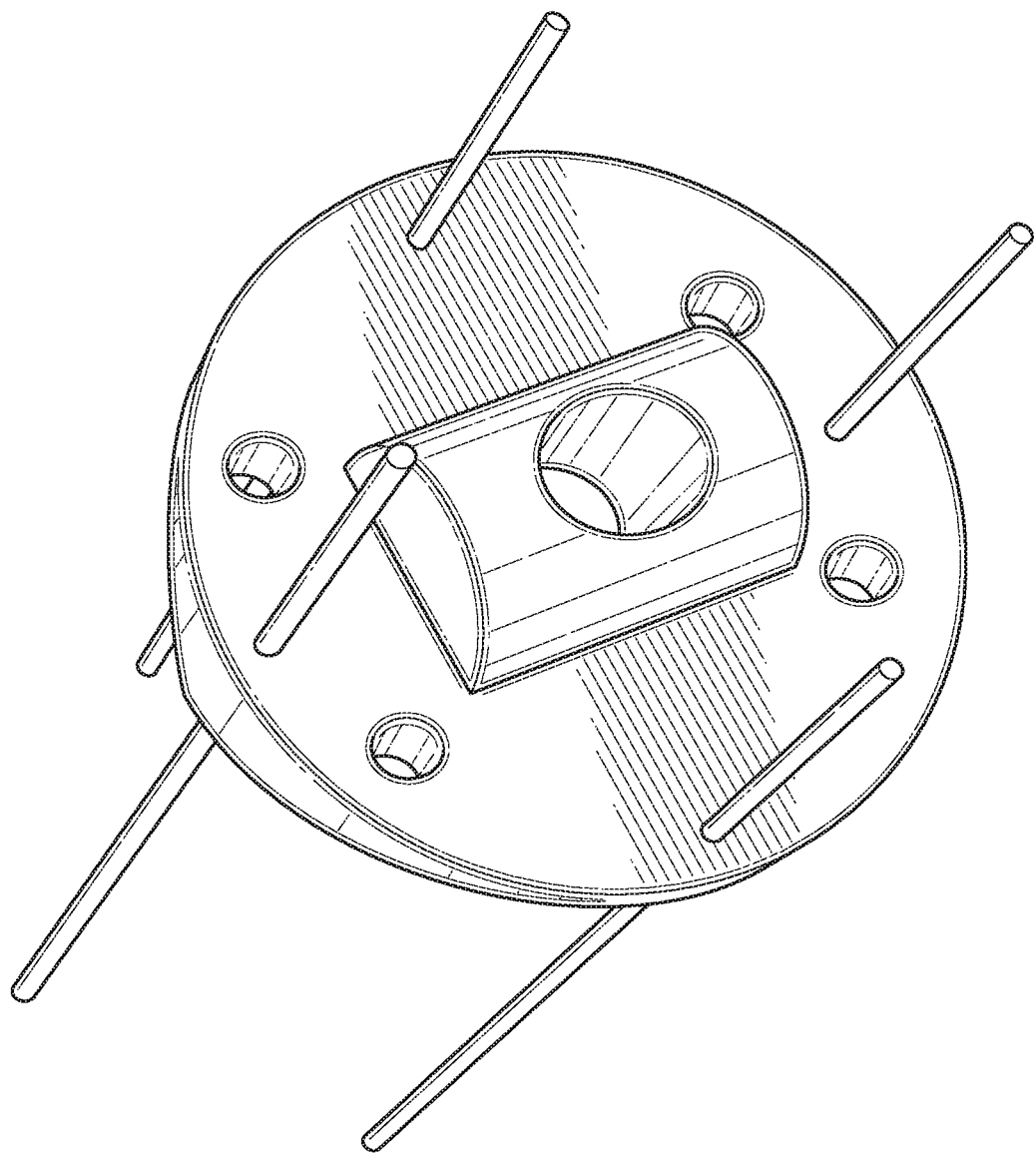
FIG. 18 represents a linkage which can move in only one plane.

The linkages on the left side of the FIGS. 16 & 17 provide horizontal motion and have semi-cylindrical couplings. There is a transition link in the middle of FIG. 17 which itself can only move horizontally (grey linkage in FIG. 14) but couples with the subsequent link that has freedom to move in both planes. It has a semi-spherical male linkage rather than the more proximally utilized semi-cylindrical male linkage. The semi-spherical male linkage allows for 'vertical' ("Z" plane) and 'horizontal' ("Y" plane) rotation concomitantly. To the left of the transition link, the scope can move only horizontally. To the right of the link the scope can concurrently move equally horizontally and vertically. Each linkage was arbitrarily designed to permit a maximal rotation of 15 degrees. The fiberoptic and control guide wire channels in FIGS. 12-17 are not drawn. One wire pair would be placed vertically 180 degrees opposed from each other and orthogonally positioned to the other horizontal pair. In that portion of the semi-rigid endoscope which can move only in one plane, the fiberoptic channels, if utilized, are placed closer to the portion of each linkage which acts as the hinge. This arrangement is illustrated in FIG. 18. The channels are more vertically located through the linkage and are placed in approximately the 11:00, 1:00, 5:00, and 7:00 positions of a clock face. This permits the more extreme horizontal curvatures without undue tension. An image sensor with self-contained LED or other light sources would simplify and improve the design and also lead to other future developments which are in process and not presented in this proposal.

As illustrated in the composite graphic (FIG. 19), the use of these parameters presented in Option 2 makes it possible to see 360 degrees in all directions. There is an oval of non-visualized anatomy directly above and below the malleable tip. It measures approximately 9×6 mm. This area could be seen by moving the endoscope less than 5 mm in any direction. It is also possible to see this area without motion of the scope if the vertical tip angulation is designed with more than the described 45 degrees mobility. Also, the descriptive label of horizontal and vertical curvatures is arbitrary. The curvatures might more correctly be labeled long and short arcs.

Option 3

A third embodiment has a tip that can curve in two separately controlled sections. Each section is independently controlled by the tip control 34. Tip control 34 may be attached to a joystick. Moving the tip control 34 without depression moves only the most distal (three linkage) segment, whereas depressing the controller moves only the more proximal of the two segments (nine linkages). As an alternative option, depressing the controller might be able to curve the entire length of the flexible segment (all 12 segments), and not depressing the controller would still only move the distal most tip (three linkages). The distal most section can curve to 45 degrees with 15 degrees of angulation per linkage segment in either direction (Y and Z). This is similar to the 'vertical distal curvature' in Option 2. This curvature is sequentially initiated at the very tip and the subsequent linkages move only after the next distal most one has rotated its maximal amount of 15 degrees. The tip can curve to the same maximum of 45 degrees. By utilizing just the distal tip curvature, while the remainder of the shaft and potentially curvible proximal segment remains stable, experienced surgeons can comfortably use this scope with very little retraining. The more proximal section curves independently when required. Once the more proximal segment has achieved the desired shape, the proximal segment can again be held rigid but still allow the distal tip its mobility to pan 45 degrees in any direction. The ability to position the scope in a serpentine fashion and still be able to peer around using just the tip is presently unheard of in today's endoscopic assemblage. The two combined curvatures allow for 180 degrees of curvature/visualization. Present generations of image sensors have an approximate 90 degrees field of view. This field of view in combination with the 180 degree curving ability potentially permits visualization circumferentially. (See FIG. 20) The guide wire arrangements illustrated in FIGS. 8 & 9 are now more important. Once the wires are no longer in the active distal curvature region of the endoscope their hole locations are placed more centripetally. This allows the more proximal portions of the scope to curve without undue changes in curvature of the distal linkages. This curvature symmetry in both the Y and Z planes permits the introduction of the endoscope into the nose with less concern for final desired orientation. The increased flexibility is, however, not as mechanically strong as the preceding two options. This endoscope is not only more flexible mechanically but also in its applications. If the surgeon desires to retroflex the scope vertically more than 90 degrees, the image would be upside-down but not reversed. Again the electronic circuit mentioned above can be utilized for correction.

Utilizing any of these configurations of the semi-rigid endoscope, surgical exposure within the sinuses is dramatically improved. The surgeon is now able to visualize the roof and floor of the sinuses without artifactual distortion when using the semi-rigid scope. Utilizing Option 3, when the long curvature of the scope is directed to the side, as it would be when used within the maxillary sinus, it is possible to look up and down and see the floor and roof of the sinus independent of the horizontal curvature. The endoscope flexes 45° vertically in either direction, but using an image sensor with a 90° field of view, maximal vertical visualization is 180°. With 180 degree flexibility in the horizontal plane, any of these semi-rigid endoscope options make visible even a portion of the medial sinus wall. It would then be possible to see circumferentially around the lacrimal duct. It is the only endoscope able to accomplish any of these feats. If the endoscope is placed along the floor of the nose and is retroflexly curved vertically into the middle meatus, the surgeon would have a view of the maxillary sinus opening and the infundibulum. This visualization is presently unobtainable. If the endoscope curvature is vertically oriented towards the forehead, it may also be able to see not only the frontal sinus drainage pathways but also look within. (If it were introduced in this fashion utilizing Option 2, the image on the monitor must be electronically rotated for correct alignment as it would more commonly be placed in the nose with the long curvature oriented in the horizontal plane.) The construction of this scope allows for panning the anatomic field in any plane a full 360 degrees while maintaining its orientation.

The Hand Piece

Fiberoptic light cords, irrigation tubing and camera leads are all in disarray and encumber the surgeon's hand and clutter the operative field. The proposed endoscope is held with a pistol-like grip, with an approximate 25 degree angular offset of the handle to the long axis of the rigid portion of the endoscope. The light post and cord placement exit the 'butt' of the pistol and parallel the forearm of the gripping hand to help prevent entanglement, or can be designed to be rotating. The axis of the scope can be physically rotated within the 'barrel' of the hand piece for correct patient orientation of the 'vertical' and 'horizontal' motion arcs by twisting the knurled knob. This allows for the individual specific hand and arm orientation desires of the operating surgeon. A thumb control allows for control of the endoscope's flexible tip in both planar directions. Moving the thumb controller forward causes the endoscope tip to move inferiorly. Conversely, moving it backwards causes the tip's motion upwards. Rightwards and leftwards control movement similarly results in right and left tip motion respectively. In the above options (1 & 3) utilizing symmetric design, the distal motion of the tip moves in the thumb direction even when the hand piece is held obliquely. The thumb control pocket, designed to accommodate the insertion of the tip of the thumb, is on a curved stalk which can be rotated to accommodate both right and left handed surgeons. Changing the handedness of the hand piece is accomplished by distracting the stem and repositioning to the alternate side of the pistol grip. If Option 3 is utilized, axial pressure on the thumb control changes curvature control from the distal to the more proximal segment as discussed above. See FIG. 24. Also as noted above, the guide wires only allow motion when the thumb control is activated. The thumb controller may be electronically, rather than directly mechanically linked to the guide wires. When the controller is not activated there is a tension control device which statically pulls on all four guide wires increasing the friction between all segments to make the scope more rigid. The tension is released when the thumb controller is activated allowing for free motion of the segments. The handle also contains: a rotational control knob which allows the surgeon to control the orientation of the image; an image inversion switch in case the vertical curvature exceeds 90 degrees; a trigger to control cleaning irrigation for the image sensor; and integrated irrigation also controlled by the trigger, and suction ports. The image inversion switch can be set to manual or automatic. If set to automatic, the image is inverted when the endoscope has curved past 90° and has reached 100°. A warning light on the monitor notifies the surgeon that the image has been inverted. The image will return to normal and the warning light extinguish as straightening the endoscope tip recedes past 90° back to 80°. There is, therefore 20° of the visual panorama which can be seen in either orientation as per the desires of the surgeon. The handle also has a switch next to the image inversion switch that reverses the motion of the vertical controller when the image is inverted. This motion control inversion continues the relationship of thumb control to tip motion. That is, forward thumb motion continues to depress the scope tip inferiorly. The motion control switch is set to automatic when the image control is concurrently set to automatic. The right to left controls do not need to be reversed as their orientation has not been affected by the inversion. The control unit for the vertical guide wires has the ability to detect when the flexible portion of the scope is flexed at the 90°. The detection may be accomplished either mechanically or electronically. The irrigation control trigger within the confines of the handle distantly electronically controls the irrigation pump which is not in the surgical field. Associated with the pump is the external heater for the irrigation fluid.

Figure 34A:
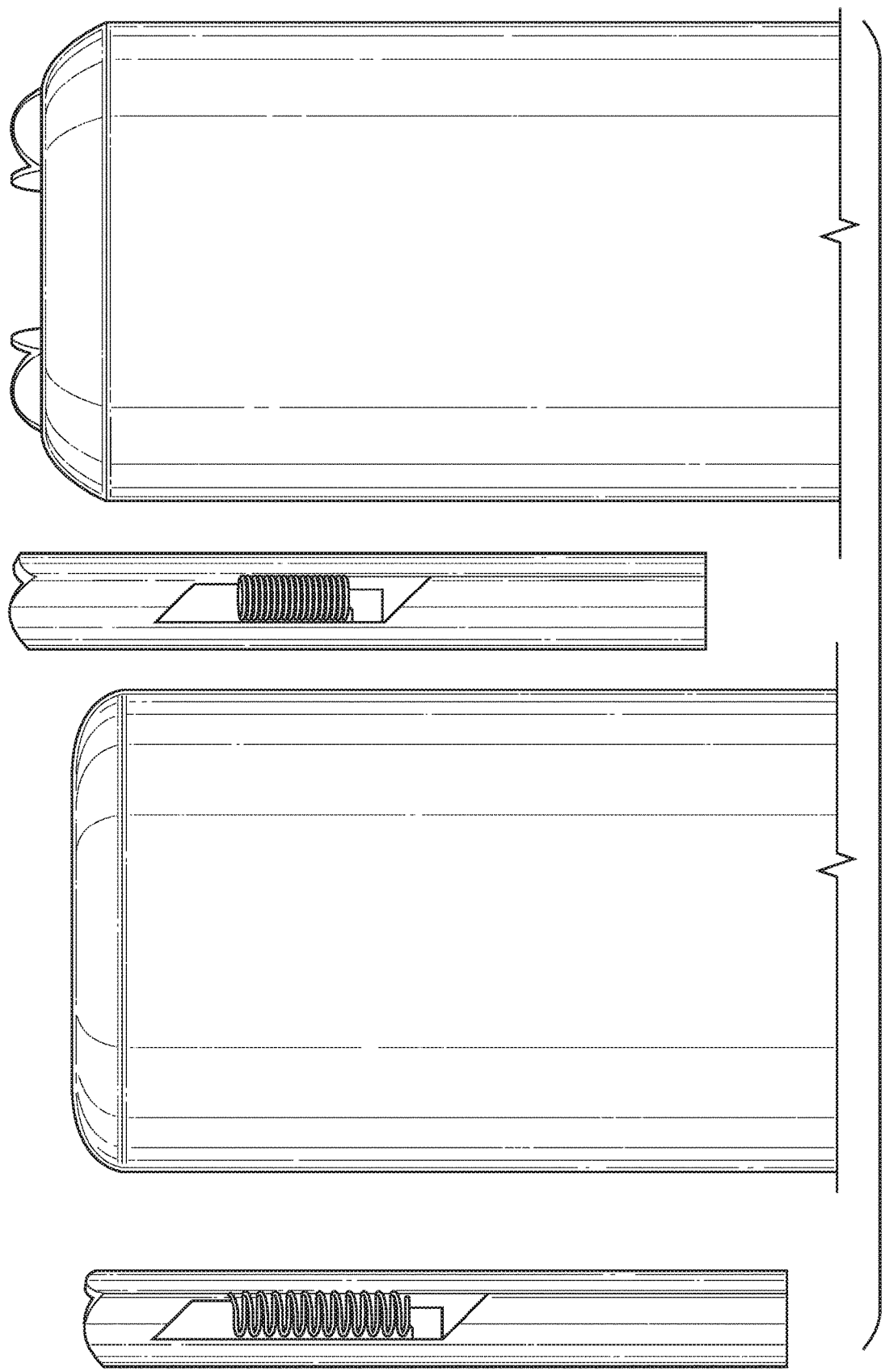
FIG. 34A is a composite side view of the tip of the irrigation sheath and is paired with its positioned extendable cannula.
Figure 34B:
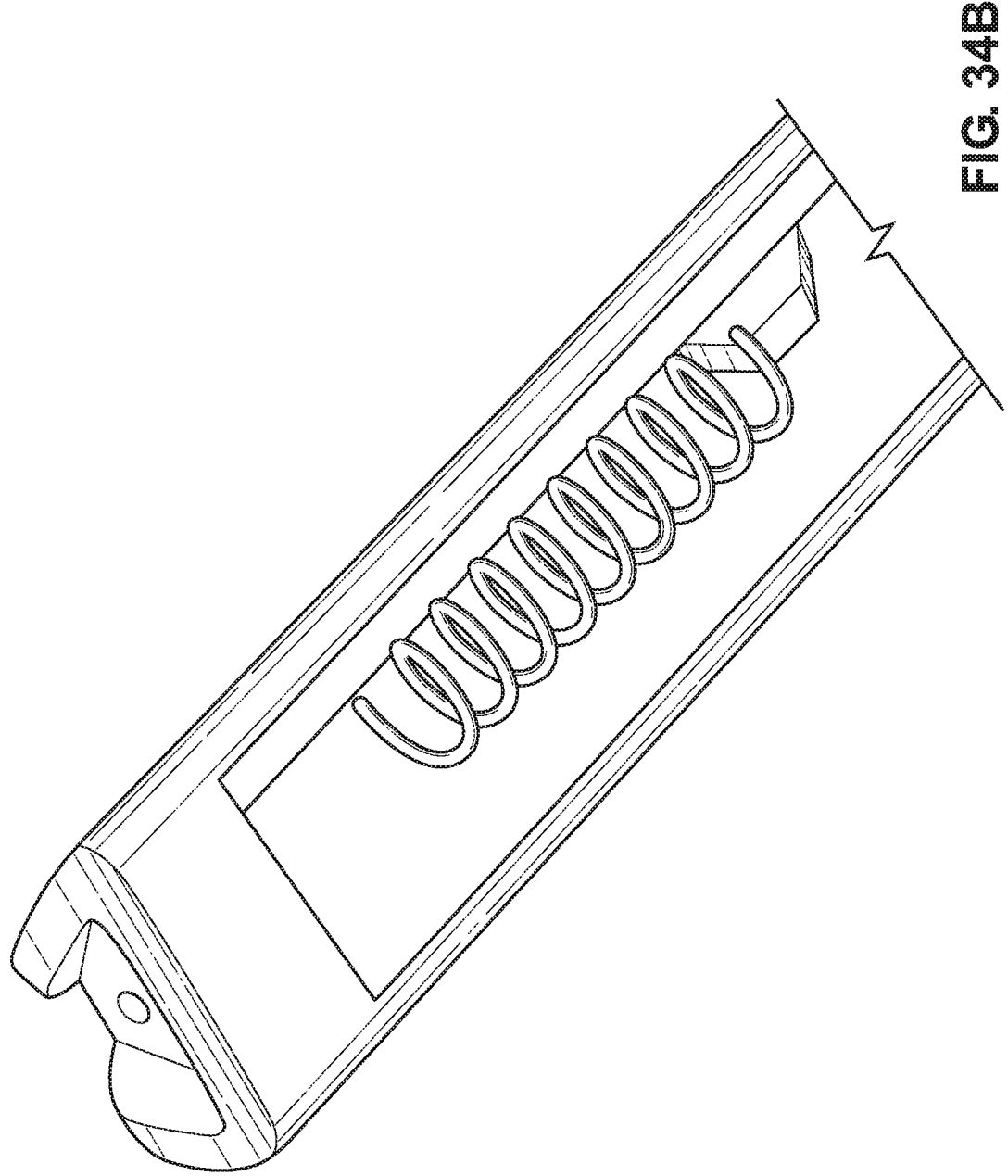
FIG. 34B illustrates a more restricted distal port size, which will create more of a jet nozzle and in turn allow better redirection of the stream towards the surgical field. Not apparent in the perspective

FIG. 34A is a composite side view of the tip of the irrigation sheath and is paired with its positioned extendable cannula. The same amount of both endoscopes is depicted. The isolated cannula to the left of each of the combined endoscope and irrigation sheath is at the same relative position as within the sheath. The two left drawings illustrate the low pressure state where the image sensor would be cleaned. The sheath and the circumferential baffle entirely covers the cannula in this condition. The extreme left drawing demonstrates the cannula with its internal spring under minimal compression. The two right figures show the cannula with its spring maximally compressed. The cannula has been pushed forward by the hydraulic pressure of the irrigation fluid. The spring is within the fluid stream which is contained within the confines of the sheath. The bracket which is below the spring is attached to the cannula. The bracket above the spring is attached to the side wall of the irrigation sheath and is at the same level in both drawings. The resistance to irrigation flow is what drives the extension cannula forwards. The spring, the dispensability of the circumferential baffle and its resistance to deformation, and the resistance along the side wall restricts the extension cannula's mobility. The longer the cannula's length the greater its resistance to movement. The cannula may be made of a material with a low coefficient of friction resistance such as polytetrafluoroethylene (Teflon). In some embodiments, the bottom bracket (attached to the cannula) could be enlarged or the distal port size could be restricted to become more of a jet nozzle if additional force is needed to drive the extension cannula forward. (See FIG. 34B left) The top surface of the jet nozzle is coplanar with the level of the notch produced by the centripetal extent of the paired support wings. This would allow better redirection of the stream towards the image sensor by the non-retracted baffle as well as providing a better jet stream by not contacting the retracted nozzle. Not apparent in the perspective FIG. 34B is that the hole in the distal cannula is a truncated conical shape to improve focusing the jet stream of irrigation fluid. The thickness of the plate through which the jet nozzle hole resides may be thick enough so that upon its complete extension, the irrigation fluid does not excessively leak between it and the side wall of the centrifugally displaced circumferential baffle. In FIG. B, the bracket which attaches on the side wall of the outer sheath is not drawn as in FIG. 34A. When the hydraulic pressure lessens, the springs return the cannulae to their initial state. The length of the cannula is somewhat arbitrary and depends upon the length of the image sensor FIG. 35A is the top view of the endoscope and the sheath which does not incorporate the jet tip nozzle within the extendable cannula. The left view is the low pressure condition with the baffle redirecting fluid flow centripetally. The right view is under the high pressure condition where the cannulae have protruded forwards exposing the full stream of field irrigation fluid. Seen within the open cannulae can be noted the springs which return the cannulae to their initial retracted state Irrigation Designs The tip irrigation mechanism and control deserves special additional discussion. Unlike presently available lens cleaners, these designs have two new abilities. The depression of the trigger on the hand piece results in the release of irrigating fluid which is conducted along the length of the endoscope ultimately to be ejected from the tip of the endoscope. When the trigger is only partially depressed, one of the various following mechanisms results in effective cleaning of the image sensor. When completely depressed, the irrigating fluid is released in (a) forceful stream(s) and can clear the surgical field of blood and debris and infection. Instead of using standard room temperature saline, it uses warm saline at a temperature of 45-50° (C.). This elevated temperature saline warms the tip and minimizes fogging of the image sensor from condensation but more importantly, when used for forced irrigation of the surgical field, may provide hemostasis. There is evidence, and ongoing research, into using warm saline for hemostasis. This was initially done in OB-GYN surgery but is only now also being used with Functional Endoscopic Sinus Surgery. The saline is heated externally before its introduction into the hand piece. The irrigator accomplishes cleaning and warming the image sensor, clearing the operative field of blood, debris, and infection and helps with hemostasis. The different designs of the endoscope sheaths are demonstrated in FIGS.: 25, 26, 31-58.

In all of these following discussions the irrigation fluid flow is biphasic. There are outward flow phases which either clean the image sensor or irrigate the field, and an inward phase at the end of irrigation which clears any hanging droplet off the image sensor to allow proper visualization. The suction phase is much shorter in duration and moves very little fluid. It is initiated upon the complete release of the hand piece trigger. For sterilization and to prevent long term problems with clogging of the fluid ejection areas/nozzles, the disposable irrigation sheath is designed to incorporate the fluid ejection areas/nozzles and is replaced for each surgical case. The hand piece in FIG. 24, houses an internal tube to conduct the irrigation fluid from the 'butt' end of the 'gun' to the 'muzzle.' This design maximizes ergonomics and minimizes entanglement. However, there are distinct advantages to keeping the irrigation tubing outside of the hand piece. The hand piece may alternatively be designed to have an external groove to conduct the tube along length of the 'gun' and prevent the tubing becoming bothersome. Sterilization and cleaning of the hand piece is significantly simplified by having an external disposable tube and there is also one less connection to leak. The tubing is completely replaced with each use which guarantees that there will be no need to replace the hand piece because of gradual tubing decay and leakage. The disadvantage of the external tube is where the tubing connects to the irrigation sheath. The external tube may have some play to allow for rotation of the knurled knob which allows for rotation of the endoscope within the hand piece. This extra loop of tubing might be more cumbersome than the arrangement designed where the internal tube is incorporated inside the rotating knob and rotates as a complete unit. The extra tubing for the rotation for the internal design is encased by the handle. The external surface of the cross section of the irrigation sheath may be circular to maximize the utility of the endoscope. This would allow rotation of the scope within the surgical field without undue manipulation of the tissues.

Design A

Figure 25:
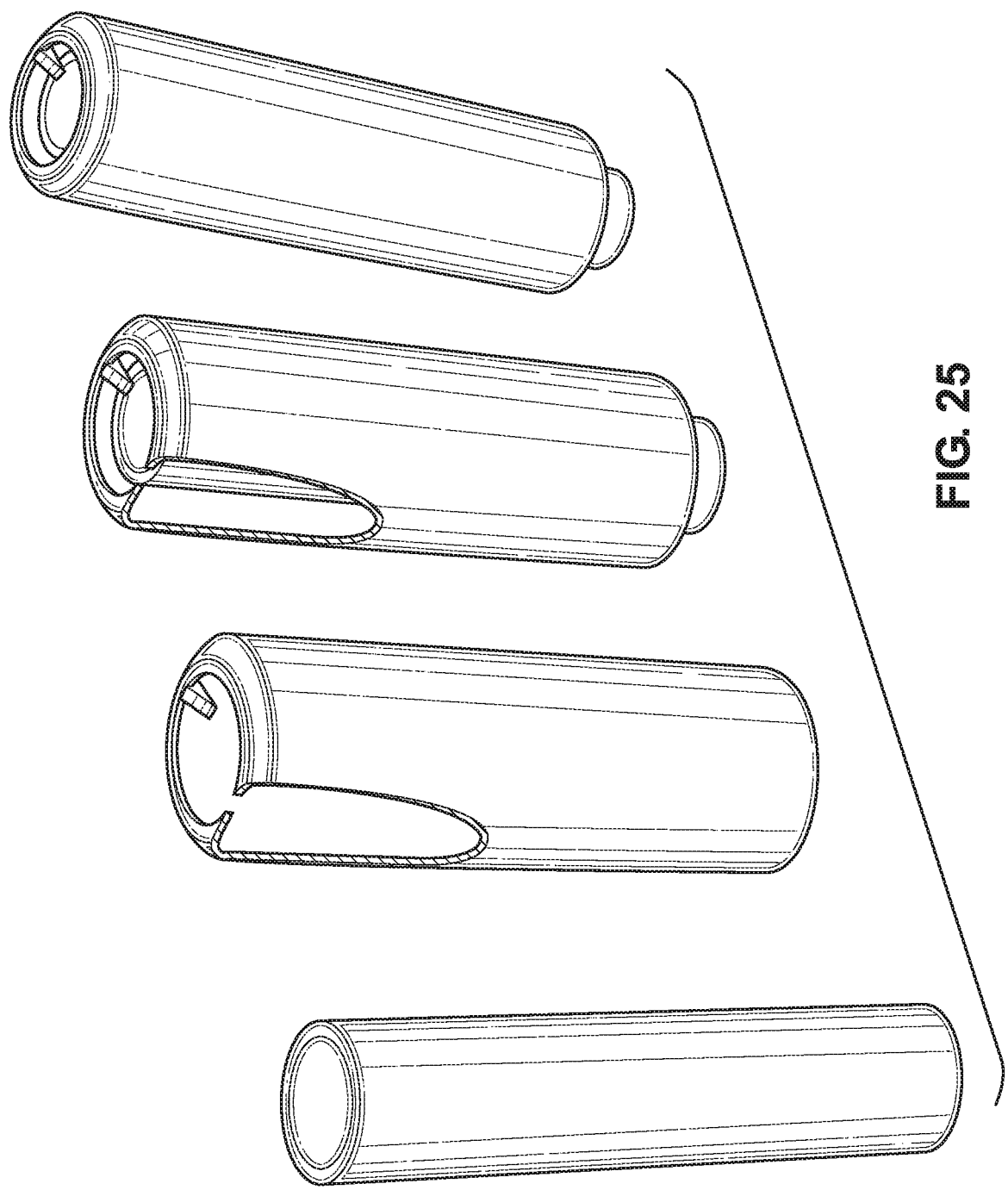
FIG. 25 illustrates the tip of an endoscope and irrigator assembly.

The first, sheath design (Design A shown in FIG. 25) is a semi-rigid cylinder, like the endoscope itself, and requires a larger combined diameter for the combined assembly of the scope and the sheath. The irrigating fluid would flow through whatever space is available between the endoscope and the larger relatively loosely fitting encompassing irrigation sheath. The shape of the sheath is passively controlled by the curve assumed by the endoscope. As the scope and sheath combination changes shape while curving, the endoscope is likely to contact the inner wall of the sheath at various points. This design would create a variable amount of conduit space depending upon the amount of curvature and, therefore, variable resistance to flow and ultimately variable flow rates and pressure delivery. Different sections of the ejection area would receive differing amounts of irrigating fluid depending on the shape of the scope as the resistance to flow changes. The ejection area has a symmetrical design and the restriction of flow could potentially cause individual sections not to eject irrigation fluid at all if the curvature sufficiently restricted flow in that area. The most distal end of the scope houses the chip tip camera which is rigid and does not bend. There is some redistribution of the irrigation fluids circumferentially at this location around the sheath which would help to equalize the pressures and flow of the ejected irrigation fluid. The functional transition from image sensor cleaning to field irrigation would be dependent on the amount of flow. Low flow rates would sweep across the image sensor redirected by the centripetally curved wall, or baffle, whereas high flow rates would force the centripetally directed image sensor cleaning streams to collide and force the combined irrigation stream outward away from the image sensor into the surgical fields. During the irrigation, the operator would transiently lose his visual field. This modification is the simplest but probably not the most effective. It does not have dedicated directed irrigation streams and the stream's direction would be more random. It might be required, however, depending on the design requirements of the endoscope.

Design B

The next design (Design B shown in FIG. 26) utilizes an irrigation sheath which surrounds a cylindrical endoscope but the sheath has separate dedicated conduit channels. There are two field irrigation and two image sensor irrigation ports. The two types of irrigations are attached to two different inflow circuits although both are controlled by the single trigger of the hand piece. The paired functionally similar ports for this arrangement are designed adjacent to each other for better efficacy. The surgical field irrigator is high volume and higher pressure. The image sensor irrigator is lower pressures and volumes. The cross section of the combined sheath and endoscope is relatively large in this design and could limit its accessibility in confined spaces. Design B does have an additional advantage that it is relatively easy to construct.

Modification of the Endoscope Cross Section

Designing an endoscope and its integrated irrigation sheath from the initial concept to final completed product has various advantages. It can be more ergonomic, efficient, and incorporate added abilities which are not possible when designing a sheath to be 'added on' to a previously available commercial product. The distal flexible segment of the endoscope and some of the more proximal rigid base does not need to be cylindrical. The rigid proximal shaft could be cylindrical for some distance and then change shape more distally. Designing an endoscope to have a non-cylindrical cross section has advantages which are discussed below. FIG. 27 illustrates my design of the cruciform endoscope. As noted above the endoscope has a soft, flexible inner protective sheath.

This cruciform shape modification is utilized for all of the following designs. The cruciform shape continues to allow the actuator arms to control curving the scope but leaves space for the transportation of irrigating fluid along its length. This space between the actuator arms, or wings, minimizes the entire combined assembly diameter of scope and irrigation sheath by allowing some of the space traditionally used in the construction of the endoscope for the fluid transport. The cruciform semi-rigid endoscope could be covered with its own inner covering/sheath. The designs A and B of the nozzles in the sheath at the end of the scope could be specialized as also noted in Designs A-F. In this design there are four longitudinal fluid conduits inherent in the design of the endoscope with the cruciform cross section. The transition in the cross sectional shape from circular to cruciform may take place adjacent to the hand piece. The remaining cylindrical most proximal portion of the endoscope is ensheathed by the irrigator and has an "O" ring to seal in the irrigation fluids. (FIGS. 31 & 32) The conduit channels are potentially isolated from each other and therefore could be independently controlled. This allows the selected conduit channels to be correctly supplied to the appropriate high or low pressure/volume irrigation supplies if desired. Irrigation fluid is introduced into the appropriate conduits by the depression of the hand piece trigger. Partial depression supplies those conduits which are for image sensor cleaning and complete depression of the trigger supplies the field irrigation ports. There may be design difficulties in hermetically isolating the two field irrigation channels from the two image sensor irrigation channels without significantly increasing the entire cross sectional diameter. The four conduits are not necessarily isolated from each other and may all connected to the same irrigation supply. As with all of the irrigation designs, complete release of the irrigation trigger actuates the mild, short duration suction, or reversal of flow of the irrigation fluid to remove any fluid on the image sensor is activated. This design minimizes the cross sectional diameter for the endoscope/irrigation sheath assembly although its construction is more technically challenging.

The common required function in all of the irrigation sheath designs is that of controlling the tip of the irrigator and effecting a change in the direction, force and volume of irrigation fluid on command. It requires a mechanism which is not too complicated or bulky. The following designs all utilize the variable amounts of pressure delivered to the tip by the irrigation fluid to accomplish these mechanical effects. The following designs have the advantage of not requiring separate isolated fluid conduits for individual high and low pressure fluid systems. Having only one set of fluid channels avoids the possible difficulties with the high pressure fluid errantly entering the low pressure area.

Design C

Figure 33:
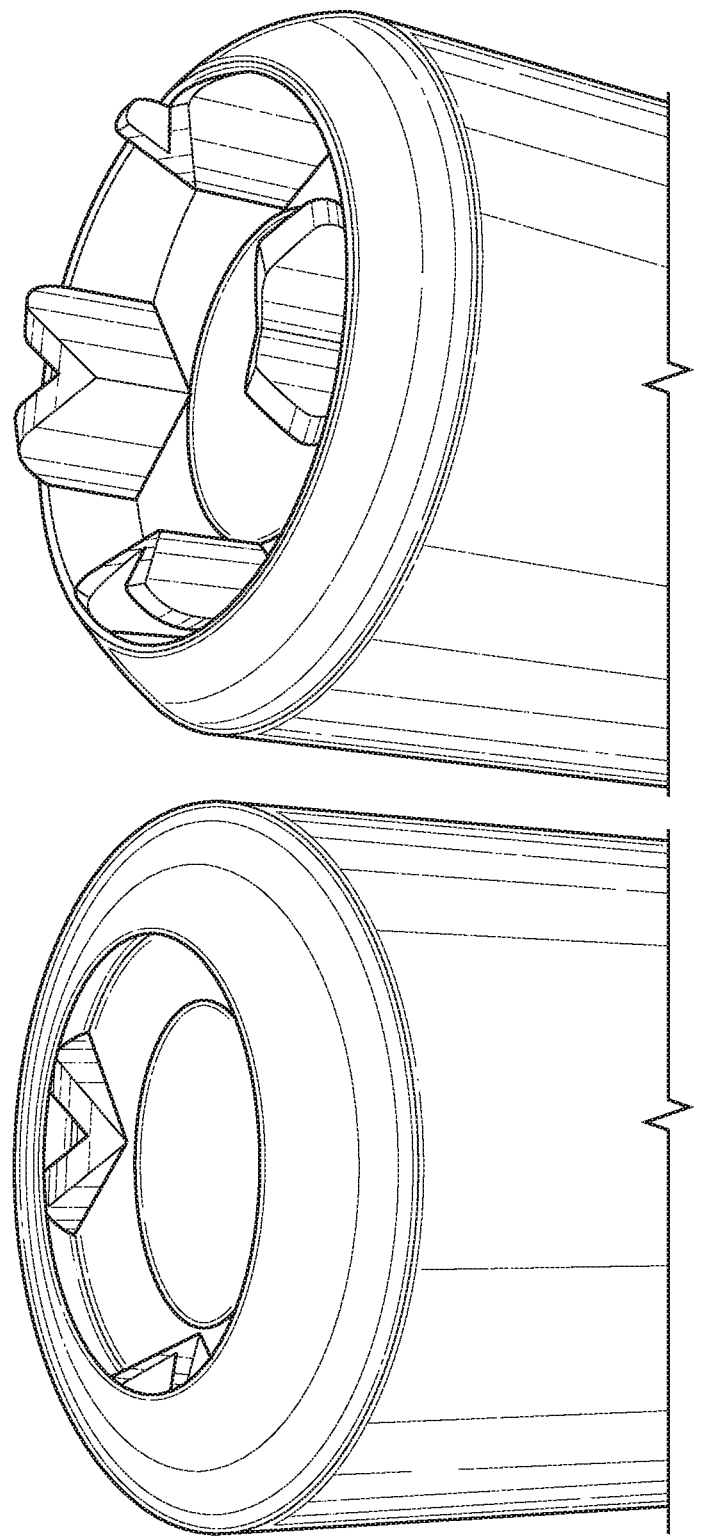
FIG. 33 is a perspective drawing of the tip of the irrigation sheath with the extending cannulae. The left drawing is in the low pressure condition where the irrigation fluid is directed across the image sensor for cleaning. The right drawing shows the forward extension of the cannulae moving a portion of the baffle centrifugally out of the way.

Design C utilizes an endoscope with a proximal cylindrical base and a distal cruciform cross-section (FIGS. 27-32). This design, (FIGS. 33-35) utilizes the irrigation fluid pressure to extend longitudinal cannulae residing in the hollows of the distal cruciform endoscope. Low pressure fluid runs through the cannulae and is directed by the circumferential baffle across the image sensor for cleaning. Higher pressures force the cannulae to protract forwards distending the soft walled circumferential baffle and allow the fluid stream to project forwards for field irrigation. The amount of forward movement for the cannulae to extend beyond the baffle is one to three millimeters. The four cannulae can be connected together to force them to move as a single unit. This interconnection may also stabilize any inward torsion of an individual cannula. Unfortunately, it might also increase the resistance of movement.

Design D

Figure 36:
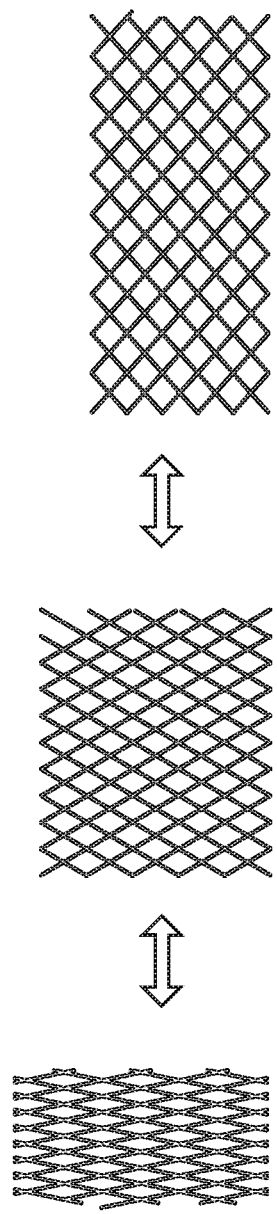
FIG. 36 depicts a biased cloth incorporated within a high compliance, waterproof matrix. The far left drawing is the initial state where the threads are oriented in a relatively steep, 70 degree angle. The center and right drawings demonstrate the horizontal spreading of the cloth. The resultant reduction in height is not linearly related to the increase in width, but is related to the Tangent function. This results in more traction and less motion in the vertical plane initially. The process is reversible as a result of the intrinsic recoil of the matrix material.
Figure 37:
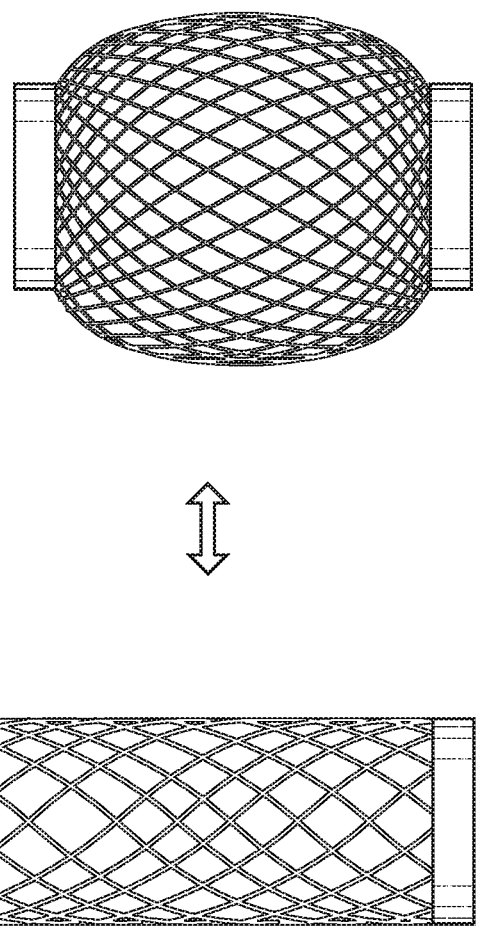
FIG. 37 is a three dimensional illustration of the effect of the biased cloth incorporated into a three dimensional expansion collar assembly. The proximal collar is fixed and sealed circumferentially around the more proximal irrigation sheath. The distal end is also fixed to a collar of fixed circumferential dimension but is capable of proximal and distal migration.
Figure 41:
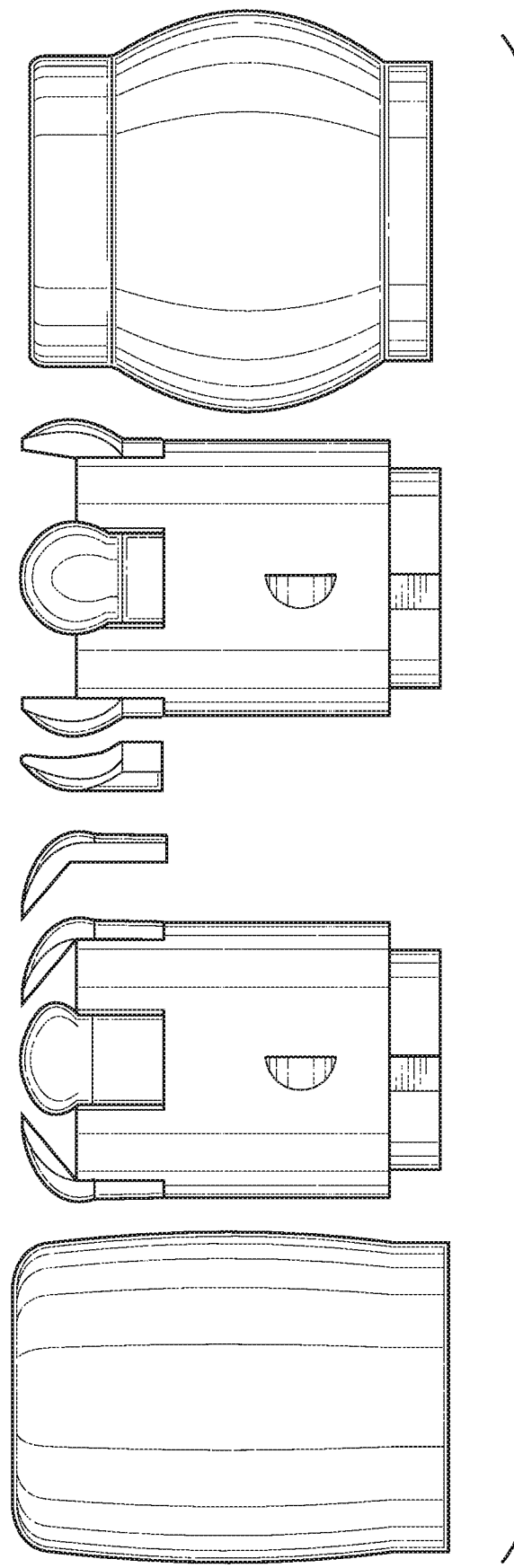
FIG. 41 is a side view of the irrigation tip. The endoscope is not in place. The left triad of drawings illustrates the deflated collar. To the far left is the deflated collar. Second to the left is the inner wall of the sheath with its fenestrations apparent. The fluid diverting baffles are seen in their basal state when not under pressure. Left of center is the baffle, made of fairly rigid material, and its attachment to the distal mobile edge of the inflatable collar with its rigid ring in the relaxed condition. The right triad of drawings illustrates the high pressure condition. To the right of center is the baffle when it is under tension during the high pressure state.

Other alternative designs can have the irrigation ports redirect flow by having directional baffles move into different configurations uncovering stationary conduits. The following is a preliminary discussion for several mechanisms. FIG. 36 is a planar demonstration of a bias cloth constructed from non-distensible threads. As the cloth is expanded in width, the height is required to shorten. The relationship of these changes is related to the Tangent of the thread angle. A relatively steep angle of the threads (70 degrees) was chosen to increase the vertical tractional pull relative to the horizontal pull which results during the distension. The design assumes that the materials on which the traction is to be applied is likely to require the extra traction at the onset of motion. This increase in traction is at the expense of speed of vertical shortening compared to the horizontal spread. At 45 degrees the two amounts of traction and their rates of speed are equal (neglecting frictional forces). Changing the initial angle of the biased threads in the final product will result in a fine tuning of the amount of traction versus distance, i.e. speed. Additionally, the percentage of the change in vertical height is related to the increasing width. Therefore, the amount of vertical distance that the cloth 'contracts' is a linear function of the total vertical height of the biased cloth multiplied by the percent change. These variables may be empirically determined during the construction and development stage. The cloth is embedded into a high compliance, elastic, waterproof material, and a possible example being Silastic or silicon.

The more proximal irrigation sheath extends distally under the distensible collar to provide a non-distensible internal irrigation sheath which has windows designed into its sidewall to accomplish two objectives. (FIG. 38) One is to allow the irrigation fluid to flow out of the interior sheath and around the exterior of the sheath but still be contained within the confines of the collar assembly. This equalizes the pressure to all irrigation ports by allowing the fluid to exit one sheath window and re-enter the internal sheath through a different window. Second, at low pressure and flow rates the compliance of the expandable portion is designed to be able to essentially maintain its shape. The irrigation fluid is then ejected through the irrigation ports and directed tangentially across the image sensor to clean it. At higher pressures and flow rates the compliance cannot maintain the shape of the expandable collar. As the configuration of the collar changes, it becomes wider in its center and shorter in length. (See FIG. 37)

The circumference of the collar relates to the width of the biased cloth in the above discussion (FIG. 36). Therefore, the change in the diameter of the expandable collar or sheath may increase only approximately one third as much as the required change in width to effect the same vertical change in height. (The diameter is the circumference divided by Pi.) Rigid collars are depicted at the ends both proximally and distally.

Design E

The inflating collar design provides retraction to move the baffles and uncover the irrigation holes to allow redirection of the field irrigation streams forwards (FIGS. 38-42). Design E is also based on the expanding collar platform design discussed in Design D. It continues to utilize the fenestrated extension of the proximal irrigation sheath which is covered by the expandable collar. It can be significantly improved by a modification that not only provides collinear axial traction, but also provides a centrifugal vector force. (Design E; See FIGS. 43-46) This improved design modification also better allows resetting the baffles to their initial starting alignment because there is no friction between adjacent components. (This might occur in Designs C and D.) The design re-assumes its initial shape and configuration because of the inherent recoil characteristics of the elastic material composing the cap situated on the distal portion of the expansion chamber.

Similar to Design D, the irrigation fluid is conducted distally in the conduit channels inherent in the cruciform endoscope. The irrigation sheath again has fenestrations which are present near its distal tip. That portion of the sheath has the surrounding collar. There are two presented design modifications depicting alternative fluid flow patterns. One modification is identical to Design D (FIG. 43C). The collar receives some fluid as the main stream passes by on the way to the exit nozzles. There is very little flow through the collar except to redistribute and equalize pressures amongst the different fenestrations. The direction of flow is essentially from the internal sheath through the fenestrations into the collar. The second modification (FIG. 43C) forces all irrigation fluid through the collar by diverting flow into the collar first and then redistributing back into the internal sheath. The direction of flow is in the opposite direction. FIG. 43 illustrates the different cross sections at the distal tip of the cannula.

Design F

The final and preferred design also has the minimal amount of moving parts. Design F, may have only a hollow circumferential baffle at the end of the endoscope which connects to the longitudinal conduits which run along the length of the cruciform endoscope (FIG. 47-49). It is constructed from a soft, pliable material which has elastic memory. Under both the basal condition (no flow) and in the low pressure condition, the baffle is not significantly 'inflated' or distorted. Any irrigation fluid introduced into the baffle circulates within the baffle channel and ultimately is released through the exit jet ports. Any irrigation stream released at this time is directed centripetally towards the centrally located image sensor for cleaning. If the trigger on the hand piece is further depressed and the irrigation stream flow and pressure is increased, the baffle is 'inflated' or distended. This change in configuration causes the irrigation stream to arc from centripetally to directly forwards to irrigate the visualized surgical field. The tip of the irrigation sheath merely bulges forward to redirect the flow of the irrigation stream. The release of the trigger causes a reduction in flow and pressure and the baffle reassumes its original baseline configuration because of the inherent elastic recoil of the material from which the baffle is constructed. As in all of the irrigation designs, the complete release of the hand piece trigger causes a short duration reversal of irrigation flow to remove any remaining fluid droplets on the image sensor. This reversal of flow would also help to invert the inflated baffle back to the initial concave configuration. Alternatively, the inflating baffle can be individual (FIGS. 50-58). In this construction each inflatable baffle in situated at the end of each of the four longitudinal conduits in the cruciform endoscope. This construction with isolated, individual nozzles and the previously described construction of the cruciform endoscope where the actuator arms or wings continuously extend to the distal end of the image sensor does not allow for redistribution of irrigation fluid and the equalization of pressure, however.

To overcome the inability of this design to equalize fluid pressure when using individual baffles, the cruciform wings are distanced from the sides of the image sensor housing (FIGS. 57 and 58) which is one solid piece and does not bend. The most proximal wings at the base of the camera segment are still attached to permit the final angulation of the image sensor.

The stream of irrigation fluid redirects from centripetal to forwards and back again in a continuous arc of irrigation dependent only on the pressure delivered and controlled by the trigger on the hand piece. This design does not require individually separated high and low pressure conduits. Nor does it require extra cross section space caused by bowing of the external sheath walls to change its configuration. (FIG. 56) It does not impinge on the camera's visual field. It has the ability to equalize the ejected fluid pressure and help equalize flow.

Consideration was also given to the possibility of designing the end of the endoscope sheath with an incorporated clear plastic lens cover (See FIGS. 57 & 58). This would help assure a hermetically sealed sheath and avoid fluid leakage. This potential modification would negate the concerns for correctly placing the inner self-sealing flange in this design. But this design requires the utilization of multiple materials making its construction more difficult. It was felt that this design without a lens cover would not be problematic in its construction. Assuring that the lens cover is correctly positioned over the image sensor would be more difficult to consistently reproduce which might create visual distortions. Also concerning with this design is the likelihood that gas bubbles from the irrigation fluid would inevitably get in between the cover and the image sensor causing visual distortions and obstructions. The distal tip of the camera housing could be designed to flare at the end by the lens cover. This would help to stabilize the sheath but would make alignment of the irrigation hole positioning more inconsistent. This design continues to have space just proximal to the ejection ports to allow for fluid mixing and pressure equalization.

Supplemental Locking Device

If the innate friction between the two adjacent linkages, while all guide wires are held immobile and under tension, is enough to limit motion or rotation, no other locking device is necessary. The designs above would be adequate in construction. The linkages may be able to move or rotate when only selected guide wires require it. In the cruciform endoscope designs there are four guide cables. For the endoscopes discussed in the main proposal body above which have motion in both Y and Z planes the guide wires alone are adequate to increase tension of the locking device. There is the possibility to have an endoscope with two guide wires and an additional two tensioning wires. The opposing male and female surfaces may be selected appropriately to enable these two frictional conditions of both movement and rigidity. The following design discussion enables the linkages to be held more rigidly in position and be released to allow free motion at will.

Figure 62C:
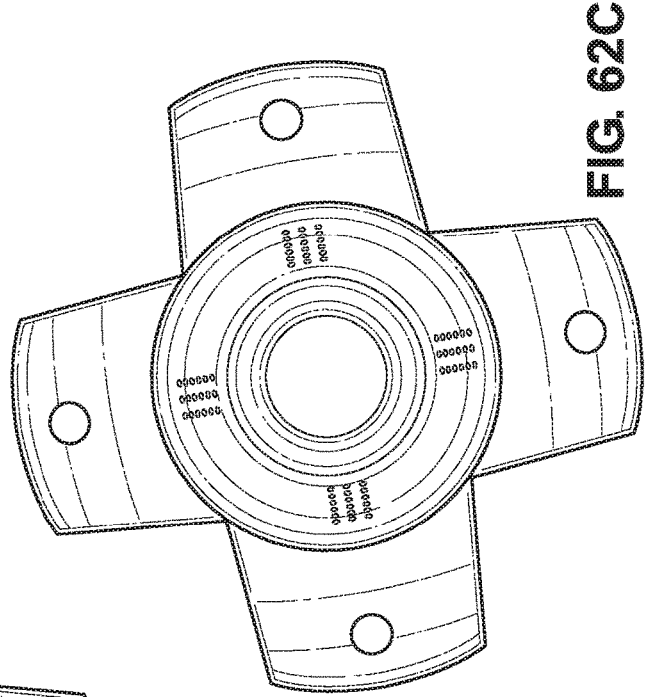
Figure 62B:
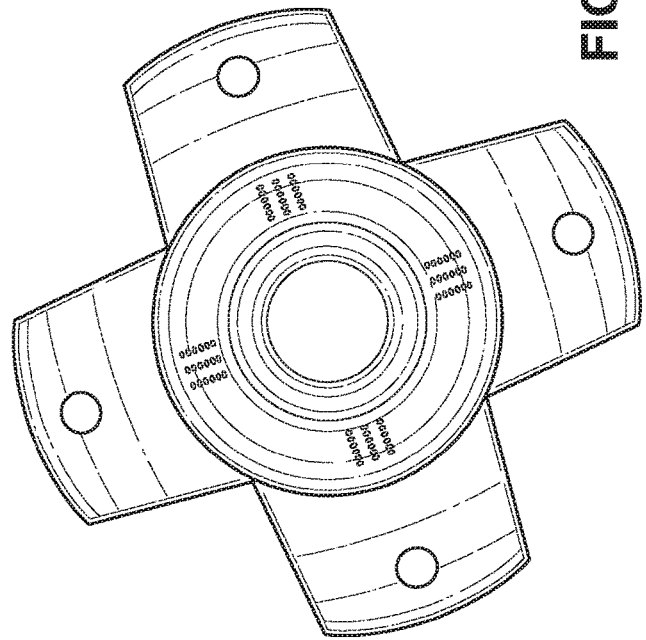
Figure 63A:
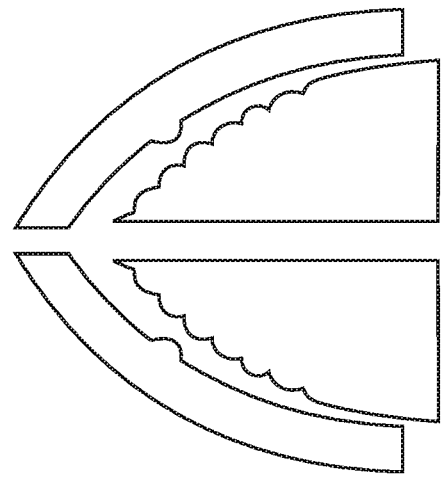
Figure 63B:
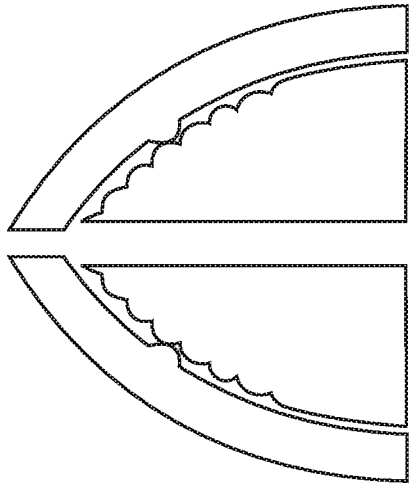
Figure 63C:
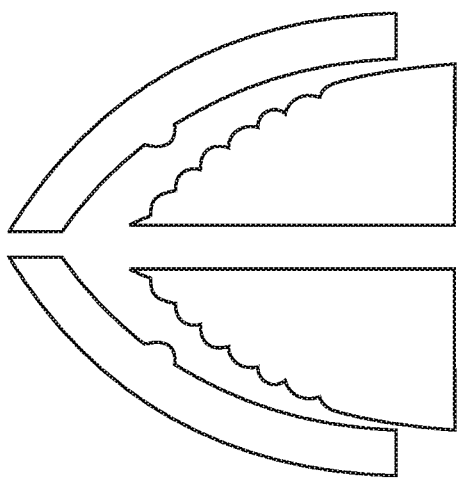
Figure 63D:
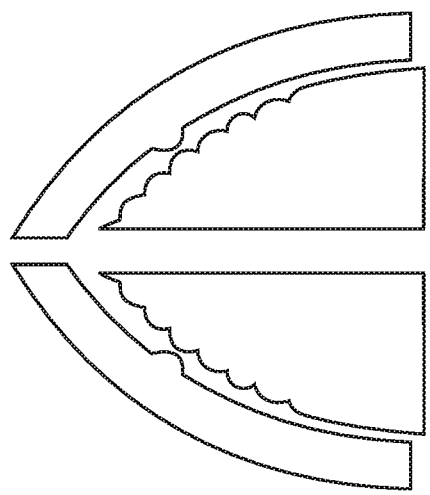

The following design depends on the traction of the guide wires to pull more distal linkage segments proximally to impact adjacent linkages. As each linkage can independently rotate 15°, each linkage was selected to have locking angles every 5°. The endoscopes can now still rotate 180° but lock in 5° increments. The external male convex portion of the linkage has discrete trianguloid pits in its surface which are separated by 5° arcs of curvature. These arcs are both in the Y and Z planes on the respective aspects of the semispherical surface. See FIG. 59. The female concave portion of the linkage has a single trianguloid appendage on each of the four Y and Z aspects. The pit and appendage are each shaped as an elongated pyramid with its long axis coaxial to the length of the scope. It has a rhomboid base and four triangular sides. This appendage fits into a respective pit on the male surface. Each paired Y and Z aspect has a matching appendage on the female surface and matching sets of pits on the male surface. See FIG. 60. As the linkages rotate, the appendages align over a corresponding pit every 5° of arc in any rotational direction. Also see FIGS. 61 & 62. Upon tightening of the guide wires and/or the tensioning wires the appendage is drawn into and locked into the best aligned matching sets of pits. See FIG. 63. The trianguloid appendage is designed to be symmetrical to the radius of the hemisphere at approximately 53°. See FIG. 64. This ensures a firm inter-linkage lock under tension. When the linkages are not under tension it allows for easy disengagement and rotation of the linkages in any direction. The corresponding surfaces for the appendages are parallel not only to each other and the corresponding pit but are also collinear to the combined directional vector pull of the wires, both guide and tensioning wires, and hence collinear to the direction of travel of the distal linkage towards the more proximal one. This alignment permits smooth locking. See FIG. 63.

Other embodiments include a wireless unit made by enclosing batteries for the image sensor and circuitry for LED illumination and image transmission, and the electronically assisted curvature control within the pistol grip. The unit may then be attached only to the suction tube and irrigation fluids. These could be integrated with the handle to minimize the presently encumbering entanglement of wires and hoses in today's operating room.

The Electronic Correction Circuit

The electronic correction circuit may be placed between the scope and the monitor input. Separate circuit housing allows for the utilization of any monitor. It may also be incorporated into a monitor. There are controls which allow for gradual axial rotation of the image. There is also a switch which corrects for image inversions. There may be a visual on screen warning when this inversion switch has been activated. A warning may also notify the operator when the vertical curvature exceeds 90 degrees. There is also a switch which reverses the vertical motion of the thumb control when the image is inverted. These controls are optimally located on the hand piece for control by the surgeon. Utilizing lightweight electronic controls which activate mechanisms out of the surgical field such as; pumps, heaters, and images, minimizes the weight of the hand piece and surgeon fatigue.

Future Enhancements

The endoscope described herein has applications in fields in surgical medicine in multiple specialties and subspecialties (Urology, General Surgery, Obstetrics-Gynecology, Neurosurgery, Plastic Surgery, Gastroenterology, Pulmonary Medicine, etc.). Specific to Otolaryngology Head and Neck Surgery, it has application to nasal and sinus work as well as skull-base surgery.

Further, the endoscope may be employed with other types of systems such as, robotics, non-traditional endoscopy, voice recognition and command controls, virtual reality surgery, hands free optical aiming and focus, and 3 dimensional binocular visualization. With appropriate magnification it can also be used for microsurgery. Its additional flexibility provides further options and can be used for the introduction of various therapeutic modalities such as LASER.

In one embodiment, the endoscope has the ability to flex in only one plane of motion which is similar to the prototype in FIG. 21. It can still see around structures and can be used effectively to operate within cramped locations such as the maxillary sinuses and frontal sinuses or in office settings. The design uses an endoscope which has an elliptical cross section and is intended to be used with an irrigation sheath which is also elliptical. The sheath's ellipse long axis is at right angles to the scope's ellipse long axis. (See FIG. 65) This provides space to supply the irrigation fluids. Additionally the endoscope curves at right angles to the long axis of the irrigation sheath aiding to its flexibility. The concepts of using a high definition camera, incorporated lighting, warmed saline, and the hand piece described above with its electronic controls is still utilized. For example, the endoscope and/or its associated system may be configured such that fluid is warmed through a tube in a hot water bath or between two opposing heated plates. The irrigation ports illustrated are similar to the individual ports described in Design F above, which do not allow for equalization of pressure. (See FIGS. 69 & 70) There are only two opposing ports and they are incorporated into the distal tip of the irrigation sheath. As described above they are also designed not to obstruct visualization of the camera. There is an additional guide wire to create more friction between the linkages to lock the curvature in place but does not have any effect on the scope's curvature. It is placed adjacent to the central lumen in the middle of each linkage. (See FIG. 66)

What is claimed:

1. A system, comprising:
   a hand control electrically and mechanically coupled to a semi-rigid endoscope, the hand control comprising an input port configured to receive irrigant fluid;
   the semi-rigid endoscope, comprising:
   a rigid proximal portion extending from the hand control, the rigid proximal portion being configured to be mechanically rotated by and relative to the hand control about a longitudinal axis, and the rigid proximal portion remaining elongate along the longitudinal axis;
   a flexible tip extending directly from the rigid proximal portion, wherein the flexible tip is configured to move relative to the rigid proximal portion along a lateral direction that is perpendicular to the longitudinal direction, wherein the flexible tip is configured to move relative to the rigid proximal portion along a transverse direction that is perpendicular to both the longitudinal and lateral directions, and wherein the hand control is configured to direct movement of the flexible tip along the lateral and transverse directions;
   at least one lumen in fluid communication with the input port, the at least one lumen being configured to transfer irrigant fluid to and from the flexible tip;
   a baffle at the flexible tip, wherein the baffle is configured to direct ejection of the irrigant fluid; and
   at least one sensor coupled to the flexible tip, the at least one sensor being configured to detect radiation within a field of view extending from the flexible tip; and
   a screen electrically coupled to the hand control and the at least one sensor, the screen displaying an image that is based upon a digital signal from the at least one sensor,
   wherein the system automatically reorients the image displayed on the screen when the semi-rigid endoscope is retroflexed more than 90 degrees.

2. The system of claim 1, wherein the flexible tip comprises a plurality of segments configured to flex along both the lateral and transverse directions.

3. The system of claim 1, wherein the flexible tip defines a distal portion and a proximal portion spaced along the longitudinal direction from the distal portion, wherein said distal and proximal portions of the flexible tip have a rate or range of curvature that are sequential or synchronous.

4. The system of claim 1, wherein the at least one sensor comprises an integrated circuit chip.

5. The system of claim 1, wherein the radiation is electromagnetic radiation, and the at least one sensor is configured to detect electromagnetic radiation having a frequency extending from gamma to infrared frequencies or within the spectrum visible to humans.

6. The system of claim 1, wherein the semi-rigid endoscope is configured to visualize an interior region of a nose or sinus cavity.

7. A semi-rigid endoscope, comprising:
a rigid proximal portion that remains elongate along a longitudinal direction;
a flexible tip extending directly from the rigid proximal portion, wherein the flexible tip is configured to move relative to the rigid proximal portion along a lateral direction that is perpendicular to the longitudinal direction, and wherein the flexible tip is configured to move relative to the rigid proximal portion along a transverse direction that is perpendicular to both the longitudinal and lateral directions;
at least one lumen configured to transfer irrigant fluid to and from the flexible tip;
a baffle at the flexible tip, wherein the baffle is configured to reversibly adjust between a first configuration whereby the baffle directs irrigant fluid towards the flexible tip, and a second configuration whereby the baffle directs irrigant fluid towards a surgical field extending from the flexible tip, wherein the reversible adjustment of the baffle between the first configuration and the second configuration is based on pressure of the irrigant fluid; and
at least one sensor coupled to the flexible tip, wherein the at least one sensor is configured to detect radiation within the surgical field.

8. The system of claim 1, further comprising at least one light emitting diode coupled to the flexible tip and electrically coupled to a power source, the at least one light emitting diode configured to illuminate the field of view.

9. The system of claim 1, further comprising:
a first guide wire and a second guide wire disposed opposite the first guide wire, wherein when one of the first or second guide wires tightens and the other of the first or second guide wires relaxes, the flexible tip curves towards the first or second guide wire that is tightened; and
a first linkage having a distal surface and a proximal surface, and a second linkage having a distal surface and a proximal surface, the second linkage being disposed proximal to the first linkage such that the distal surface of the second linkage is operably coupled to the proximal surface of the first linkage,
wherein the first and second linkages each include a locking device that is configured to lock the first linkage relative to the second linkage when they move relative to each other to lock the flexible tip at a curvature.

10. The system of claim 9, further comprising a third linkage having a distal surface and a proximal surface, the third linkage being disposed proximal to the second linkage and wherein the flexible tip moves at either the first linkage, the second linkage, and/or the third linkage.

11. The system of claim 9, wherein the locking device comprises:
at least one protrusion that protrudes from an opposing surface of each of the first and second linkages; and
at least one recess that recedes into an adjacent surface of each of the first and second linkages, the at least one recess configured to receive the at least one protrusion to thereby lock the at least one protrusion with respect to the at least one recess.

12. The system of claim 1, wherein the hand control is configured to adjust, invert, and/or rotate the image displayed on the screen.

13. The system of claim 1, further comprising a pump fluidly coupled to the input port and electrically coupled to the hand control, the pump being configured to transfer the irrigant fluid to and from the flexible tip.

14. An endoscope assembly comprising:
a hand control comprising an input port configured to receive irrigant fluid; and
a semi-rigid endoscope coupled to the hand control, the semi-rigid endoscope comprising:
an inner body comprising:
a rigid proximal portion that remains elongate along a longitudinal direction;
a flexible tip distal to the rigid proximal portion, wherein the flexible tip is configured to move in at least two dimensions; and
at least one sensor configured to detect radiation within a field of view extending from the flexible tip; and
an outer sheath configured to releasably receive the inner body, the outer sheath defining a first lumen configured to receive the inner body, a centripetal flange disposed at a distal end of the outer sheath, wherein a dissolvable material is coupled to the centripetal flange, wherein the dissolvable material is initially rigid, and dissolves when coming into contact with a fluid to expose the first lumen,
wherein, when the inner body is received in the outer sheath, at least one second lumen is defined between an inner surface of the outer sheath and an outer surface of the inner body to transfer irrigant fluid to and from the at least one sensor.

15. The system of claim 1, further comprising an emitter that is configured to emit electromagnetic radiation having a frequency from gamma to infrared frequencies or within the spectrum visible to humans, wherein the at least one sensor is configured to detect the electromagnetic radiation.

16. The system of claim 1, wherein the semi-rigid endoscope has an outside diameter between four and eight millimeters.

17. The system of claim 1, wherein:
the rigid proximal portion, the flexible tip, and the at least one sensor are part of an inner body, and
the at least one lumen and the baffle are part of an outer sheath that is configured to releasably receive the inner body.

18. The system of claim 1, wherein the flexible tip is configured to be releasably lockable at a curvature.

19. The system of claim 1, wherein the flexible tip is configured to releasably lock along the lateral direction and the transverse direction at discrete angles.

20. The system of claim 1, wherein the hand control is configured to control rotation of the rigid proximal portion about the longitudinal axis.

21. The system of claim 17, wherein an inner diameter of the outer sheath is substantially equal to the outer diameter of the inner body.

22. The system of claim 1, wherein the rigid proximal portion extends from a proximal end, and the proximal end of the rigid proximal portion is directly connected to the hand control.

23. The system of claim 1, wherein the hand control comprises an actuator that is configured to control the rotation of the rigid proximal portion relative to the hand control.

24. The semi-rigid endoscope of claim 7, wherein the flexible tip comprising a plurality of the baffle spaced circumferentially about the flexible tip.

25. The semi-rigid endoscope of claim 7, having an outside diameter between four and eight millimeters.

26. The endoscope assembly of claim 14, further comprising an emitter that is configured to emit electromagnetic radiation having a frequency from gamma to infrared frequencies or within the spectrum visible to humans, wherein the at least one sensor is configured to detect the electromagnetic radiation.

27. The endoscope assembly of claim 14, wherein the semi-rigid endoscope has an outside diameter between four and eight millimeters.

* * * * *